(12) United States Patent
Benning et al.

(10) Patent No.: US 9,657,304 B2
(45) Date of Patent: May 23, 2017

(54) GENETICALLY ENGINEERED PLANTS WITH INCREASED VEGETATIVE OIL CONTENT

(71) Applicant: Board of Trustees of Michigan State University, East Lansing, MI (US)

(72) Inventors: Christoph Benning, East Lansing, MI (US); Sanjaya, East Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 348 days.

(21) Appl. No.: 13/938,784

(22) Filed: Jul. 10, 2013

(65) Prior Publication Data

US 2014/0020133 A1 Jan. 16, 2014

Related U.S. Application Data

(60) Provisional application No. 61/669,990, filed on Jul. 10, 2012.

(51) Int. Cl.
*C12N 15/82* (2006.01)
*A01H 5/10* (2006.01)
*C07K 14/415* (2006.01)

(52) U.S. Cl.
CPC ........ *C12N 15/8247* (2013.01); *C07K 14/415* (2013.01)

(58) Field of Classification Search
None
See application file for complete search history.

(56) References Cited

U.S. PATENT DOCUMENTS

2011/0035841 A1* 2/2011 Plesch et al. ............... 800/281

OTHER PUBLICATIONS

Whisstock et al, 2003, Quarterly Reviews of Biophysics, 36:307-340.*
Shen et al, 2010, Plant Physiology, 153:980-987.*
Vigeolas et al, 2004, Plant Physiology, 136:2676-2686.*
Ma et al, 2015, Plant Journal, 83: 864-874.*
Sanjaya et al, 2011, Plant Biotechnology Journal, 9:874-883, published online Feb. 17, 2011.*
Weigelt et al, 2009, Plant Physiology, 149:395-411.*

* cited by examiner

*Primary Examiner* — Jason Deveau Rosen
(74) *Attorney, Agent, or Firm* — Schwegman Lundberg & Woessner, P.A.

(57) ABSTRACT

The invention relates to genetically modified agricultural plants with increased oil content in vegetative tissues, as well as to expression systems, plant cells, seeds and vegetative tissues related thereto.

31 Claims, 10 Drawing Sheets
(6 of 10 Drawing Sheet(s) Filed in Color)

GENETICALLY ENGINEERED PLANTS WITH INCREASED VEGETATIVE OIL CONTENT

This application claims benefit of the priority filing date of U.S. Patent Application Ser. No. 61/669,990, filed Jul. 10, 2012, the contents of which are specifically incorporated herein by reference in their entirety.

This invention was made with government support under Grant No. DE-FC02-07ER64494 by the Department of Energy Great Lakes Bioenergy Research Center Cooperative Agreement. The government has certain rights in the invention.

BACKGROUND OF THE INVENTION

Plant oils such as triacylglycerols (TAGs) are useful for food, industrial feedstock and biofuel production. TAG is generally harvested from the seeds of oil crop species, such as canola. However, engineering of crops that product oils in non-seed tissues (leaves and roots) is an alternative way to produce feed stocks for high energy transportation biofuels or even jet fuels.

Fuels are typically produced from petroleum products, but such production involves considerable cost, both financially and environmentally. Sources of petroleum must be discovered, but petroleum exploration is an expensive and risky venture. The cost of exploring deep water wells can exceed $100 million. In addition to the economic cost, petroleum exploration carries a high environmental cost. For example, offshore exploration frequently disturbs the surrounding marine environments.

After a productive well is discovered, the petroleum must be extracted from the Earth, but such extraction is expensive and, even under the best circumstances, only 50% of the petroleum in a well can be extracted. Petroleum extraction also carries an environmental cost. For example, petroleum extraction can result in large seepages of petroleum rising to the surface. Offshore drilling involves dredging the seabed which disrupts or destroys the surrounding marine environment.

After extraction, petroleum must be transported over great distances from petroleum producing regions to petroleum consuming regions. In addition to the shipping costs, there is also the environmental risk of oil spills.

In its natural form, crude petroleum extracted from the Earth has few commercial uses. It is a mixture of hydrocarbons (e.g., paraffins (or alkanes), olefins (or alkenes), alkynes, napthenes (or cylcoalkanes), aliphatic compounds, aromatic compounds, etc.) of varying length and complexity. In addition, crude petroleum contains other organic compounds (e.g., organic compounds containing nitrogen, oxygen, sulfur, etc.) and impurities (e.g., sulfur, salt, acid, metals, etc.). Hence, crude petroleum must be refined and purified before it can be used commercially.

Due to the inherent challenges posed by petroleum, there is a need for a renewable petroleum source which does not need to be located by extensive exploration, extracted, transported over long distances, or substantially refined like petroleum. There is also a need for a renewable oil source that can be produced economically without environmental damage.

SUMMARY

The invention relates to production of oil in non-seed tissues (e.g., leaves, stalks, stems and roots) of a variety of transgenic plants that involves the expression of at least two nucleic acids to inhibit starch accumulation and increase the conversion of sugars into oil.

One aspect of the invention is a plant with a plant expression system that includes:

(a) a first expression cassette comprising a nucleic acid segment encoding a WRINKLED1 transcription factor, (b) a second expression cassette comprising a nucleic acid segment encoding an inhibitory nucleic acid capable of hybridizing to an ADP-glucose pyrophosphorylase nucleic acid, or (c) a combination thereof;

wherein the plant's vegetative tissues have more oil than a plant of the same species that does not contain the plant expression system.

Another aspect of the invention is a seed with a plant expression system that includes:

(a) a first expression cassette comprising a nucleic acid segment encoding a WRINKLED1 transcription factor, (b) a second expression cassette comprising a nucleic acid segment encoding an inhibitory nucleic acid capable of hybridizing to an ADP-glucose pyrophosphorylase nucleic acid, or (c) a combination thereof;

wherein the seed develops into a plant with vegetative tissues that have more oil than a plant developed from a seed of the same species that does not contain the plant expression system.

The plants and seeds can be of various species. Examples of species of plants and/or seeds that can have such a plant expression system include alfalfa (e.g., forage legume alfalfa), algae, avocado, barley, broccoli, Brussels sprouts, cabbage, canola, cassava, cauliflower, cole vegetables, collards, crucifers, grain legumes, grasses (e.g., forage grasses), jatropa, kale, kohlrabi, maize, miscanthus, mustards, nut sedge, oats, oil firewood trees, oilseeds, potato, radish, rice, rutabaga, sorghum, soybean, sugar beets, sugarcane, sunflower, switchgrass, tobacco, tomato, turnips, and wheat. In some embodiments, the plant is a *Brassicaceae* or other *Solanaceae* species. However, in some instances the plant, the seed, and tissues from the plant are not an *Arabidopsis thaliana* plant, seed, or tissue.

DESCRIPTION OF THE FIGURES

The patent or application file contains at least one drawing executed in color. Copies of this patent or patent application publication with color drawing(s) will be provided by the Office upon request and payment of the necessary fee.

FIG. 1B) in plants. The constructs are referred to as 35S-AGPRNAi (FIG. 1A) and AGPRNAi-WRI1 (FIG. 1B), where WRI1 is a WRINKLED1 coding region (e.g., At3g54320), P35S is the cauliflower mosaic virus 35S promoter, PatB33 is the Patatin B33 promoter, HptII is hygromycin phosphotransferase II, NptII is neomycin phosphotransferase II, AGPase is the ADP-glucose pyrophosphorylase small subunit of AGPase (AJ271162), nos is the nopaline synthase terminator sequence, T35S is the cauliflower mosaic virus terminator sequence, Int refers to an intron/linker, His is a His tag, LB is the left border, and RB is the right border.

FIG. 3A shows transgenic rutabaga plants expressing the GUS gene. FIG. 3B shows electrophoretically separated PCR products illustrating that GUS transcripts are expressed by the transgenic plants. FIG. 3C shows GUS-staining (blue color) in transgenic rutabaga plant leaves from transgenic lines 3 and 4, compared to a control leave from a wild type plant that received only the vector (no GUS coding region).

FIG. 4A shows four Ti transgenic rutabaga lines (3-mo-old) that express the WRINKLED1 transcription factor and the ADP-glucose pyrophosphorylase RNAi relative to a wild type rutabaga plant. FIG. 4B graphically illustrates that the transgenic rutabaga plants ADP#1, ADP#2, ADP#3 and ADP#5 have more oil in there vegetative tissues than do wild type rutabaga. The amounts shown are nmoles oil per gram dry weight of plant material. FIG. 4C shows oil droplets (OD) formed in the transgenic rutabaga plants while FIG. 4D shows that substantially no oil droplets were formed in wild type rutabaga plants.

FIG. 5 A-B illustrates that *Arabidopsis* plants expressing the WRINKLED1 transcription factor and the ADP-glucose pyrophosphorylase RNAi are energy-rich fodder.

DETAILED DESCRIPTION

Figure 1:
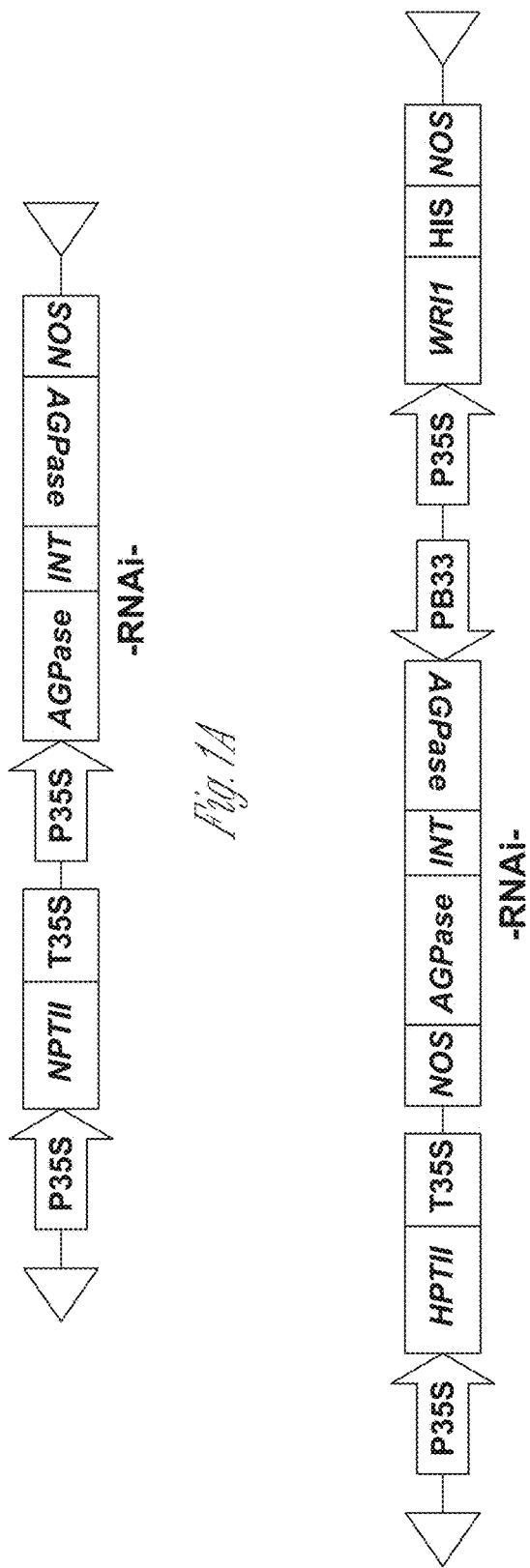
FIG. 1A-B are schematic representations of exemplary T-DNA binary vectors for expressing ADP-glucose pyrophosphorylase RNAi (FIG. 1A) and WRINKLED1 (WRI1.

The invention relates to plants that have been modified to produce more oil in their vegetative tissues, as well as methods of generating and using such plants or seedlings to turn sugar into oil. In general, the plants described herein have been modified to express increased levels of WRINKLED1 transcription factors and reduced levels of ADP-glucose pyrophosphorylase. Procedures like those described herein can be used for making plants with increased oil content in their vegetative tissues. Plants with increased oil content are useful as fodder for animals, as sources oil for human consumption, and as a source of oil for biofuels.

Plants that can be modified to produce more oil in vegetative tissues include food plants, vegetable oil plants, and plants useful for forage or fodder. Examples of plants and/or plant cells that can be modified as described herein include alfalfa (e.g., forage legume alfalfa), algae, avocado, barley, broccoli, Brussels sprouts, cabbage, canola, cassava, cauliflower, cole vegetables, collards, crucifers, grain legumes, grasses (e.g., forage grasses), jatropa, kale, kohlrabi, maize, miscanthus, mustards, nut sedge, oats, oil firewood trees, oilseeds, potato, radish, rice, rutabaga, sorghum, soybean, sugar beets, sugarcane, sunflower, switchgrass, tobacco, tomato, turnips, and wheat. In some embodiments, the plant is a *Brassicaceae* or other *Solanaceae* species. In some embodiments, the plant is not a species of *Arabidopsis*, for example, in some embodiments, the plant is not *Arabidopsis thaliana*.

ADP-Glucose Pyrophosphorylase

In bacteria and plants, the synthesis of glycogen and starch generally occurs by utilizing ADP-glucose as the glucosyl donor for elongation of the α-1,4-glucosidic chain. The main regulatory step takes place at the level of ADP-glucose synthesis, a reaction catalyzed by ADP-glucose pyrophosphorylase (AGPase). ADP-glucose pyrophosphorylase catalyses the first committed step of starch synthesis in plant tissues.

As described herein plants can be generated that express lower levels of ADP-glucose pyrophosphorylase, for example, by inhibiting the expression and/or translation of ADP-glucose pyrophosphorylase enzymes, especially in selected tissues and during selected parts of the plant life cycle.

ADP-glucose pyrophosphorylase is a heterotetrameric enzyme composed of two small and two large subunits. Amino acid and nucleic acid sequences for various ADP-glucose pyrophosphorylases, and their subunits, are available from the National Center for Biotechnology Information (NCBI) database (see, e.g., the website at ncbi.nlm.nih.gov).

For example, an amino acid sequence for a large subunit of a maize ADP-glucose pyrophosphorylase (*Zea mays*) is available as accession number CAA86227.1 (GI:558365), and is reproduced below as SEQ ID NO:1.

```
  1 MQFSSVLPLE GKACMSPVRR GSGGYGSERM RINCCSIRRN

41 KALRRMCFSA RGAVSSTQCV LTSDAGPDTL VRPNHPFRRN

61 YADPNEVAAV ILGGGTGTQL FPLTSTRATP AVPIGGCYRL

121 IDIPMSNCFN SGINKIFVMT QFNSASLNRH IHRTYLGGGI

161 NFTDGSVEVL AATQMPGEAA GWFQGTADAV RKFIWVLEDY

201 YKHKAIEHIL ILSGDQLYRM DYMELVQKHV DDNADITLSC

241 APVGESRASD YGLVKFDSSG RVIQFSEKPK GAALEEMKVD

281 TSFLNFATCT LPAEYPYIAS MGVYVFKRDV LLDLLKSRYA

321 ELHDFGSEIL PKALHEHNVQ AYVFTDYWED IGTIRSFFDA

361 NMALCEQPPK FEFYDPKTPF FTSPRYLPPT KSDKCRIKDA

401 IISHGCFLRE CAIEHSIVGV PSRLNSGCEL KNTMMMGADL
```

```
441 YETEDEISRL LAEGKVPIGV GENTKISNCI IDMNCQGWKE

481 RLHNKQRGRS KSPDRPGRRI LIRSGIVVVL KNATIKDGTV

521 I
```

A nucleic acid sequence for the above maize ADP-glucose pyrophosphorylase is available as accession number Z38111.1 (GI:558364), and is reproduced below as SEQ ID NO:2.

```
   1 GGCTCGCTCG CCTTCCTCCT CCCCACTCCA CTCCATTCCA

41 ACGCAACGCC TCGCCCCGCT TTATAGGCCG CCGCCCGCGC

81 CACATCGCCA CCGTCTCGCA CCGCCCGCGC CACCCATTCT

121 CTCTCGTCCA TCGCATCGCT CCGGCTCCCA GCGCAATCGA

161 TCCATCCGTC CCTAGGTGTG CTTCAGCTAT GCAGTTCAGC

201 AGCGTGCTTC CCCTAGAGGG AAAAGCGTGT ATGAGCCCAG

241 TGAGGAGAGG CAGTGGAGGT TATGGGAGTG AGAGGATGAG

281 GATCAACTGC TGCAGCATCA GGCGCAACAA GGCACTGAGG

321 AGGATGTGTT TCAGTGCAAG GGGTGCTGTG AGCAGCACGC

361 AGTGTGTGCT CACATCAGAT GCTGGCCCAG ACACTCTTGT

401 ACGTCCGAAC CATCCTTTTC GGAGGAATTA TGCTGATCCT

441 AATGAAGTCG CTGCCGTCAT TTTGGGTGGT GGTACCGGGA

481 CTCAGCTTTT CCCTCTCACA AGCACAAGGG CCGCCCGCGC

521 TGTTCCTATT GGAGGATGTT ACAGGCTTAT TGATATCCCC

561 ATGAGCAACT GTTTCAACAG TGGCATAAAC AAGATATTTG

601 TTATGACTCA GTTCAACTCA GCTTCTCTTA ACCGTCACAT

641 TCATCGTACC TATCTTGGTG GGGGGATCAA CTTCACTGAT

681 GGATCTGTTG AGGTGCTGGC TGCAACACAA ATGCCTGGGG

721 AGGCTGCTGG TTGGTTCCAG GGCACAGCAG ACGCCGTTAG

761 AAAATTTATC TGGGTACTTG AGGATTATTA CAAGCATAAA

801 GCTATAGAAC ACATTTTGAT TTTGTCAGGA GATCAACTCT

841 ATCGTATGGA TTACATGGAG CTTGTGCAGA AACATGTCGA

881 TGACAATGCA GACATAACTT TATCATGCGC TCCTGTTGGA

921 GAGAGTCGAG CATCTGACTA TGGATTAGTT AAGTTCGATA

961 GTTCAGGCCG TGTAATTCAG TTCTCTGAGA AACCAAAGGG

1001 TGCTGCCTTG GAAGAAATGA AAGTGGATAC CAGCTTCCTC

1041 AATTTCGCCA CTTGCACTCT CCCAGCTGAA TATCCCTATA

1081 TCGCTTCAAT GGGAGTTTAC GTTTTTAAGA GAGATGTTTT

1121 GTTAGACCTT CTAAAGTCAC GGTATGCTGA ACTGCATGAC

1161 TTTGGTTCTG AAATTCTGCC CAAGGCTTTG CATGAGCACA

1201 ATGTACAGGC ATATGTTTTC ACTGACTACT GGGAGGACAT

1241 TGGAACAATC AGATCTTTCT TTGATGCAAA CATGGCCCTC

1281 TGCGAGCAGC CTCCAAAGTT CGAGTTTTAC GATCCGAAAA

1321 CACCATTCTT CACTTCCCCT CGGTACTTGC CACCAACGAA

1361 GTCGGATAAG TGCAGGATTA AAGACGCGAT CATTTCACAC

1441 GGCTGCTTCT TGCGTGAGTG TGCCATCGAG CACTCTATTG

1441 TTGGTGTTCC GTCACGCCTA AACTCTGGAT GCGAGCTCAA

1481 GAATACCATG ATGATGGGTG CGGATTTGTA TGAGACCGAA

1521 GACGAGATCT CAAGGCTACT GGCAGAGGGC AAGGTGCCAA

1561 TTGGCGTAGG GGAGAACACG AAGATAAGCA ACTGCATCAT

1601 CGACATGAAT TGCCAGGGTT GGAAGGAACG TCTCCATAAC

1641 AAACAAAGAG GGCGTTCCAA GAGTCCCGAC CGGCCTGGAC

1681 GAAGGATACT AATCCGGTCT GGGATCGTGG TAGTCCTGAA

1721 GAACGCAACC ATCAAGGACG GCACCGTCAT ATAGAGACTA

1761 ACTTTGGCCT TACGCATGGC CTGCAAGGTT ACAGGTTAGT

1801 CATCGTCTTG AGAGTTGAGA CTTAGTTTGA GGCGCGCCCG

1841 ACCTTGACTT GAGCCGTCGG AGGGACAAGA ACATGAGGAA

1881 GAAGGGCTGG TGGTGCCGGA TGTTGCCATG GACGACGAGA

1921 AATGGTTTGG CTGGTCGCAT CGGTCCAGTA GCTAGCTCTT

1961 CCGATGTTAT TAATATATGT ATCTAGTGGA GTAGTGCGAA

2001 CAGTGCAATA AGCTGGGCGA GCAAAGCCGC GGCAACTCTT

2041 GGCTTGGGGA TTGGTTGGTG CATCTTGTAA ATAATAAACT

2081 CGGACGCAGC AAATGAAACA TGCCCCTCAT CTTCTTCCAA

2121 AAA
```

Related ADP-glucose pyrophosphorylase sequences can also be used in the methods described herein. For example, the following accession numbers provide amino acid sequences related to the SEQ ID NO:1 ADP-glucose pyrophosphorylase that can be employed in the methods described herein: CAA86227.1 GI:558365); P55234.1 (GI: 1707928); CAW47333.1 (GI:219752151); CAW63830.1 (GI:219764738).

Rapeseed (*Brassica napus*) is another species that can be modified as described herein to generate plants with increased vegetative oil. For example, the expression of the rapeseed ADP-glucose pyrophosphorylase can be reduced to divert more carbon into oil synthesis by the vegetative tissues of the rapeseed plant. Reduction of ADP-glucose pyrophosphorylase expression can be accomplished using procedures described herein, for example, by use of inhibitory nucleic acids that are complementary and/or homologous to ADP-glucose pyrophosphorylase nucleic acids.

One example of an amino acid sequence for a small subunit of a rapeseed (*Brassica napus*) ADP-glucose pyrophosphorylase is available as SEQ ID NO:3 and is provided below.

```
  1 DYEKFIQAHR ETDADITVAA LPMDEKRATA FGLMKIDDEG

41 RIIEFAEKPK GEQLKAMKVD TTILGLDDER AKEMPFIASM

81 GIYVVSKNVM LDLLRDQFPG ANDFGSEVIP GATDLGLRVQ

121 AYLYDGYWED IGTIEAFYNA NLGITKKPVP DFSFYDRSAP

141 IYTQPR
```

A nucleic acid sequence for the above rapeseed ADP-glucose pyrophosphorylase is available as accession number AJ271162, and is reproduced below as SEQ ID NO:4.

```
  1 GGACTACGAG AAGTTCATTC AAGCGCATCG TGAGACCGAC
 41 GCTGATATCA CTGTTGCTGC TCTTCCTATG GATGAGAAAC
 81 GTGCCACGGC TTTTGGACTT ATGAAGATTG ATGACGAAGG
121 AAGGATCATT GAGTTTGCTG AGAAGCCTAA AGGAGAGCAG
161 TTAAAGGCTA TGAAGGTTGA TACAACAATC TTGGGACTTG
201 ATGACGAAAG GGCCAAAGAG ATGCCCTTTA TTGCTAGTAT
241 GGGGATATAT GTTGTTAGCA AGAATGTGAT GTTGGACTTG
281 CTCCGAGACC AGTTCCCTGG AGCTAATGAC TTCGGGAGTG
321 AAGTTATCCC TGGTGCTACT GATCTTGGAC TCAGAGTGCA
361 AGCTTATCTG TATGATGGAT ACTGGGAAGA TATTGGTACC
401 ATTGAAGCCT TTTACAATGC TAATCTTGGG ATCACCAAGA
441 AACCAGTACC AGATTTCAGC TTCTATGACC GTTCAGCACC
481 AATCTACACA CAGCCTCGGT
```

In some embodiments, this above rapeseed ADP-glucose pyrophosphorylase is used for design of inhibitory nucleic acids to reduce ADP-glucose pyrophosphorylase enzyme levels. In other embodiments, this rapeseed ADP-glucose pyrophosphorylase is not used for design of inhibitory nucleic acids to reduce ADP-glucose pyrophosphorylase enzyme levels. For example, improved inhibition may be achieved by targeting the ADP-glucose pyrophosphorylase mRNA from the species of plant where inhibition is desired, rather than relying upon the rapeseed mRNA sequence.

Another example of an amino acid sequence for a large subunit of a rapeseed ADP-glucose pyrophosphorylase (*Brassica napus* subsp. *pekinensis*) is available as accession number AAK27685.1 (GI:13487711), and is reproduced below as SEQ ID NO:5.

```
  1 MVASPDCRIS LSAPSCLRGS SGYTKHIKLG SFCNGELMGK
 41 KLNLAQLRSS STNSSQKRIQ MSLNSVAGES KVQEIESEKR
 81 DPKTVASIIL GGGAGTRLFP LTKRRAKPAV PIGGAYRLID
121 VPMSNCINSG INKVYILTQY NSASLNRHLT RAYNSNGVFG
161 DGFVEALAAT QTPGETGKRW FQGTADAVRQ FHWLFEDARS
201 KEIEDVLILS GDHLYRMDYM DFVQDQSTKR RDISISCIPI
241 DDRECKRVQQ IHSKIMVSYK SLSVLHGRRA SDFGLMKIDD
281 KGRVISFSEK PKGDDLKAMA VDTTVLGLSK EEAEKKPYIA
321 SMGVYVFKKE ILLNLLRWRF PTANDFGSEI IPFSAKEFYV
361 NAYLFNDYWE DIGTIRSFFD ANLALTEHPP AFSFYDAAKP
401 IYTSRRNLPP SKIDGSKLID SIISHGSFLT NCLIEHSIVG
441 IRSRVGSNVQ LKDTVMLGAD FYETEAEVAA LLAEEKVPIG
481 IGENTKISSK TKRSLSNGLP SKQKVLDSFF PSHFPYRECI
521 IDKNARVGKN VVIANSEGVQ EADRSSDGFY IRSGITVILK
561 NSVIADGVVI
```

A nucleic acid sequence for the above large subunit of rapeseed ADP-glucose pyrophosphorylase is available as accession number AF347698.1 (GI: 13487710), and is reproduced below as SEQ ID NO:6.

```
   1 TTCGGCACGA GGCAACTCTC TTTTCTTCTC TGTTATCTCT
  41 CCACTTGTCT CAGAACTCTT CAACAGCCAA TATTTCCAGC
  81 AAAAATGGTT GCCTCTCCTG ACTGCAGAAT CTCCCTCTCT
 121 GCTCCGAGCT GCCTACGCGG CTCCTCGGGC TACACCAAGC
 161 ACATTAAGCT AGGAAGCTTC TGCAATGGGG AGCTCATGGG
 201 GAAGAAGCTT AACTTGGCTC AGCTTCGATC TTCTTCAACC
 241 AACTCCTCTC AAAAGAGAAT CCAAATGTCT TTAAACAGTG
 281 TAGCTGGAGA GAGTAAGGTA CAAGAAATTG AGTCTGAGAA
 321 AAGAGATCCA AAGCAAGGAG CTTCCATTAT TCTTGGAGGT
 361 GGAGCAGGAA CTCGACTCTT TCCTCTCACA AAGCGTCGCG
 401 CTAAGCCTGC TGTCCCTATC GGAGGAGCCT ATAGGTTGAT
 441 AGATGTACCG ATGAGCAACT GCATCAACAG TGGAATCAAC
 481 AAAGTCTACA TACTCACACA ATACAACTCA GCGTCACTGA
 521 ACAGGCATCT AACTCGTGCT TACAACTCCA ATGGAGTTTT
 561 TGGAGACGGC TTTGTTGAGG CTCTTGCAGC CACTCAAACG
 601 CCAGGAGAAA CAGGTAAAAG GTGGTTCCAA GGTACAGCAG
 641 ATGCGGTTCG GCAGTTCCAT TGGCTTTTTG AGGATGCAAG
 681 AAGCAAGGAG ATAGAGGATG TGTTGATCCT CTCTGGTGAT
 721 CACCTTTACA GGATGGATTA CATGGATTTT GTACAGGATC
 761 AGTCGACAAA GCGGCGAGAT ATAAGCATTT CCTGCATACC
 801 AATAGATGAC AGGGAATGCA AAAGAGTCCA ACAAATCCAT
 841 TCAAAGATCA TGGTTTCTTA TAAGTCTCTG TCTGTGTTAC
 881 ATGGTAGACG TGCTTCAGAT TTTGGTCTAA TGAAGATAGA
 921 TGACAAAGGA AGAGTCATCT CTTTCAGTGA AAAACCTAAA
 961 GGAGATGACC TGAAAGCAAT GGCAGTAGAC ACAACTGTTC
1001 TAGGACTTTC TAAGGAGGAA GCTGAAAAGA AACCATACAT
1041 AGCATCAATG GGAGTTTATG TTTTCAAGAA AGAAATACTG
1081 TTGAATCTCT TGAGATGGCG TTTCCCAACA GCAAACGACT
1121 TTGGTTCAGA GATTATACCC TTCTCAGCTA AAGAGTTCTA
1161 TGTGAATGCT TATCTCTTTA ATGACTACTG GGAAGATATA
1201 GGAACCATAA GATCTTTCTT TGATGCAAAT CTCGCCCTCA
1241 CTGAGCATCC ACCAGCATTC AGTTTCTACG ACGCAGCGAA
1281 ACCAATATAT ACATCAAGGA GAAACCTGCC ACCATCAAAG
1321 ATAGACGGCT CTAAGCTCAT TGATTCGATC ATTTCTCATG
1361 GAAGCTTCTT AACAAACTGC TTAATTGAGC ACAGCATTGT
1401 GGGAATTAGA TCAAGAGTAG GTAGTAATGT TCAGTTGAAG
1441 GACACTGTGA TGCTTGGGGC AGACTTCTAC GAAACTGAAG
1481 CAGAAGTTGC AGCACTACTT GCTGAGGAAA AAGTTCCCAT
```

-continued

```
1521 TGGAATAGGA GAGAACACAA AGATATCAAG TAAGACTAAA

1561 CGTTCACTTT CAAATGGTTT ACCTTCGAAA CAAAAGGTTC

1601 TTGATTCCTT TTTTCCTTCT CATTTCCCCT ACAGAGAATG

1641 CATTATAGAC AAGAATGCTA GAGTTGGCAA GAATGTAGTT

1681 ATAGCAAACT CAGAGGGAGT ACAAGAAGCA GATAGGTCAT

1721 CAGATGGATT TTACATCAGA TCTGGCATTA CAGTAATCTT

1761 GAAGAACTCA GTAATTGCAG ATGGAGTTGT CATATGAGAC

1801 TTTTAAGTCA AAACTATATT AATAAAAGCA ATTTATTTGA

1841 TAATAAAAAA AAAAAAAAA AA
```

Sequences related to this ADP-glucose pyrophosphorylase sequence can also be used in the methods described herein. For example, the following accession numbers provide amino acid sequences related to the ADP-glucose pyrophosphorylase nucleic acid with SEQ ID NO:6 that can be employed in the methods described herein:

| Accession No. | Species | % Identity |
|---|---|---|
| Y08728.1 | *P. sativum* mRNA for ADP-glucose pyrophosphorylase | 79% |
| XM_002311766.1 | *Populus trichocarpa* predicted protein, mRNA | 81% |
| AK321450.1 | *Solanum lycopersicum* cDNA, clone: LEFL1024DE07, HTC in leaf | 80% |
| XM_002281033.2 | PREDICTED: *Vitis vinifera* glucose-1-phosphate adenylyltransferase large subunit 1, chloroplastic-like (LOC100263079), mRNA | 80% |
| FQ395707.1 | *Vitis vinifera* clone SS0AFA14YI02 | 80% |
| FQ395157.1 | *Vitis vinifera* clone SS0AFA17YH17 | 80% |
| NM_001247048.1 | *Solanum lycopersicum* ADP-glucose pyrophosphorylase large subunit (agpL3), mRNA >gb|U85497.1|LEU85497 *Lycopersicon esculentum* ADP-glucose pyrophosphorylase large subunit (agpL3) mRNA, complete cds | 80% |
| XM_003606895.1 | *Medicago truncatula* Glucose-1-phosphate adenylyltransferase (MTR | 73% |

Thus, additional related ADP-glucose pyrophosphorylase sequences can be targeted or employed in the methods, seeds, plant cells, and plants described herein, including those with about at least 40% sequence identity, or at least 50% sequence identity, or at least 60% sequence identity, or at least 70% sequence identity, or 60-99% sequence identity, or 70-99% sequence identity, or 80-99% sequence identity, or 90-95% sequence identity, or 90-99% sequence identity, or 95-97% sequence identity, or 97-99% sequence identity, or 100% sequence identity (or complementarity) with any of SEQ ID NO:2, SEQ ID NO:4, SEQ ID NO:6.

WRINKLED

WRINKLED1 (WRI1) function appears to be needed for accumulation of triacylglycerols (TAGs) in *Arabidopsis* seeds. Overexpression of WRI1 may up-regulate a set of genes involved in fatty acid (FA) synthesis including, for example, genes for a subunit of pyruvate kinase (Pl-PKβ1), acetyl-CoA carboxylase (BCCP2), acyl carrier protein (ACP1), and ketoacyl-acyl carrier protein synthase (KAS1). WRI1 can bind to upstream sequences in such genes and may have a number of upstream binding sites. For example, some workers have observed that seven different WRI1 binding sites share a sequence [CnTnG](n)$_7$[CG], where n is any nucleotide designated as the AW-box (Maeo et al., *The Plant Journal* 60: 476-487 (2009)). WRI1 may facilitate synthesis of plant carbons into oil by activating genes involved in oil synthesis.

As described herein, WRINKLED1 is a transcription factor that can increase the synthesis of genes involved in oil synthesis. Modification of plants to express increased levels of WRINKLED1 transcription factors can increase the oil content of non-seed tissues (e.g., leaves, stalks and roots) in a variety of transgenic plants. Plants can be generated as described herein to include the following types of WRINKLED1 nucleic acids, especially WRINKLED1 nucleic acids that are operably linked to control sequences that optimize the synthesis of oil by providing WRINKLED1 expression in selected tissues and during selected parts of the plant life cycle.

One example of an amino acid sequence for a WRINKLED1 (WRI1) sequence (*Brassica napus*) is available as accession number ADO 16346 1 (GI:308193634), and is reproduced below as SEQ ID NO:7.

```
  1 MKRPLTTSPS TSSSTSSSAC ILPTQPETPR PKRAKRAKKS

41 SIPTDVKPQN PTSPASTRRS SIYRGVTRHR WTGRYEAHLW

81 DKSSWNSIQN KKGKQVYLGA YDSEEAAAHT YDLAALKYWG

121 PDTILNFPAE TYTKELEEMQ RCTKEEYLAS LRRQSSGFSR

161 GVSKYRGVAR HHHNGRWEAR IGRVFGNKYL YLGTYNTQEE

201 AAAAYDMAAI EYRGANAVTN FDISNYIDRL KKKGVFPFPV

241 SQANHQEAVL AEAKQEVEAK EEPTEEVKQC VEKEEPQEAK

281 EEKTEKKQQQ QEVEEAVVTC CIDSSESNEL AWDFCMMDSG

301 FAPFLTDSNL SSENPIEYPE LFNEMGFEDN IDFMFEEGKQ

361 DCLSLENLDC CDGVVVVGRE SPTSLSSSPL SCLSTDSASS

401 TTTTTITSVS CNYSV
```

A nucleic acid sequence for the above *Brassica napus* WRIJ nucleic acid sequence is available as accession number HM370542.1 (GI:308193633), and is reproduced below as SEQ ID NO:8.

```
  1 AGGAAGCAGC CCTTAACCAC TTCTCCTTCT ACCTCCTCTT

41 CTACTTCTTC TTCGGCTTGT ATACTTCCGA CTCAACCAGA

61 GACTCCAAGG CCCAAACGAG CCAAAGGGC TAAGAAATCT

121 TCTATTCCTA CTGATGTTAA ACCACAGAAT CCCACCAGTC

161 CTGCCTCCAC CAGACGCAGC TCTATCTACA GAGGAGTCAC

201 TAGACATAGA TGGACAGGGA GATACGAGGC TCATCTATGG

241 GACAAAAGCT CGTGGAATTC GATTCAGAAC AAGAAAGGCA

281 AACAAGTTTA TCTGGGAGCA TATGACAGCG AGGAAGCAGC

321 AGCGCATACG TACGATCTAG CTGCTCTCAA GTACTGGGGT

361 CCCGACACCA TCTTGAACTT TCCGGCTGAG ACAACAACAA

401 AGGAGTTGGA GGAGATGCAG AGATGTACAA AGGAAGAGTA

441 TTTGGCTTCT CTCCGCCGCC AGAGCAGTGG TTTCTCTAGA
```

```
481 GGCGTCTCTA AATATCGCGG CGTCGCCAGG CATCACCATA

521 ACGGAAGATG GGAAGCTAGG ATTGGAAGGG TGTTTGGAAA

541 CAAGTACTTG TACCTCGGCA CTTATAATAC GCAGGAGGAA

601 GCTGCAGCTG CATATGACAT GGCGGCTATA GAGTACAGAG

641 GCGCAAACGC AGTGACCAAC TTCGACATTA GTAACTACAT

681 CGACCGGTTA AAGAAAAAAG GTGTCTTCCC ATTCCCTGTG

721 AGCCAAGCCA ATCATCAAGA AGCTGTTCTT GCTGAAGCCA

761 AACAAGAAGT GGAAGCTAAA GAAGAGCCTA CAGAAGAAGT

801 GAAGCAGTGT GTCGAAAAAG AAGAACCGCA AGAAGCTAAA

841 GAAGAGAAGA CTGAGAAAAA ACAACAACAA CAAGAAGTGG

881 AGGAGGCGGT GGTCACTTGC TGCATTGATT CTTCGGAGAG

921 CAATGAGCTG GCTTGGGACT TCTGTATGAT GGATTCAGGG

961 TTTGCTCCGT TTTTGACGGA TTCAAATCTC TCGAGTGAGA

1001 ATCCCATTGA GTATCCTGAG CTTTTCAATG AGATGGGGTT

1041 TGAGGATAAC ATTGACTTCA TGTTCGAGGA AGGGAAGCAA

1081 GACTGCTTGA GCAGGAGGAA TCTGGATTGT TGCGATGGTG

1121 TTGTTGTGGT GGGAAGAGAG AGCCCAACTT CATTGTCGTC

1161 TTCACCGTTG TCTTGCTTGT CTACTGACTC TGCTTCATCA

1201 ACAACAACAA CAACAATAAC CTCTGTTTCT TGTAACTATT

1241 CTGTCTGA
```

Another example of an amino acid sequence for a WRINKLED1 (WRI1) sequence (*Brassica napus*) is available as accession number ABD16282.1 (GI:87042570), and is reproduced below as SEQ ID NO:9.

```
  1 MKRPLTTSPS SSSSTSSSAC ILPTQSETPR PKRAKRAKKS

41 SLRSDVKPQN PTSPASTRRS SIYRGVTRHR WTGRYEAHLW

81 DKSSWNSIQN KKGKQVYLGA YDSEEAAAHT YDLAALKYWG

121 PNTILNFPVE TYTKELEEMQ RCTKEEYLAS LRRQSSGFSR

161 GVSKYRGVAR HHHNGRWEAR IGRVFGNKYL YLGTYNTQEE

201 AAAAYDMAAI EYRGANAVTN FDIGNYIDRL KKKGVFPFPV

241 SQANHQEAVL AETKQEVEAK EEPTEEVKQC VEKEEAKEEK

281 TEKKQQQEVE EAVITCCIDS SESNELAWDF CMMDSGFAPF

321 LTDSNLSSEN PIEYPELFNE MGFEDNIDFM FEEGKQDCLS

361 LENLDCCDGV VVVGRESPTS LSSSPLSCLS TDSASSTTTT

401 ATTVTSVSWN YSV
```

A nucleic acid sequence for the above *Brassica napus* WRI1 nucleic acid sequence is available as accession number DQ370141.1 (GI:87042569), and is reproduced below as SEQ ID NO:10.

```
  1 AGGAAGCAGC CCTTAACCAC TTCTCCTTCT TCCTCCTCTT

41 CTACTTCTTC TTCGGCCTGT ATACTTCCGA CTCAATCAGA

61 GACTCCAAGG CCCAAACGAG CCAAAAGGGC TAAGAAATCT

121 TCTCTGCGTT CTGATGTTAA ACCACAGAAT CCCACCAGTC

161 CTGCCTCCAC CAGACGCAGC TCTATCTACA GAGGAGTCAC

181 TAGACATAGA TGGACAGGGA GATACGAAGC TCATCTATGG

241 GACAAAAGCT CGTGGAATTC GATTCAGAAC AAGAAAGGCA

281 AACAAGTTTA TCTGGGAGCA TATGACAGCG AGGAAGCAGC

321 AGCACATACG TACGATCTAG CTGCTCTCAA GTACTGGGGT

361 CCCAACACCA TCTTGAACTT TCCGGTTGAG ACGTACACAA

401 AGGAGCTGGA GGAGATGCAG AGATGTACAA AGGAAGAGTA

441 TTTGGCTTCT CTCCGCCGCC AGAGCAGTGG TTTCTCTAGA

481 GGCGTCTCTA AATATCGCGG CGTCGCCAGG CATCACCATA

521 ATGGAAGATG GGAAGCTCGG ATTGGAAGGG TGTTTGGAAA

541 CAAGTACTTG TACCTCGGCA CCTATAATAC GCAGGAGGAA

601 GCTGCAGCTG CATATGACAT GGCGGCTATA GAGTACAGAG

641 GTGCAAACGC AGTGACCAAC TTCGACATTG GTAACTACAT

681 CGACCGGTTA AAGAAAAAAG GTGTCTTCCC GTTCCCCGTG

721 AGCCAAGCTA ATCATCAAGA AGCTGTTCTT GCTGAAACCA

761 AACAAGAAGT GGAAGCAAGA GAAGAGCCTA CAGAAGAAGT

801 GAAGCAGTGT GTCGAAAAAG AAGAAGCTAA AGAAGAGAAG

841 ACTGAGAAAA ACAACAACA AGAAGAGAAG GAGGCGGTGA

881 TCACTTGCTG CATTGATTCT TCAGAGAGCA ATGAGCTGGC

921 TTGGGACTTC TGTATGATGG ATTCAGGGTT TGCTCCGTTT

961 TTGACTGATT CAAATCTCTC GAGTGAGAAT CCCATTGAGT

1001 ATCCTGAGCT TTTCAATGAG ATGGGTTTTG AGGATAACAT

1041 TGACTTCATG TTCGAGGAAG GGAAGCAAGA CTGCTTGAGC

1081 TTGGAGAATC TTGATTGTTG CGATGGTGTT GTTGTGGTGG

1121 GAAGAGAGAG CCCAACTTCA TTGTCGTCTT CTCCGTTGTC

1141 CTGCTTGTCT ACTGACTCTG CTTCATCAAC AACAACAACA

1201 GCAACAACAG TAACCTCTGT TCTTGGAAC TATTCTGTCT

1241 GA
```

Another example of an amino acid sequence for a WRINKLED1 (WRI1) sequence (*Brassica napus*) is available as accession number ABD72476.1 (GI:89357185), and is reproduced below as SEQ ID NO:11.

```
  1 MKRPLTTSPS SSSSTSSSAC ILPTQSETPR PKRAKRAKKS

41 SLRSDVKPQN PTSPASTRRS SIYRGVTRHR WTGRYEAHLW

61 DKSSWNSIQN KKGKQVYLGA YDSEEAAAHT YDLAALKYWG

121 PNTILNFPVE TYTKELEEMQ RCTKEEYLAS LRRQSSGFSR

161 GVSKYRGVAR HHHNGRWEAR IGRVFGNKYL YLGTYNTQEE

201 AAAAYDMAAI EYRGANAVTN FDIGNYIDRL KKKGVFPFPV

241 SQANHQEAVL AETKQEVEAK EEPTEEVKQC VEKEEAKEEK

281 TEKKQQQEVE EAVITCCIDS SESNELAWDF CMMDSGFAPF
```

301 LTDSNLSSEN PIEYPELFNE MGFEDNIDFM FEEGKQDCLS
361 LENLDCCDGV VVVGRESPTS LSSSPLSCLS TDSASSTTTT
401 ATTVTSVSWN YSV

A nucleic acid sequence for the above *Brassica napus* WRIJ nucleic acid sequence is available as accession number DQ402050.1 (GI:89357184), and is reproduced below as SEQ ID NO:12.

```
   1 ATGAAGAGAC CCTTAACCAC TTCTCCTTCT TCCTCCTCTT
  41 CTACTTCTTC TTCGGCCTGT ATACTTCCGA CTCAATCAGA
  81 GACTCCAAGG CCCAAACGAG CCAAAAGGGC TAAGAAATCT
 121 TCTCTGCGTT CTGATGTTAA ACCACAGAAT CCCACCAGTC
 161 CTGCCTCCAC CAGACGCAGC TCTATCTACA GAGGAGTCAC
 201 TAGGTTGAGA AAAATAAAAT AAAATGATTG ATTCTTTTAG
 241 ATTTGATTTG GGTTATGTTT TTTTTTTTTT TTTTTCTAAA
 281 CTGCATTTCG ATTGCATGTT ACAGACATAG ATGGACAGGG
 321 AGATACGAAG CTCATCTATG GACAAAAGC TCGTGGAATT
 361 CGATTCAGAA CAAGAAGGC AAACAAGGTT CTTAATTTTT
 401 ACAAAAAACC CATCTTGATT CTGTAATAAA GATCTGGCCT
 441 TTTTTTTGTT TTGTTTTAAT CTGATTTTGG TTTCTGTTGT
 481 TTGATCTCAA CCTCACTGCC TCACTCTGCG CCTTGTTCTT
 521 CTACTCATCA GTTTATCTGG GTAATTTTTT TAATTGAGAA
 541 ATTAAAAGA GTTTGATTTG GTCAAGAGGA TGAACGAATG
 601 GAATCTCAAC TGCTCTGACG CCGTAATTGC AGGAGCATAT
 641 GACAGCGAGG AAGCAGCAGC ACATACGTAC GATCTAGCTG
 681 CTCTCAAGTA CTGGGGTCCC AACACCATCT TGAACTTTCC
 721 GGTAAGAAAA AATAACTTGA TTGATTGATT GATGCATGTT
 761 TGTTCTTGTT GAATTAATTA AAAAAAATGA TCCAAACAGG
 781 TTGAGACGTA CACAAAGGAG CTGGAGGAGA TGCAGAGATG
 841 TACAAAGGAA GAGTATTTGG CTTCTCTCCG CCGCCAGAGC
 881 AGTGGTTTCT CTAGAGGCGT CTCTAAATAT CGCGGCGTCG
 921 CCAGGTTCTC TCTTTTTTCT TTTTCTTTAA TTACGTGTTT
 961 GTTTTTAATT TGATTTGGTA AATTAATTAC ACCAAAATCA
1001 GGAATTAAAT TTTCCTTTTC CGCATTTTTT GAAAAATTAA
1041 TTAATAGGGT GGTGACTAAG AAAAAGAAAA CAAAATAGGA
1081 AATGTGATTT TTTGGAAATT AAAAAAGCTG GACTTTTCA
1121 TAAGATTTGC TTTTAGAATT TTTATCTCTC TCTCTCTCTC
1161 TATCATAATT AACTTTTGTT TAAGTACTTG TCCTGCAATT
1201 GAGATGTTTA TTGTAATTTG TAAATATGTG ATAGCTATAG
1241 CTTGATTTTC GCAAATGATT CATTTATCAA ACATTTTTTG
1281 TTATTTCTTT CCCATTTTAT ATTCTGAAAA AACAAGAAA
1321 GTAATAAAAA TTGCAAATTA TGGGAAAACA GGCATCACCA
1361 TAATGGAAGA TGGGAAGCTC GGATTGGAAG GGTGTTTGGA
1401 AACAAGTACT TGTACCTCGG CACCTATAGT ACGTACATCC
1441 TTGACTCTTT ATTCTTAAAT AATAAATTGT TTAAATAAT
1481 ATCAGATTAA TTTTTAAAAA AATTTAAGAA TCATTATCGT
1501 AATCGAATAT TTACAAGGGC ATAACGGATC CTTTAAAAAC
1561 AAAAACTACT CTGGTATTTG ATTTGAAAAT AGATATTACA
1601 ATGTTTTGAG TTAGTTTATA CTTTATACTA CTATTTTCTA
1641 CGAGTTTTAT ATTATACTTG TGATTAAGCA ATAATTATT
1681 TGTTTAGTTG GTCAATTAGA ATAAACATAA TGGGGAGGCA
1721 GTGAGTGGGG GTTTACACAC TCACGTGAGA CGAGAGTTTT
1761 GACATCATGT CCCCTCACTT CATACTAATT GATTTTTATC
1801 TTTAATATCA GCATTTTCAG AGTATTATTT AACTATCTGA
1841 CCCCTGCATA ATTACCTTTT AAATTCTGCA TTTTGTGGAT
1881 CCAATACTCT GAACACGAAA ATTAAAAACT CTGCAGAAGG
1921 GAATATTAAC ACCAACTCTT TACTGAAAAG TAATACTACC
1961 CTTTTTCAAT TCTTTTGATC GGGTCCTTAG GTTATTAATG
2001 GATCTTACTT TGAAAAAAA AAACAAGTTA CAAAAAATTC
2041 AAGATGTTTT TAGAGTTTCT CGGATTCAGT TTTGCAAAAA
2081 TATAGGCAGT GTTATAACAA AAGGGCACAT ATTATTCAGA
2121 TTTTATTTTT TTAAAAGAAA AAAATAGGAG AGCCAGGAGC
2161 ATAATAACAA AAAAATGAAA GTAGTAGATG TGAATAAATG
2201 TATAGAATAA TGTAACGTTA CAAGTGTAAA GGCGCGTGTA
2241 GCGCGTAGCT CACGTGGTAA CACTCTCCTC TCACTTCATA
2281 AAAAGGACAA ATTAGTTCAG AAGGGCTAGG ACCAAACCCG
2321 AGGTCGATCT GGTCTACTTT TTTTTGTTTG GGTGGTGGTT
2361 CATTAAAGAA TGGTTTTAAG AGTTGAGTCT GTTCTCAGTA
2401 GCAGTCACGA GCCCTCACGT GCATGTTTCA TCTCTCTCTC
2441 TCTCTACCAT ATCTTTCATC TTGTCCTCAG GAACAAAATC
2481 TGGTCTGCTT TATTTTTAAA TGCAAATTAT TGTCTTCATA
2521 TTTATTATGT AAACTATGAA GTTAATAGTG ATAGTTATTA
2561 CGTATTAGGA GCTTAGAGTT GACACTAGGT TGGTATTTTT
2601 ATTTGCTAAC TAGTCAGTAA TTGTACGTTC GTGTAATTAT
2641 TTATATATTG TTGCATTTGT TTAAGCTACA AACTTGGACT
2681 CTTTTTAGCG TTTAGAGCGG CGGAGAGTGG AGTAGAAATG
2721 GTCTCGTCCA CGCCTCAACT CTATACGCAT CTCACACACC
2761 TATAGTGTAA CCCTAGTTGT CCCCACTAAC ACGTCACCTA
2801 ATTCCCTTTG GTTTTTGTC TTTATTAGGC ATCTTAAAAT
2841 TCTAAAAATA AAATATTAAA ATACATACTG AAACACATGT
2881 TTGGTGAAGT AACACAAACA ATTATGTGAA AACTGTTACT
2921 TTCAAAACAC GCTGACTTTG TTTGGTTGTG CAGATACGCA
```

-continued

```
2961 GGAGGAAGCT GCAGCTGCAT ATGACATGGC GGCTATAGAG

3001 TACAGAGGTG CAAACGCAGT GACCAACTTC GACATTGGTA

3041 ACTACATCGA CCGGTTAAAG AAAAAAGGTG TCTTCCCGTT

3081 CCCCGTGAGC CAAGCTAATC ATCAAGAAGC TGTTCTTGCT

3121 GAAACCAAAC AAGAAGTGGA AGCTAAAGAA GAGCCTACAG

3161 AAGAAGTGAA GCAGTGTGTC GAAAAAGAAG AAGCTAAAGA

3201 AGAGAAGACT GAGAAAAAAC AACAACAAGA AGTGGAGGAG

3241 GCGGTGATCA CTTGCTGCAT TGATTCTTCA GAGAGCAATG

3281 AGCTGGCTTG GGACTTCTGT ATGATGGATT CAGGGTTTGC

3321 TCCGTTTTTG ACTGATTCAA ATCTCTCGAG TGAGAATCCC

3361 ATTGAGTATC CTGAGCTTTT CAATGAGATG GGTTTTGAGG

3401 ATAACATTGA CTTCATGTTC GAGGAAGGGA AGCAAGACTG

3441 CTTGAGCTTG GAGAATCTTG ATTGTTGCGA TGGTGTTGTT

3481 GTGGTGGGAA GAGAGAGCCC AACTTCATTG TCGTCTTCTC

3521 CGTTGTCCTG CTTGTCTACT GACTCTGCTT CATCAACAAC

3561 AACAACAGCA ACAACAGTAA CCTCTGTTTC TTGGAACTAT

3601 TCTGTCTGA
```

Another example of an amino acid sequence for a WRINKLED1 (WRIJ) sequence (*Arabidopsis thaliana*) is available as accession number AAP80382.1 (GI:32364685), and is reproduced below as SEQ ID NO:13.

```
  1 MKKRLTTSTC SSSPSSSVSS STTTSSPIQS EAPRPKRAKR

41 AKKSSPSGDK SHNPTSPAST RRSSIYRGVT RHRWTGRFEA

81 HLWDKSSWNS IQNKKGKQVY LGAYDSEEAA AHTYDLAALK

121 YWGPDTILNF PAETYTKELE EMQRVTKEEY LASLRRQSSG

161 FSRGVSKYRG VARHHHNGRW EARIGRVFGN KYLYLGTYNT

201 QEEAAAAYDM AAIEYRGANA VTNFDISNYI DRLKKKGVFP

241 FPVNQANHQE GILVEAKQEV ETREAKEEPR EEVKQQYVEE

281 PPQEEEEKEE EKAEQQEAEI VGYSEEAAVV NCCIDSSTIM

301 EMDRCGDNNE LAWNFCMMDT GFSPFLTDQN LANENPIEYP

361 ELFNELAFED NIDFMFDDGK HECLNLENLD CCVVGRESPP

401 SSSSPLSCLS TDSASSTTTT TTSVSCNYLV
```

A nucleic acid sequence for the above *Arabidopsis thaliana* WRIJ nucleic acid sequence is available as accession number AY254038.2 (GI:51859605), and is reproduced below as SEQ ID NO:14.

```
  1 AAACCACTCT GCTTCCTCTT CCTCTGAGAA ATCAAATCAC

41 TCACACTCCA AAAAAAAATC TAAACTTTCT CAGAGTTTAA

81 TGAAGAAGCT CTTAACCACT TCCACTTGTT CTTCTTCTCC

121 ATCTTCCTCT GTTTCTTCTT CTACTACTAC TTCCTCTCCT

161 ATTCAGTCGG AGGCTCCAAG GCCTAAACGA GCCAAAAGGG

201 CTAAGAAATC TTCTCCTTCT GGTGATAAAT CTCATAACCC
```

-continued

```
241 GACAAGCCCT GCTTCTACCC GACGCAGCTC TATCTACAGA

281 GGAGTCACTA GACATAGATG GACTGGGAGA TTCGAGGCTC

301 ATCTTTGGGA CAAAAGCTCT TGGAATTCGA TTCAGAACAA

361 GAAAGGCAAA CAAGTTTATC TGGGAGCATA TGACAGTGAA

401 GAAGCAGCAG CACATACGTA CGATCTGGCT GCTCTCAAGT

421 ACTGGGGACC CGACACCATC TTGAATTTTC CGGCAGAGAC

481 GTACACAAAG GAATTGGAAG AAATGCAGAG AGTGACAAAG

521 GAAGAATATT TGGCTTCTCT CCGCCGCCAG AGCAGTGGTT

581 TCTCCAGAGG CGTCTCTAAA TATCGCGGCG TCGCTAGGCA

601 TCACCACAAC GGAAGATGGG AGGCTCGGAT CGGAAGAGTG

641 TTTGGGAACA AGTACTTGTA CCTCGGCACC TATAATACGC

681 AGGAGGAAGC TGCTGCAGCA TATGACATGG CTGCGATTGA

721 GTATCGAGGC GCAAACGCGG TTACTAATTT CGACATTAGT

761 AATTACATTG ACCGGTTAAA GAAGAAAGGT GTTTTCCCGT

801 TCCCTGTGAA CCAAGCTAAC CATCAAGAGG GTATTCTTGT

841 TGAAGCCAAA CAAGAAGTTG AAACGAGAGA AGCGAAGGAA

881 GAGCCTAGAG AAGAAGTGAA ACAACAGTAC GTGGAAGAAC

921 CACCGCAAGA AGAAGAAGAG AAGGAAGAAG AGAAAGCAGA

961 GCAACAAGAA GCAGAGATTG TAGGATATTC AGAAGAAGCA

1001 GCAGTGGTCA ATTGCTGCAT AGACTCTTCA ACCATAATGG

1041 AAATGGATCG TTGTGGGGAC AACAATGAGC TGGCTTGGAA

1081 CTTCTGTATG ATGGATACAG GGTTTTCTCC GTTTTTGACT

1121 GATCAGAATC TCGCGAATGA AATCCCATA GAGTATCCGG

1141 AGCTATTCAA TGAGTTAGCA TTTGAGGACA ACATCGACTT

1201 CATGTTCGAT GATGGGAAGC ACGAGTGCTT GAACTTGGAA

1241 AATCTGGATT GTTGCGTGGT GGGAAGAGAG AGCCCACCCT

1281 CTTCTTCTTC ACCATTGTCT TGCTTATCTA CTGACTCTGC

1321 TTCATCAACA ACAACAACAA CAACCTCGGT TTCTTGTAAC

1361 TATTTGGTCT GAGAGAGAGA GCTTTGCCTT CTAGTTTGAA

1401 TTTCTATTTC TTCCGCTTCT TCTTCTTTTT TTTCTTTTGT

1441 TGGGTTCTGC TTAGGGTTTG TATTTCAGTT TCAGGGCTTG

1481 TTCGTTGGTT CTGAATAATC AATGTCTTTG CCCCTTTTCT

1501 AATGGGTACC TGAAGGGCGA
```

In some embodiments, primers are selected from the SEQ ID NO: 14 nucleic acid sequences. Such primers can be used to identify and/or isolate WRINKLED1 nucleic acids from other species, for example, by hybridization, polymerase chain reaction, reverse transcription, and combinations of these and other methods. For example, a forward primer spanning nucleotides 56 to 75 of the SEQ ID NO:14 nucleic acid can have the following sequence, or be complementary to the following sequence (SEQ ID NO:15):

```
AAATCTAAAC TTTCTCAGAG.
```

A reverse primer spanning nucleotides 1471 to 1512 of the SEQ ID NO:14 sequence can have the following sequence, or be complementary to the following sequence (SEQ ID NO:16):

```
TCAGGGCTTG TTCGTTGGTT CTGAATAATC AATGTCTTTG CC.
```

Another example of an amino acid sequence for a WRINKLED1 (WRIJ) sequence (*Arabidopsis thaliana*) is available as accession number NP_974430.1 (GI: 42572669), and is reproduced below as SEQ ID NO:17.

```
  1 MDWEIRGSSL GQKLLEFDSE QERQTRFRAY DSEEAAAHTY
 41 DLAALKYWGP DTILNFPAET YTKELEEMQR VTKEEYLASL
 81 RRQSSGFSRG VSKYRGVARH HHNGRWEARI GRVFGNKYLY
121 LGTYNTQEEA AAAYDMAAIE YRGANAVTNF DISNYIDRLK
161 KKGVFPFPVN QANHQEGILV EAKQEVETRE AKEEPREEVK
181 QQYVEEPPQE EEEKEEEKAE QQEAEIVGYS EEAAVVNCCI
241 DSSTIMEMDR CGDNNELAWN FCMMDTGFSP FLTDQNLANE
281 NPIEYPELFN ELAFEDNIDF MFDDGKHECL NLENLDCCVV
301 GRESPPSSSS PLSCLSTDSA SSTTTTTTSV SCNYLV
```

A nucleic acid sequence for the above *Arabidopsis thaliana* WRIJ nucleic acid sequence is available as accession number NM_202701.2 (GI:145362489), and is reproduced below as SEQ ID NO:18.

```
   1 CAGGGTTTAT TTAACTTGCC CTTTCTCGTT TCCTCCTTTT
  41 TTTCTTAAAC CACTCTGCTT CCTCTTCCTC TGAGAAATCA
  81 AATCACTCAC ACTCCAAAAA AAAATCTAAA CTTTCTCAGA
 121 GTTTAATGAA GAAGCGCTTA ACCACTTCCA CTTGTTCTTC
 161 TTCTCCATCT TCCTCTGTTT CTTCTTCTAC TACTACTTCC
 201 TCTCCTATTC AGTCGGAGGC TCCAAGGCCT AAACGAGCCA
 241 AAAGGGCTAA GAAATCTTCT CCTTCTGGTG ATAAATCTCA
 281 TAACCCGACA AGCCCTGCTT CTACCCGACG CAGCTCTATC
 301 TACAGAGGAG TCACTAGACA TAGATGGACT GGGAGATTCG
 361 AGGCTCATCT TTGGGACAAA AGCTCTTGGA ATTCGATTCA
 401 GAACAAGAAA GGCAAACAAG GTTTCGAGCA TATGACAGTG
 441 AAGAAGCAGC AGCACATACG TACGATCTGG CTGCTCTCAA
 481 GTACTGGGGA CCCGACACCA TCTTGAATTT TCCGGCAGAG
 521 ACGTACACAA AGGAATTGGA AGAAATGCAG AGAGTGACAA
 581 AGGAAGAATA TTTGGCTTCT CTCCGCCGCC AGAGCAGTGG
 601 TTTCTCCAGA GGCGTCTCTA AATATCGCGG CGTCGCTAGG
 641 CATCACCACA ACGGAAGATG GGAGGCTCGG ATCGGAAGAG
 681 TGTTTGGGAA CAAGTACTTG TACCTCGGCA CCTATAATAC
 721 GCAGGAGGAA GCTGCTGCAG CATATGACAT GGCTGCGATT
 761 GAGTATCGAG GCGCAAACGC GGTTACTAAT TTCGACATTA
 801 GTAATTACAT TGACCGGTTA AAGAAGAAAG GTGTTTTCCC
 841 GTTCCCTGTG AACCAAGCTA ACCATCAAGA GGGTATTCTT
 881 GTTGAAGCCA AACAAGAAGT TGAAACGAGA GAAGCGAAGG
 921 AAGAGCCTAG AGAAGAAGTG AAACAACAGT ACGTGGAAGA
 961 ACCACCGCAA GAAGAAGAAG AGAAGGAAGA AGAAAAGCA
1001 GAGCAACAAG AAGCAGAGAT TGTAGGATAT TCAGAAGAAG
1041 CAGCAGTGGT CAATTGCTGC ATAGACTCTT CAACCATAAT
1081 GGAAATGGAT CGTTGTGGGG ACAACAATGA GCTGGCTTGG
1121 AACTTCTGTA TGATGGATAC AGGGTTTTCT CCGTTTTTGA
1161 CTGATCAGAA TCTCGCGAAT GAGAATCCCA TAGAGTATCC
1201 GGAGCTATTC AATGAGTTAG CATTTGAGGA CAACATCGAC
1241 TTCATGTTCG ATGATGGGAA GCACGAGTGC TTGAACTTGG
1281 AAAATCTGGA TTGTTGCGTG GTGGGAAGAG AGAGCCCACC
1321 CTCTTCTTCT TCACCATTGT CTTGCTTATC TACTGACTCT
1361 GCTTCATCAA CAACAACAAC AACAACCTCG GTTTCTTGTA
1401 ACTATTTGGT CTGAGAGAGA GAGCTTTGCC TTCTAGTTTG
1441 AATTTCTATT TCTTCCGCTT CTTCTTCTTT TTTTTCTTTT
1481 GTTGGGTTCT GCTTAGGGTT TGTATTTCAG TTTCAGGGCT
1521 TGTTCGTTGG TTCTGAATAA TCAATGTCTT TGCCCCTTTT
1561 CTAATGCTCC AAGTTCAGAT
```

Sequences related to the WRINKLED1 sequences provided herein can also be used in the methods and plants provided herein. For example, the following protein sequences exhibit sequence identity to the *Brassica napus* WRINKELD amino acid sequence with SEQ ID NO:7.

| Accession | Description | Sequence Identity |
|---|---|---|
| ADO16346.1 | WRINKLED1 1 [*Brassica napus*] | 100% |
| ABD16282.1 | AP2/EREBP transcription factor [*Brassica napus*] >gb\|ABD72476.1\| AP2/EREBP transcriptional factor WRI1 [*Brassica napus*] | 94% |
| AAT44955.1 | putative AP2/EREBP transcription factor [*Arabidopsis thaliana*] | 93% |
| CAB81797.1 | aintegumaenta-like protein [*Arabidopsis thaliana*] | 91% |
| XP_002876251.1 | hypothetical protein ARALYDRAFT_485830 [*Arabidopsis lyrata* subsp. *lyrata*] >gb\|EFH52510.1\| hypothetical protein | 82% |

-continued

| Accession | Description | Sequence Identity |
|---|---|---|
| NP_001030857.1 | ARALYDRAFT_485830 [*Arabidopsis lyrata* subsp. *lyrata*] ethylene-responsive transcription factor WRI1 [*Arabidopsis thaliana*] >sp|Q6X5Y6.1|WRI1_ARATH RecName: Full = Ethylene-responsive transcription factor WRI1; AltName: Full = Protein ACTIVATOR OF SPORAMIN::LUC 1; AltName: Full = Protein WRINKLED1 1 >gb|AAP80382.1 WRINKLED1 [*Arabidopsis thaliana*] >gb|AAX11223.1| activator of sporamin LUC 1 [*Arabidopsis thaliana*] >gb|AEE79215.1| ethylene-responsive transcription factor WRI1 [*Arabidopsis thaliana*] | 81% |
| NP_191000.3 | ethylene-responsive transcription factor WRI1 [*Arabidopsis thaliana*] >gb|AEE79213.1| ethylene-responsive transcription factor WRI1 [*Arabidopsis thaliana*] | 81% |
| XP_002966660.1 | hypothetical protein SELMODRAFT_85823 [*Selaginella moellendorffii*] >gb|EFJ32687.1| hypothetical protein SELMODRAFT_85823 [*Selaginella moellendorffii*] | 80% |
| XP_002528384.1 | conserved hypothetical protein [*Ricinus communis*] >gbEEF33977.1 conserved hypothetical protein [*Ricinus communis*] | 80% |
| NP_001061917.1 | Os08g0442400 [*Oryza sativa Japonica* Group] >dbj|BAF23831.1| Os08g0442400 [*Oryza sativa Japonica* Group] >dbj|BAG97826.1| unnamed protein product [*Oryza sativa Japonica* Group] >gb|ADX60232.1 AP2-EREBP transcription factor [*Oryza sativa Japonica* Group] | 78% |
| EEC83647.1 | hypothetical protein OsI_29392 [*Oryza sativa Indica* Group] | 78% |
| NP_974430.1 | ethylene-responsive transcription factor WRI1 [*Arabidopsis thaliana*] >gb|AEE79214.1| ethylene-responsive transcription factor WRI1 [*Arabidopsis thaliana*] | 78% |
| XP_003530370.1 | PREDICTED: ethylene-responsive transcription factor WRI1-like [*Glycine max*] | 78% |
| XP_002989385.1 | hypothetical protein SELMODRAFT_129793 [*Selaginella moellendorffii*] >gb|EFJ09476.1| hypothetical protein SELMODRAFT_129793 [*Selaginella moellendorffii*] | 78% |
| XP_003561189.1 | PREDICTED: AP2-like ethylene-responsive transcription factor ANT-like [*Brachypodium distachyon*] | 77% |
| ABL85061.1 | hypothetical protein 57h21.37 [*Brachypodium sylvaticum*] | 77% |
| XP_002323836.1 | AP2 domain-containing transcription factor [*Populus trichocarpa*] >gb|EEF03969.1| AP2 domain-containing transcription factor [*Populus trichocarpa*] | 77% |
| XP_002437819.1 | hypothetical protein SORBIDRAFT_10g003160 [*Sorghum bicolor*] >gb|EER89 186.1| hypothetical protein SORBIDRAFT_10g003160 [*Sorghum bicolor*] | 77% |
| EAZ35820.1 | hypothetical protein OsJ_20113 [*Oryza sativa Japonica* Group] | 77% |
| BAD68417.1 | AP2 DNA-binding domain protein-like [*Oryza sativa Japonica* Group] >dbj|BAD68772.1| AP2 DNA-binding domain protein-like [*Oryza sativa Japonica* Group] | 77% |
| EAY99657.1 | hypothetical protein OsI_21635 [*Oryza sativa Indica* Group] | 77% |
| XP_002517474.1 | conserved hypothetical protein [*Ricinus communis*] >gbEEF45016.1 conserved hypothetical protein [*Ricinus communis*] | 77% |
| XP_003567050.1 | PREDICTED: uncharacterized protein LOC100825100 [*Brachypodium distachyon*] | 77% |
| BAD10030.1 | AP2/EREBP transcription factor-like protein [*Oryza sativa Japonica* Group] | 77% |
| XP_003525949.1 | PREDICTED: AP2-like ethylene-responsive transcription factor At1g16060-like [*Glycine max*] | 76% |
| CBI36586.3 | unnamed protein product [*Vitis vinifera*] | 76% |
| NP_001077849.1 | AP2-like ethylene-responsive transcription factor [*Arabidopsis thaliana*] >gb|AEE36289.1| AP2-like ethylene-responsive transcription factor [*Arabidopsis thaliana*] | 76% |

-continued

| Accession | Description | Sequence Identity |
|---|---|---|
| CBI25261.3 | unnamed protein product [*Vitis vinifera*] | 76% |
| XP_002889265.1 | hypothetical protein ARALYDRAFT_477146 [*Arabidopsis lyrata* subsp. *lyrata*] >gb|EFH65524.1| hypothetical protein ARALYDRAFT_477146 [*Arabidopsis lyrata* subsp. *lyrata*] | 76% |
| XP_002441444.1 | hypothetical protein SORBIDRAFT_09g026800 [*Sorghum bicolor*] >gb|EES19874.1| hypothetical protein SORBIDRAFT_09g026800 [*Sorghum bicolor*] | 76% |
| XP_001779615.1 | predicted protein [*Physcomitrella patens* subsp. *patens*] >gb|EDQ55609.1 predicted protein [*Physcomitrella patens* subsp. *patens*] | 76% |
| XP_002460236.1 | hypothetical protein SORBIDRAFT_02g025080 [*Sorghum bicolor*] >gb|EER96757.1| hypothetical protein SORBIDRAFT_02g025080 [*Sorghum bicolor*] | 75% |
| XP_003533548.1 | PREDICTED: ethylene-responsive transcription factor WRI1-like [*Glycine max*] | 75% |
| XP_002272159.1 | PREDICTED: AP2-like ethylene-responsive transcription factor At1g16060-like [*Vitis vinifera*] | 75% |
| XP_002297679.1 | AP2 domain-containing transcription factor [*Populus trichocarpa*] >gb|EEE82484.1| AP2 domain-containing transcription factor [*Populus trichocarpa*] | 75% |
| XP_003578142.1 | PREDICTED: AP2-like ethylene-responsive transcription factor At1g16060-like [*Brachypodium distachyon*] | 75% |
| XP_002273046.2 | PREDICTED: AP2-like ethylene-responsive transcription factor At1g16060 [*Vitis vinifera*] | 75% |
| XP_003553203.1 | PREDICTED: AP2-like ethylene-responsive transcription factor ANT-like [*Glycine max*] | 75% |
| XP_003530686.1 | PREDICTED: AP2-like ethylene-responsive transcription factor At1g16060-like [*Glycine max*] | 75% |
| XP_002325111.1 | AP2 domain-containing transcription factor [*Populus trichocarpa*] >gb|EEF03676.1| AP2 domain-containing transcription factor [*Populus trichocarpa*] | 74% |
| XP_002315794.1 | AP2 domain-containing transcription factor [*Populus trichocarpa*] >gb|EEF01965.1| AP2 domain-containing transcription factor [*Populus trichocarpa*] | 74% |
| NP_001063215.1 | Os09g0423800 [*Oryza sativa* Japonica Group] >dbj|BAF25129.1| Os09g0423800 [*Oryza sativa* Japonica Group] | 74% |
| EAZ09147.1 | hypothetical protein OsI_31417 [*Oryza sativa* Indica Group] | 74% |
| NP_001146338.1 | uncharacterized protein LOC100279914 [*Zea mays*] >gb|ACL53718.1 unknown [*Zea mays*] | 74% |
| ACF84637.1 | unknown [*Zea mays*] | 74% |
| EEE69730.1 | hypothetical protein OsJ_29415 [*Oryza sativa* Japonica Group] | 74% |
| XP_003524030.1 | PREDICTED: AP2-like ethylene-responsive transcription factor At1g16060-like [*Glycine max*] | 74% |
| CBI22161.3 | unnamed protein product [*Vitis vinifera*] | 74% |
| XP_002303866.1 | AP2 domain-containing transcription factor [*Populus trichocarpa*] >gb|EEE78845.1| AP2 domain-containing transcription factor [*Populus trichocarpa*] | 74% |
| XP_003519167.1 | PREDICTED: AP2-like ethylene-responsive transcription factor At1g16060-like [*Glycine max*] | 73% |
| XP_003550676.1 | PREDICTED: AP2-like ethylene-responsive transcription factor At1g16060-like [*Glycine max*] | 73% |
| AAW78366.1 | transcription factor AP2D4 [*Oryza sativa* Japonica Group] | 72% |
| EEC79593.1 | hypothetical protein OsI_20775 [*Oryza sativa* Indica Group] | 72% |
| XP_003610261.1 | AP2 domain-containing transcription factor [*Medicago truncatula*] >gb|AES92458.1| AP2 domain-containing transcription factor [*Medicago truncatula*] | 72% |
| AAW78369.1 | transcription factor AP2D14 [*Oryza sativa* Japonica Group] | 71% |
| CAE00853.1 | AP2-1 protein [*Oryza sativa* Japonica Group] | 70% |
| BAJ33872.1 | unnamed protein product [*Thellungiella halophila*] | 70% |

Additional related WRINKLED1 sequences can also be targeted or employed in the methods, seeds, plant cells, and plants described herein, including those with about at least 40% sequence identity, or at least 50% sequence identity, or at least 60% sequence identity, or at least 70% sequence identity, or 60-99% sequence identity, or 70-99% sequence identity, or 80-99% sequence identity, or 90-95% sequence identity, or 90-99% sequence identity, or 95-97% sequence identity, or 97-99% sequence identity, or 100% sequence identity (or complementarity) with any of SEQ ID NO:7, SEQ ID NO:9, SEQ ID NO: 11, SEQ ID NO:13, or SEQ ID NO:17.

Thus, other ADP-glucose pyrophosphorylase and WRINKLED1 sequences in addition to those with SEQ ID NOs provided herein can also be used to generate modified plants with increase oil content in vegetative tissues. These other sequences can be related to the ADP-glucose pyrophosphorylase and WRINKLED1 described herein.

For example, such other ADP-glucose pyrophosphorylase and WRINKLED1 sequences can be isolated from a variety of plant types such as alfalfa (e.g., forage legume alfalfa), algae, avocado, barley, broccoli, Brussels sprouts, cabbage, canola, cassava, cauliflower, cole vegetables, collards, crucifers, grain legumes, grasses (e.g., forage grasses), jatropa, kale, kohlrabi, maize, miscanthus, mustards, nut sedge, oats, oil firewood trees, oilseeds, potato, radish, rice, rutabaga, sorghum, sugar beets, sugarcane, sunflower, switchgrass, tobacco, tomato, turnips, and wheat. In some embodiments, the plant is a *Brassicaceae* or other *Solanaceae* species. In some embodiments, the plant is not a species of *Arabidopsis*, for example, in some embodiments, the plant is not *Arabidopsis thaliana*.

Related Sequences

As described herein, nucleic acids are adapted to encode an ADP-glucose pyrophosphorylase enzyme and/or inhibit an ADP-glucose pyrophosphorylase. Such nucleic acids include nucleic acids related to the ADP-glucose pyrophosphorylase or WRINKLED1 nucleic acids described herein.

Nucleic acids with at least 50% sequence identity to those described herein can readily be identified, isolated and used to facilitate production of increased oil content in plants. Such nucleic acids can encode or hybridize to ADP-glucose pyrophosphorylase enzyme or WRINKLED1 nucleic acids, or fragments thereof. These related nucleic acids can be used to increase the expression of WRINKLED1 in plants. In addition, as described herein, inhibitory nucleic acids can be used to inhibit the expression of an ADP-glucose pyrophosphorylasenucleic acid and/or reduce the amount of ADP-glucose pyrophosphorylaseenzyme translated. The procedures described below can be employed to make an inhibitory RNA.

For example, related nucleic acids can be isolated and identified by mutation of the SEQ ID NO:2, SEQ ID NO:4, SEQ ID NO:6, SEQ ID NO:8, SEQ ID NO:10, SEQ ID NO:12, SEQ ID NO:14, and/or SEQ ID NO:18 nucleic acid sequences and/or by hybridization to DNA and/or RNA isolated from other plant species using the SEQ ID NO:2, SEQ ID NO:4, SEQ ID NO:6, SEQ ID NO:8, SEQ ID NO:10, SEQ ID NO:12, SEQ ID NO:14, and/or SEQ ID NO:18 nucleic acids as probes. Sequences of the ADP-glucose pyrophosphorylase enzyme (e.g., SEQ ID NO:1, 3 and/or 5) or the WRINKLED1 transcription factors (e.g., SEQ ID NO:7, 9, 11, 13 and/or 17) can also be examined and used a basis for designing alternative ADP-glucose pyrophosphorylase and/or WRINKLED1 nucleic acids.

In some embodiments, the ADP-glucose pyrophosphorylase nucleic acids for use herein include any nucleic acid that can selectively hybridize to a nucleic acid with any of the SEQ ID NO:2, 4 and 6 sequences. In some embodiments, the WRINKLED1 nucleic acids described herein include any nucleic acid that can selectively hybridize to a nucleic acid with any of the SEQ ID NO:8, 10, 12, 14 and/or 18 sequences.

In some embodiments, the sequence of the ADP-glucose pyrophosphorylase nucleic acid (SEQ ID NO:2, 4 and/or 6) can be examined and used a basis for designing inhibitory nucleic acids for reducing the expression of the ADP-glucose pyrophosphorylase enzyme. In another embodiment, the WRINKLED1 nucleic acids (e.g., SEQ ID NO:8, 10, 12, 14 and/or 18) can be examined and used a basis for designing additional WRINKLED1 nucleic acids that function as transcription factors in selected plant species.

The term "selectively hybridize" includes hybridization, under stringent hybridization conditions, of a nucleic acid sequence to a specified nucleic acid target sequence (e.g., SEQ ID NO:2, SEQ ID NO:4, SEQ ID NO:6, SEQ ID NO:8, SEQ ID NO:10, SEQ ID NO:12, SEQ ID NO:14, and/or SEQ ID NO:18) to a detectably greater degree (e.g., at least 2-fold over background) than its hybridization to non-target nucleic acid sequences. Such selective hybridization substantially excludes non-target nucleic acids.

Related ADP-glucose pyrophosphorylase and/or WRINKLED1 nucleic acids sequences typically have about at least 40% sequence identity, or at least 50% sequence identity, or at least 60% sequence identity, or at least 70% sequence identity, or 60-99% sequence identity, or 70-99% sequence identity, or 80-99% sequence identity, or 90-95% sequence identity, or 90-99% sequence identity, or 95-97% sequence identity, or 97-99% sequence identity, or 100% sequence identity (or complementarity) with any of SEQ ID NO:2, SEQ ID NO:4, SEQ ID NO:6, SEQ ID NO:8, SEQ ID NO:10, SEQ ID NO:12, SEQ ID NO:14, and/or SEQ ID NO:18. In some embodiments, a selectively hybridizing sequence has about at least about 80% sequence identity or complementarity with any of SEQ ID NO:2, SEQ ID NO:4, SEQ ID NO:6, SEQ ID NO:8, SEQ ID NO:10, SEQ ID NO:12, SEQ ID NO:14, and/or SEQ ID NO:18. The ADP-glucose pyrophosphorylase and/or WRINKLED1 nucleic acids employed in the expression vectors, transgenes, plants, plant cells, plant seeds and methods described herein can also have less than 100%, or less than 99.5%, or less than 99% sequence identity (or complementarity) with any of SEQ ID NO:2, SEQ ID NO:4, SEQ ID NO:6, SEQ ID NO:8, SEQ ID NO:10, SEQ ID NO:12, SEQ ID NO:14, and/or SEQ ID NO:18. In other words, the ADP-glucose pyrophosphorylase and/or WRINKLED1 nucleic acids employed in the expression vectors, transgenes, plants, plant cells, plant seeds and methods described herein can also not include a wild type sequence.

In some embodiments, the nucleic acids used in the methods and plants provided herein can include fragments of ADP-glucose pyrophosphorylase and/or WRINKLED1 nucleic acids. For example, the nucleic acids of the invention include those with about 300 of the same nucleotides as any of the SEQ ID NO:2, 4, 6, 8, 10, 12, 14 and 18 sequences, or about 400 of the same nucleotides as any of the SEQ ID NO: 2, 4, 6, 8, 10, 12, 14 and 18 sequences, or about 500 of the same nucleotides as any of the SEQ ID NO: 2, 4, 6, 8, 10, 12, 14 and 18 sequences, or about 600 of the same nucleotides as any of the SEQ ID NO: 2, 4, 6, 8, 10, 12, 14 and 18 sequences, or about 700 of the same nucleotides as any of the SEQ ID NO: 2, 4, 6, 8, 10, 12, 14 and 18 sequences, or about 800 of the same nucleotides as any of the SEQ ID NO: 2, 4, 6, 8, 10, 12, 14 and 18 sequences, or about 900 of the same nucleotides as any of the SEQ ID NO:2, 4, 6, 8, 10, 12, 14 and 18 sequences, or about 1000 of the same nucleotides as any of the SEQ ID NO: 2, 4, 6, 8, 10, 12, 14 and 18 sequences, or about 1100 of the same nucleotides as any of the SEQ ID NO: 2, 4, 6, 8, 10, 12, 14 and 18 sequences, or about 500-1100 of the same nucleotides as any of the SEQ ID NO: 2, 4, 6, 8, 10, 12, 14 and 18 sequences. The identical nucleotides can be distributed throughout the nucleic acid, and need not be contiguous.

For example, the nucleic acid sequence of a WRINKLED1 nucleic acid can be optimized for expression in a particular plant species by altering selected codons to encode the same amino acid but use nucleotide codons that are more easily 'read' by the transcription/translation machinery of a selected plant species.

In some embodiments, an inhibitory the nucleic acid of the invention can include an oligonucleotide sequence that is substantially identical or complementary to an ADP-glucose pyrophosphorylase nucleic acid with any of the SEQ ID NO:2, 4 and 6 sequences. For example, an inhibitory the nucleic acid of the invention can include those with about 14 of the same (or complementary) nucleotides as any of the SEQ ID NO:2, 4 and 6 sequences, or about 15 of the same (or complementary) nucleotides as any of the SEQ ID NO:2, 4 and 6 sequences, or about 16 of the same (or complementary) nucleotides as any of the SEQ ID NO:2, 4 and 6 sequences, or about 17 of the same (or complementary) nucleotides as any of the SEQ ID NO:2, 4 and 6 sequences, or about 18 of the same (or complementary) nucleotides as any of the SEQ ID NO:2, 4 and 6 sequences, or about 19 of the same (or complementary) nucleotides as any of the SEQ ID NO:2, 4 and 6 sequences, or about 20 of the same (or complementary) nucleotides as any of the SEQ ID NO:2, 4 and 6 sequences, or about 21 of the same (or complementary) nucleotides as any of the SEQ ID NO:2, 4 and 6 sequences, or about 22 of the same (or complementary) nucleotides as any of the SEQ ID NO:2, 4 and 6 sequences, or about 23 of the same (or complementary) nucleotides as any of the SEQ ID NO:2, 4 and 6 sequences, or about 24 of the same (or complementary) nucleotides as any of the SEQ ID NO:2, 4 and 6 sequences, or about 25 of the same (or complementary) nucleotides as any of the SEQ ID NO:2, 4 and 6 sequences, or about 26 of the same (or complementary) nucleotides as any of the SEQ ID NO:2, 4 and 6 sequences, or about 27 of the same (or complementary) nucleotides as any of the SEQ ID NO:2, 4 and 6 sequences, or about 28 of the same (or complementary) nucleotides as any of the SEQ ID NO:2, 4 and 6 sequences, or about 29 of the same (or complementary) nucleotides as any of the SEQ ID NO:2, 4 and 6 sequences, or about 30 of the same (or complementary) nucleotides as any of the SEQ ID NO:2, 4 and 6 sequences, or about 31 of the same (or complementary) nucleotides as any of the SEQ ID NO:2, 4 and 6 sequences, or about 32 of the same (or complementary) nucleotides as any of the SEQ ID NO:2, 4 and 6 sequences, or about 33 of the same (or complementary) nucleotides as any of the SEQ ID NO:2, 4 and 6 sequences, or about 34 of the same (or complementary) nucleotides as any of the SEQ ID NO:2, 4 and 6 sequences, or about 35 of the same (or complementary) nucleotides as any of the SEQ ID NO:2, 4 and 6 sequences, or about 36 of the same (or complementary) nucleotides as any of the SEQ ID NO:2, 4 and 6 sequences, or about 37 of the same (or complementary) nucleotides as any of the SEQ ID NO:2, 4 and 6 sequences, or about 38 of the same (or complementary) nucleotides as any of the SEQ ID NO:2, 4 and 6 sequences, or about 39 of the same (or complementary) nucleotides as any of the SEQ ID NO:2, 4 and 6 sequences, or about of the same (or complementary) nucleotides as any of the SEQ ID NO:2, 4 and 6 sequences, or about 41 of the same (or complementary) nucleotides as any of the SEQ ID NO:2, 4 and 6 sequences, or about 42 of the same (or complementary) nucleotides as any of the SEQ ID NO:2, 4 and 6 sequences, or about 43 of the same (or complementary) nucleotides as any of the SEQ ID NO:2, 4 and 6 sequences, or about 44 of the same (or complementary) nucleotides as any of the SEQ ID NO:2, 4 and 6 sequences, or about 45 of the same (or complementary) nucleotides as any of the SEQ ID NO:2, 4 and 6 sequences, or about 14-50 of the same (or complementary) nucleotides as any of the SEQ ID NO:2, 4 and 6 sequences. Such an inhibitory nucleic acid can be RNA or DNA.

The inhibitory nucleic acid can have a sequence that has 100% or less than 100% sequence identity to a wild type plant nucleic acid. For example, the inhibitory nucleic acid can have a sequence that has 99.5%, or 99%, or less sequence identity to a wild type plant nucleic acid.

Note that if a value of a variable that is necessarily an integer (e.g., the number of nucleotides or amino acids in a nucleic acid or protein), is described as a range, e.g., 80-99% sequence identity what is meant is that the value can be any integer between 80 and 99 inclusive, i.e., 80, 81, 82, 83, 84, 85, 86, 87, 88, 89, 90, 91, 92, 93, 94, 95, 96, 97, 98 or 99, or any range between 80 and 99 inclusive, e.g., 81-99%, 81-98%, 82-99%, etc. Moreover, if a specifically recited percent sequence identity indicates that a partial nucleotide or amino acid is present (in a nucleic acid or polypeptide) the percent sequence identity is rounded up or down so that a complete nucleotide or amino acid is present.

In some embodiments, related nucleic acid hybridizes to the nucleic acids described herein under "stringent conditions" or "stringent hybridization conditions." In other embodiments, an inhibitory nucleic acid can hybridize to the nucleic acids described herein under "physiological conditions," "stringent conditions" or "stringent hybridization conditions."

The term "physiological conditions" refers to salt and temperature conditions that are commonly present in a live plant in vivo, for example, in a growing plant or seedling. Inhibitory nucleic acids and oligonucleotides can, for example, hybridize to an endogenous nucleic acid (e.g., an mRNA arising from a nucleic acid with any of the SEQ ID NO:2, 4, and 6 sequences) under plant physiological conditions. In some embodiments, under such plant physiological conditions, the inhibitory nucleic acids and oligonucleotides selectively hybridize to a mRNA with any of the SEQ ID NO:2, 4 and 6 sequences.

The terms "stringent conditions" or "stringent hybridization conditions" include conditions under which a probe will hybridize to its target sequence to a detectably greater degree than other sequences (e.g., at least 2-fold over background). Stringent conditions are somewhat sequence-dependent and can vary in different circumstances. By controlling the stringency of the hybridization and/or washing conditions, target sequences can be hybridized that have up to 100% complementarity to the probe or inhibitory nucleic acid (homologous probing). Alternatively, stringency conditions can be adjusted to allow some mismatching in sequences so that lower degrees of sequence similarity are detected (heterologous probing).

A probe for identifying and/or isolating a related nucleic acid can be approximately 15-500 nucleotides in length, but can vary greatly in length from about 17 nucleotides to equal to the entire length of the target sequence. In some embodiments, the probe is about 10-50 nucleotides in length, or about 15-50 nucleotides in length, or about 16-45 nucleotides in length, or about 18-25 nucleotides in length.

Typically, stringent conditions will be those where the salt concentration is less than about 1.5 M Na ion (or other salts), typically about 0.01 to 1.0 M Na ion concentration (or other salts), at pH 7.0 to 8.3 and the temperature is at least about 30° C. for shorter probes (e.g., 10 to 50 nucleotides) and at least about 60° C. for longer probes (e.g., greater than 50 nucleotides). Stringent conditions may also be achieved with the addition of destabilizing agents such as formamide or Denhardt's solution. Exemplary low stringency conditions include hybridization with a buffer solution of 30 to 35% formamide, 1M NaCl, 1% SDS (sodium dodecyl sulfate) at 37° C., and a wash in 1×SSC to 2×SSC (where 20×SSC is 3.0 M NaCl, 0.3 M trisodium citrate) at 50 to 55° C. Exemplary moderate stringency conditions include hybridization in 40 to 45% formamide, 1M NaCl, 1% SDS at 37° C., and a wash in 0.5×SSC to 1×SSC at 55 to 60° C. Exemplary high stringency conditions include hybridization in 50% formamide, 1M NaCl, 1% SDS at 37° C., and a wash in 0.1×SSC at 60 to 65° C. Specificity is typically a function of post-hybridization washes, where the factors controlling hybridization include the ionic strength and temperature of the final wash solution. Hence, high stringency conditions include can be achieved simply by employing a wash in 0.1×SSC at 60 to 65° C.

For DNA-DNA hybrids, the $T_m$ can be approximated from the equation of Meinkoth and Wahl (Anal. Biochem. 138: 267-84 (1984)):

$$T_m=81.5° C.+16.6(\log M)+0.41(\% GC)-0.61(\% \text{formamide})-500/L$$

where M is the molarity of monovalent cations; % GC is the percentage of guanosine and cytosine nucleotides in the DNA, % formamide is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. The $T_m$ is reduced by about 1° C. for each 1% of mismatching. Thus, the $T_m$, hybridization and/or wash conditions can be adjusted to hybridize to sequences of the desired sequence identity. For example, if sequences with greater than or equal to 90% sequence identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can include hybridization and/or a wash at 1, 2, 3 or 4° C. lower than the thermal melting point ($T_m$). Moderately stringent conditions can include hybridization and/or a wash at 6, 7, 8, 9 or 10° C. lower than the thermal melting point ($T_m$). Low stringency conditions can include hybridization and/or a wash at 11, 12, 13, 14, 15 or 20° C. lower than the thermal melting point ($T_m$). Using the equation, hybridization and wash compositions, and a desired $T_m$, those of ordinary skill can identify and isolate nucleic acids with sequences related to any of the SEQ ID NO:2, 4 and 6 sequences. Similarly, those of ordinary skill can identify and isolate inhibitory nucleic acids with sequences that effectively inhibit the expression of a nucleic acid that includes any of the SEQ ID NO:2, 4 and 6 sequences.

Those of skill in the art also understand how to vary the hybridization and/or wash solutions to isolate desirable nucleic acids. For example, if the desired degree of mismatching results in a $T_m$ of less than 45° C. (aqueous solution) or 32° C. (formamide solution) it is preferred to increase the SSC concentration so that a higher temperature can be used.

An extensive guide to the hybridization of nucleic acids is found in Tijssen, LABORATORY TECHNIQUES IN BIOCHEMISTRY AND MOLECULAR BIOLOGY—HYBRIDIZATION WITH NUCLEIC ACID PROBES, part 1, chapter 2, "Overview of principles of hybridization and the strategy of nucleic acid probe assays," Elsevier, N.Y. (1993); and in CURRENT PROTOCOLS IN MOLECULAR BIOLOGY, chapter 2, Ausubel, et al., eds, Greene Publishing and Wiley-Interscience, New York (1995).

Unless otherwise stated, in the present application, high stringency is defined as a wash in 0.1×SSC, 0.1% SDS at 65° C. High stringency hybridization can include hybridization in 4×SSC, 5×Denhardt's (5 g Ficoll, 5 g polyvinylpyrrolidone, 5 g bovine serum albumin in 500 ml of water), 0.1 mg/ml boiled salmon sperm DNA, and 25 mM Na phosphate at 65° C., followed by a wash in 0.1×SSC, 0.1% SDS at 65° C.

The following terms are used to describe the sequence relationships between two or more nucleic acids or nucleic acids or polypeptides: (a) "reference sequence," (b) "comparison window," (c) "sequence identity," (d) "percentage of sequence identity" and (e) "substantial identity."

As used herein, "reference sequence" is a defined sequence used as a basis for sequence comparison. The reference sequence can be a nucleic acid sequence (e.g., any of the SEQ ID NO:2, 4, 6, 8, 10, 12, 14 and 18 nucleic acid sequences) or an amino acid sequence (e.g., any of the SEQ ID NO:1, 3, 5, 7, 9, 11, 13 and 17 amino acid sequences). A reference sequence may be a subset or the entirety of a specified sequence. For example, a reference sequence may be a segment of a full-length cDNA or of a genomic DNA sequence, or the complete cDNA or complete genomic DNA sequence, or a domain of a polypeptide sequence.

As used herein, "comparison window" refers to a contiguous and specified segment of a nucleic acid or an amino acid sequence, wherein the nucleic acid/amino acid sequence can be compared to a reference sequence and wherein the portion of the nucleic acid/amino acid sequence in the comparison window may comprise additions or deletions (i.e., gaps) compared to the reference sequence (which does not comprise additions or deletions) for optimal alignment of the two sequences. The comparison window can vary for nucleic acid and polypeptide sequences. Generally, for nucleic acids, the comparison window is at least 16 contiguous nucleotides in length, and optionally can be 18, 20, 30, 40, 50, 100 or more nucleotides. For amino acid sequences, the comparison window is at least about 15 amino acids, and can optionally be 20, 30, 40, 50, 100 or more amino acids. Those of skill in the art understand that to avoid a high similarity to a reference sequence due to inclusion of gaps in the nucleic acid or amino acid sequence, a gap penalty is typically introduced and is subtracted from the number of matches.

Methods of alignment of nucleotide and amino acid sequences for comparison are well known in the art. The local homology algorithm (BESTFIT) of Smith and Waterman, (1981) Adv. Appl. Math 2:482, may permit optimal alignment of compared sequences; by the homology alignment algorithm (GAP) of Needleman and Wunsch, (1970) J. Mol. Biol. 48:443-53; by the search for similarity method (Tfasta and Fasta) of Pearson and Lipman, (1988) Proc. Natl. Acad. Sci. USA 85:2444; by computerized implementations of these algorithms, including, but not limited to: CLUSTAL in the PC/Gene program by Intelligenetics, Mountain View, Calif., GAP, BESTFIT, BLAST, FASTA and TFASTA in the Wisconsin Genetics Software Package, Version 8 (available from Genetics Computer Group (GCG™ programs (Accelrys, Inc., San Diego, Calif.)). The CLUSTAL program is well described by Higgins and Sharp (1988) Gene 73:237-44; Higgins and Sharp, (1989) CABIOS 5:151-3; Corpet, et al., (1988) Nucleic Acids Res. 16:10881-90; Huang, et al., (1992) Computer Applications in the Biosciences 8:155-65 and Pearson, et al., (1994) Meth. Mol. Biol. 24:307-31. An example of a good program to use for optimal global alignment of multiple sequences is PileUp (Feng and Doolittle, (1987) J. Mol. Evol., 25:351-60, which is similar to the method described by Higgins and Sharp, (1989) CABIOS 5:151-53 (and is hereby incorporated by reference). The BLAST family of programs that can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, Current Protocols in Molecular Biology, Chapter 19, Ausubel, et al., eds., Greene Publishing and Wiley-Interscience, New York (1995).

GAP uses the algorithm of Needleman and Wunsch, (1970) J. Mol. Biol. 48:443-53, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP makes a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package are 8 and 2, respectively. The gap creation and gap extension penalties can be expressed as an integer selected from the group of integers consisting of from 0 to 100. Thus, for example, the gap creation and gap extension penalties can be 0, 1, 2, 3, 4, 5, 6, 7, 8, 9, 10, 15, 20, 30, 40, 50 or more.

GAP presents one member of the family of best alignments. There may be many members of this family. GAP displays four figures of merit for alignments: Quality, Ratio, Identity and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see, Henikoff and Henikoff, (1989) Proc. Natl. Acad. Sci. USA 89:10915).

Unless otherwise stated, sequence identity/similarity values provided herein refer to the value obtained using the BLAST 2.0 suite of programs using default parameters (Altschul, et al., (1997) Nucleic Acids Res. 25:3389-402).

As those of ordinary skill in the art will understand, BLAST searches assume that proteins can be modeled as random sequences. However, many real proteins comprise regions of nonrandom sequences, which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, (1993) Comput. Chem. 17:149-63) and XNU (C.sub.1-ayerie and States, (1993) Comput. Chem. 17:191-201) low-complexity filters can be employed alone or in combination.

The terms "substantial identity" indicates that an inhibitory nucleic acid, polypeptide or related nucleic acid comprises a sequence with between 55-100% sequence identity to a reference sequence, with at least 55% sequence identity, or at least 60%, or at least 70%, or at least 80%, or at least 90% or at least 95% sequence identity or any percentage of range between 55-100% sequence identity relative to the reference sequence over a specified comparison window. Optimal alignment may be ascertained or conducted using the homology alignment algorithm of Needleman and Wunsch, supra.

An indication that two polypeptide sequences are substantially identical is that both polypeptides have similar activities. For example, when a polypeptide is related to ADP-glucose pyrophosphorylase, that polypeptide can synthesize glycogen and/or starch from ADP-glucose. When the polypeptide is related to WRINKLED1, that polypeptide can act as a transcription factor by binding to the same or similar upstream regions of genes normally under the regulatory control of WRINKLED1. For example, transcription factors related to the WRINKLED1 can be identified and/or characterized in assays that involve binding of a test protein (i.e., a potential transcription factor related to a WRINKLED1 factor) to a promoter or regulatory sequence that is bound by a WRINKLED1 factor with any of the sequences recited herein. The related WRINKLED1 polypeptide can also be identified, evaluated or characterized in assays for observing increased (or decreased) expression a set of genes involved in fatty acid (FA) synthesis including, for example, genes for a subunit of pyruvate kinase (Pl-PKβ1), acetyl-CoA carboxylase (BCCP2), acyl carrier protein (ACP1), ketoacyl-acyl carrier protein synthase (KAS1), and combinations thereof.

In some embodiments, the polypeptide that is substantially identical to an ADP-glucose pyrophosphorylase with a SEQ ID NO: 1, 3 or 5 sequence or a WRINKLED1 transcription factor with a SEQ ID NO:7, 9, 11, 13 or 17 sequence may not have exactly the same level of activity as the ADP-glucose pyrophosphorylase with a SEQ ID NO:1, 3 or 5, or the WRINKLED1 transcription factor with a SEQ ID NO:7, 9, 11, 13 or 17 sequence, respectively. Instead, the substantially identical polypeptide may exhibit greater or lesser levels of activity than the ADP-glucose pyrophosphorylase with SEQ ID NO:1, 3 or 5, or the WRINKLED1 transcription factor with a SEQ ID NO:7, 9, 11, 13 or 17 sequence, as measured by assays available in the art. For example, the substantially identical polypeptide may have at least about 40%, or at least about 50%, or at least about 60%, or at least about 70%, or at least about 80%, or at least about 90%, or at least about 95%, or at least about 97%, or at least about 98%, or at least about 100%, or at least about 105%, or at least about 110%, or at least about 120%, or at least about 130%, or at least about 140%, or at least about 150%, or at least about 200% of the activity of the ADP-glucose pyrophosphorylase with the SEQ ID NO:1, 3, or 5 sequence, or the WRINKLED1 transcription factor with a SEQ ID NO:7, 9, 11, 13 or 17 sequence, when measured by similar assay procedures.

Alternatively, substantial identity is present when second polypeptide is immunologically reactive with antibodies raised against the first polypeptide (e.g., a polypeptide with SEQ ID NO:1, 3, 5, 7, 9, 11, 13 or 17 sequence). Thus, a polypeptide is substantially identical to a first polypeptide, for example, where the two polypeptides differ only by a conservative substitution. In addition, a polypeptide can be substantially identical to a first polypeptide when they differ by a non-conservative change if the epitope that the antibody recognizes is substantially identical. Polypeptides that are "substantially similar" share sequences as noted above except that some residue positions, which are not identical, may differ by conservative amino acid changes.

The WRINKLED1 polypeptides of the present invention may include the first 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 and 99 N-terminal amino acid residues of a the SEQ ID NO:7, 9, 11, 13 or 17 sequence, or of a sequence related to any of the SEQ ID NO:7, 9, 11, 13 or 17 sequences. In some embodiments, the WRINKLED1 polypeptides of the present invention may include the first 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 and 99 C-terminal amino acid residues of a the SEQ ID NO:7, 9, 11, 13 or 17 sequence, or of a sequence related to any of the SEQ ID NO:7, 9, 11, 13 or 17 sequences.

Inhibitory Nucleic Acids

In another embodiment, the invention relates to an inhibitory nucleic acid that can reduce the expression and/or translation of an ADP-glucose pyrophosphorylase. For example, the inhibitory nucleic acid that can reduce the expression and/or translation of an ADP-glucose pyrophosphorylase having any of the SEQ ID NO:2, 4 and 6 sequences. The inhibitory nucleic acid can reduce the expression of an ADP-glucose pyrophosphorylase by any amount such as, for example, by 2%, 5%, 10%, 20%, 40% or more than 40%.

In one embodiment, an inhibitory nucleic acid may be an oligonucleotide that will hybridize to an ADP-glucose pyrophosphorylase nucleic acid under intracellular, physiological or stringent conditions. The oligonucleotide is capable of reducing expression of a nucleic acid encoding the ADP-glucose pyrophosphorylase. A nucleic acid encoding a ADP-glucose pyrophosphorylase that is inhibited as described herein may be genomic DNA or a messenger RNA. For example, in some embodiments, the inhibitory nucleic acid can hybridize to any of the SEQ ID NO:2, 4 and 6 sequences, or to a complementary strand of any of the SEQ ID NO:2, 4, and 6 sequences. The inhibitory nucleic acid may, for example, be incorporated into a plasmid vector or viral DNA. The inhibitory nucleic acid can also be expressed from an expression vector, plasmid vector or viral DNA. The inhibitory nucleic acid may be single stranded or double stranded, circular or linear. The inhibitory nucleic acid may also have a stem-loop structure.

When the inhibitory nucleic acid is an oligonucleotide, such an oligonucleotide can be a polymer of ribose nucleotides or deoxyribose nucleotides. Such an inhibitory oligonucleotide can be of varying lengths. For example, an inhibitory oligonucleotide can be more than 13 nucleotides in length. For example, an inhibitory nucleic acid may include naturally-occurring nucleotides as well as synthetic, modified, or pseudo-nucleotides. The inhibitory nucleic acids can include modified nucleotides such as phosphorothiolates; 2'-O alkyl-containing nucleotides, and nucleotides having a detectable label such as $P^{32}$, biotin or digoxigenin. The inhibitory nucleic acids can include peptide nucleic acid (PNA), locked nucleic acid (LNA) and morpholino nucleotide sequences.

An inhibitory nucleic acid that can reduce the expression and/or activity of an ADP-glucose pyrophosphorylase nucleic acid, may be completely complementary and/or completely identical to the ADP-glucose pyrophosphorylase nucleic acid (e.g., a DNA, cDNA or RNA). Alternatively, some variability between the sequences may be permitted. An inhibitory nucleic acid that can inhibit an ADP-glucose pyrophosphorylase nucleic acid can hybridize to the ADP-glucose pyrophosphorylase nucleic acid under intracellular conditions or under stringent hybridization conditions. For example, an inhibitory nucleic acid can be sufficiently complementary to inhibit expression or translation of an ADP-glucose pyrophosphorylase nucleic acid. Intracellular conditions refer to conditions such as temperature, pH and salt concentrations typically found inside a cell, for example, a living plant cell.

Inhibitory nucleic acids (e.g., oligonucleotides) can include, for example, 2, 3, 4, or 5 or more stretches of contiguous nucleotides that are precisely complementary to an ADP-glucose pyrophosphorylase nucleic acid coding sequence, each separated by a stretch of contiguous nucleotides that are not complementary to adjacent coding sequences, may inhibit the function of a ADP-glucose pyrophosphorylase nucleic acid. In general, each stretch of contiguous nucleotides is at least 4, 5, 6, 7, or 8 or more nucleotides in length. Non-complementary intervening sequences may be 1, 2, 3, or 4 nucleotides in length. One skilled in the art can easily use the calculated melting point of an oligonucleotide hybridized to a sense nucleic acid to estimate the degree of mismatching that will be tolerated for inhibiting expression of a particular target nucleic acid.

Inhibitory nucleic acids include, for example, ribozymes, antisense nucleic acids, interfering RNA, microRNA, small interfering RNA (siRNA), and combinations thereof.

An antisense nucleic acid molecule is typically single-stranded that is complementary to the target nucleic acid (a nucleic acid encoding an ADP-glucose pyrophosphorylase). The antisense nucleic acid may function in an enzyme-dependent manner or, more frequently, by steric blocking. Steric blocking antisense, which are RNase-H independent, interferes with gene expression or other mRNA-dependent cellular processes by binding to a target mRNA and getting in the way of other processes.

An antisense oligonucleotide can be complementary to a sense nucleic acid encoding an ADP-glucose pyrophosphorylase protein. For example, it may be complementary to the coding strand of a double-stranded cDNA molecule or complementary to an mRNA sequence. It may be complementary to an entire coding strand or to only a portion thereof. It may also be complementary to all or part of the noncoding region of a nucleic acid encoding an ADP-glucose pyrophosphorylase protein. The non-coding region includes the 5' and 3' regions that flank the coding region, for example, the 5' and 3' untranslated sequences. An antisense oligonucleotide is generally at least six nucleotides in length, but may be about 8, 12, 13, 14, 15, 16, 17, 18, 19, 20, 21, 22, 23, 24, 25, 30, 35, 40, 45, or 50 nucleotides long. Longer oligonucleotides may also be used.

An antisense oligonucleotide may be prepared using methods known in the art, for example, by expression from an expression vector encoding the antisense oligonucleotide or from an expression cassette. For example, an antisense nucleic acid can be generated simply by flipping over the coding region of an mRNA, thereby allowing a regulatory sequence (e.g., a promoter) to transcribe the "wrong" DNA strand. The transcript so-produced is an antisense RNA, which will bind and inactivate the RNA produced by the normal gene.

RNA interference (also referred to as "RNA-mediated interference") (RNAi) is an effective mechanism by which gene expression can be reduced or eliminated. Double stranded RNA (dsRNA) or single stranded RNA has been observed to mediate the reduction, which is a multi-step process (for details of single stranded RNA methods and compositions see, e.g., Martinez et al., *Cell,* 110(5):563 (2002)). dsRNA activates post-transcriptional gene expression surveillance mechanisms that appear to function to defend cells from virus infection and transposon activity (Fire et al., *Nature,* 391:806-811 (1998); Grishok et al., *Cell,* 106: 23-34 (2001); Ketting et al., *Cell,* 99:133-141 (1999); Lin and Avery, *Nature,* 402:128-129 (1999); Montgomery et al., *Proc. Natl. Acad. Sci. USA,* 95:15502-07 (1998); Sharp and Zamore, *Science,* 287:2431-2433 (2000); Tabara et al., *Cell,* 99:123-132 (1999)). Activation of these mechanisms targets mature, dsRNA-complementary mRNA for destruction. The double stranded RNA reduces the expression of the gene to which the dsRNA corresponds.

For example, RNAi can be made from two oligonucleotides consisting of partially complementary sequences. The oligonucleotides can be made recombinantly, for example, from one or two expression cassettes and/or expression vectors.

RNAi has some advantages including high specificity, ease of movement across cell membranes, and prolonged down-regulation of the targeted gene. (Fire et al., 1998; Grishok et al., 2000; Ketting et al., 1999; Lin et al., 1999; Montgomery et al., 1998; Sharp et al., 2000; Tabara et al., 1999). Moreover, dsRNA has been shown to silence genes in a wide range of systems, including plants, protozoans, fungi, *C. elegans, Trypanasoma, Drosophila,* and mammals (Grishok et al., 2000; Sharp, Genes Dev., 13:139-141 (1999); Sharp et al., 2000; Elbashir et al., *Nature,* 411:494-498 (2001)).

Small interfering RNAs (siRNAs) or short hairpin RNAs (shRNAs) can also be used to specifically reduce ADP-glucose pyrophosphorylase expression such that the level of ADP-glucose pyrophosphorylase polypeptides is reduced. siRNAs are double-stranded RNA molecules that mediate post-transcriptional gene silencing in a sequence-specific manner. See, for example, Hamilton & Baulcombe, Science 286 (5441): 950-2 (1999); see also, the website at invitrogen.com/site/us/en/home/Products-and-Services/Applications/rnai/Synthetic-RNAi-Analysis/Ambion-Silencer-Select-siRNAs/Silencer-Select-Pre-Designed-and-Validated-siRNA.html. Once incorporated into an RNA-induced silencing complex, siRNA mediate cleavage of the homologous endogenous mRNA transcript by guiding the complex to the homologous mRNA transcript, which is then cleaved by the complex.

For example, siRNA can be made from two partially or fully complementary oligonucleotides. Alternatively, short hairpin RNA (shRNA) can be employed that is a one oligonucleotide that forms a double-stranded region by folding back onto itself via a tight hairpin turn. The siRNA and/or shRNA may have sequence identity, sequence complementarity and/or be homologous to any region of the ADP-glucose pyrophosphorylase mRNA transcript. The region of sequence homology or complementarity may be less than 45 nucleotides, less than 40 nucleotides, less than 35 nucleotides, less than 30 nucleotides, or less than 25 nucleotides in length. In some embodiments, the region of sequence homology or complementarity of a siRNA or shRNA may be about 21 to 23 nucleotides in length.

SiRNA is typically double stranded and may have two-nucleotide 3' overhangs, for example, 3' overhanging UU dinucleotides. Methods for designing siRNAs are known to those skilled in the art. See, for example, Elbashir et al. *Nature* 411: 494-498 (2001); Harborth et al. *Antisense Nucleic Acid Drug Dev.* 13: 83-106 (2003). Typically, a target site that begins with AA, has 3' UU overhangs for both the sense and antisense siRNA strands, and has an approximate 50% G/C content is selected. SiRNAs may be chemically synthesized, created by in vitro transcription, or expressed from an siRNA expression vector or a PCR expression cassette. See, e.g., the website at www.ambion-.com/techlib/tb/tb_506html (last retrieved May 10, 2006).

When a shRNA is expressed from an expression vector or a PCR expression cassette, the insert encoding the shRNA may be expressed as an RNA transcript that folds into an shRNA hairpin. Thus, the shRNA transcript may include a sense siRNA sequence that is linked to its reverse complementary antisense siRNA sequence by a spacer sequence that forms the loop of the hairpin as well as a string of U's at the 3' end. The loop of the hairpin may be of various lengths. For example, the loop can be 3 to 30 nucleotides in length, or 3 to 23 nucleotides in length. Examples of nucleotide sequences for the loop include AUG, CCC, UUCG, CCACC, CTCGAG, AAGCUU, CCACACC and UUCAAGAGA (SEQ ID NO: 19).

SiRNAs also may be produced in vivo by cleavage of double-stranded RNA introduced directly or via a transgene or virus. Further information on selection and properties of inhibitory nucleic acids is provided in the next section.

The inhibitory nucleic acid may also be a ribozyme. A ribozyme is an RNA molecule with catalytic activity and is capable of cleaving a single-stranded nucleic acid such as an mRNA that has a homologous region. See, for example, Cech, Science 236: 1532-1539 (1987); Cech, Ann. Rev. Biochem. 59:543-568 (1990); Cech, Curr. Opin. Struct. Biol. 2: 605-609 (1992); Couture and Stinchcomb, Trends Genet. 12: 510-515 (1996). A ribozyme may be used to catalytically cleave a ADP-glucose pyrophosphorylase mRNA transcript and thereby inhibit translation of the mRNA. See, for example, Haseloff et al., U.S. Pat. No. 5,641,673. A ribozyme having specificity for a ADP-glucose pyrophosphorylase nucleic acid may be designed based on the nucleotide sequence of any of the SEQ ID NO:2, 4 and 6 sequences. Methods of designing and constructing a ribozyme that can cleave an RNA molecule in trans in a highly sequence specific manner have been developed and described in the art. See, for example, Haseloff et al., Nature 334:585-591 (1988). A ribozyme may be targeted to a specific RNA by engineering a discrete "hybridization" region into the ribozyme. The hybridization region contains a sequence complementary to the target RNA that enables the ribozyme to specifically hybridize with the target. See, for example, Gerlach et al., EP 321,201. The target sequence may be a segment of about 5, 6, 7, 8, 9, 10, 12, 15, 20, or 50 contiguous nucleotides selected from a nucleic acid having any of the SEQ ID NO:2, 4 and 6 sequences. Longer complementary sequences may be used to increase the affinity of the hybridization sequence for the target. The hybridizing and cleavage regions of the ribozyme can be integrally related; thus, upon hybridizing to the target RNA through the complementary regions, the catalytic region of the ribozyme can cleave the target. Thus, an existing ribozyme may be modified to target a ADP-glucose pyrophosphorylase mRNA by modifying the hybridization region of the ribozyme to include a sequence that is complementary to the target ADP-glucose pyrophosphorylase. Alternatively, an mRNA encoding a ADP-glucose pyrophosphorylase may be used to select a catalytic RNA having a specific ribonuclease activity from a pool of RNA molecules. See, for example, Bartel & Szostak, Science 261: 1411-1418 (1993).

Inhibitory nucleic acids can be generated by recombinant means, for example, by expression from an expression cassette or expression vector. Alternatively, the inhibitory nucleic acid may be prepared by chemical synthesis using naturally-occurring nucleotides, modified nucleotides or any combinations thereof. In some embodiments, the oligonucleotides are made from modified nucleotides or non-phosphodiester bonds, for example, that are designed to increase biological stability of the oligonucleotide or to increase intracellular stability of the duplex formed between the antisense oligonucleotide and the sense nucleic acid. Naturally-occurring nucleotides include the ribose or deoxyribose nucleotides adenosine, guanine, cytosine, thymine and uracil. Examples of modified nucleotides include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladeninje, uracil-5-oxyacetic acid, wybutoxosine, pseudouracil, queosine, 2-thiocytosine, 5-methyl-2-thiouracil, 2-thiouracil, 4-thiouracil, 5-methyluracil, uracil-5-oxacetic acid methylester, uracil-5-oxacetic acid, 5-methyl-2-thiouracil, 3-(3-amino-3-N2-carboxypropyl) uracil, (acp3)w, and 2,6-diaminopurine. Thus, inhibitory nucleic acids may include modified nucleotides, as well as natural nucleotides such as combinations of ribose and deoxyribose nucleotides, and an antisense oligonucleotide of the invention may be of any length discussed above and that is homologous and/or complementary to any of the SEQ ID NO:2, 4 and 6 sequences.

Transgenic Plants

In order to engineer plants with increased vegetative tissue oil content that, one of skill in the art can introduce inhibitory nucleic acids that reduce the expression and/or translation of ADP-glucose pyrophosphorylase (inhibitory nucleic acids). Those of skill in the art can also introduce nucleic acids encoding WRINKLED1 transcription factors into the plants to promote the production of oils.

In some embodiments the inhibitory nucleic acids and transcription factors can be introduced directly into plant tissues. For example, one of skill in the art can inject ADP-glucose pyrophosphorylase inhibitory nucleic acids and/or inject WRINKLED1 enzymes into young plants.

Alternatively, one of skill in the art can generate genetically-modified plants that contain ADP-glucose pyrophosphorylase inhibitory nucleic acids and/or nucleic acids encoding WRINKLED1 transcription factors within their somatic and/or germ cells. Such genetic modification can be accomplished by procedures available in the art. For example, one of skill in the art can prepare an expression cassette or expression vector that can express one or more ADP-glucose pyrophosphorylase inhibitory nucleic acids and/or one or more encoded WRINKLED1 enzymes. Plant cells can be transformed by the expression cassette or expression vector, and whole plants (and their seeds) can be generated from the plant cells that were successfully transformed with the ADP-glucose pyrophosphorylase inhibitory nucleic acids and/or with the WRINKLED1 nucleic acids. Some procedures for making such genetically modified plants and their seeds are described below.

Promoters:

The ADP-glucose pyrophosphorylase inhibitory nucleic acids and/or the WRINKLED1 nucleic acids can be operably linked to a promoter, which provides for expression of an inhibitory RNA and/or mRNA from the WRINKLED1 nucleic acids. The promoter is typically a promoter functional in plants and/or seeds, and can be a promoter functional during plant growth and development or in a mature plant. The promoter can be a heterologous promoter. As used herein, "heterologous" when used in reference to a gene or nucleic acid refers to a gene or nucleic acid that has been manipulated in some way. For example, a heterologous promoter is a promoter that contains sequences that are not naturally linked to an associated coding region.

An ADP-glucose pyrophosphorylase inhibitory nucleic acid and/or a WRINKLED1 nucleic acid is operably linked to the promoter when it is located downstream from the promoter, to thereby form an expression cassette. The ADP-glucose pyrophosphorylase inhibitory nucleic acids can be separately regulated from the WRINKLED1 nucleic acids by use of separate promoters and/or separate expression cassettes.

Promoter regions are typically found in the flanking DNA upstream from the coding sequence in both prokaryotic and eukaryotic cells. A promoter sequence provides for regulation of transcription of the downstream gene sequence and typically includes from about 50 to about 2,000 nucleotide base pairs. Promoter sequences also contain regulatory sequences such as enhancer sequences that can influence the level of gene expression. Some isolated promoter sequences can provide for gene expression of heterologous DNAs, that is a DNA different from the native or homologous DNA.

Promoter sequences are also known to be strong or weak, or inducible. A strong promoter provides for a high level of gene expression, whereas a weak promoter provides a very low level of gene expression. An inducible promoter is a promoter that provides for the turning on and off of gene expression in response to an exogenously added agent, or to an environmental or developmental stimulus. For example, a bacterial promoter such as the $P_{tac}$ promoter can be induced to vary levels of gene expression depending on the level of isothiopropylgalactoside added to the transformed cells. Promoters can also provide for tissue specific or developmental regulation. An isolated promoter sequence that is a strong promoter for heterologous DNAs is advantageous because it provides for a sufficient level of gene expression for easy detection and selection of transformed cells and provides for a high level of gene expression when desired. In some embodiments, the promoter is an inducible promoter and/or a tissue-specific promoter.

Examples of promoters that can be used include, but are not limited to, the CaMV 35S promoter (Odell et al., Nature. 313:810-812 (1985)), or others such as CaMV 19S (Lawton et al., *Plant Molecular Biology.* 9:315-324 (1987)), nos (Ebert et al., *Proc. Natl. Acad. Sci. USA.* 84:5745-5749 (1987)), Adh1 (Walker et al., *Proc. Natl. Acad. Sci. USA.* 84:6624-6628 (1987)), sucrose synthase (Yang et al., *Proc. Natl. Acad. Sci. USA.* 87:4144-4148 (1990)), α-tubulin, ubiquitin, actin (Wang et al., *Mol. Cell. Biol.* 12:3399 (1992)), cab (Sullivan et al., *Mol. Gen. Genet.* 215:431 (1989)), PEPCase (Hudspeth et al., *Plant Molecular Biology.* 12:579-589 (1989)), the CCR (cinnamoyl CoA:NADP oxidoreductase, EC 1.2.1.44) promoter sequence isolated from *Lollium perenne*, (or a perennial ryegrass) and/or those associated with the R gene complex (Chandler et al., *The Plant Cell.* 1:1175-1183 (1989)). Further suitable promoters include the poplar xylem-specific secondary cell wall specific cellulose synthase 8 promoter, cauliflower mosaic virus promoter, the Z10 promoter from a gene encoding a 10 kD zein protein, a Z27 promoter from a gene encoding a 27 kD zein protein, inducible promoters, such as the light inducible promoter derived from the pea rbcS gene (Coruzzi et al., *EMBO J.* 3:1671 (1971)) and the actin promoter from rice (McElroy et al., *The Plant Cell.* 2:163-171 (1990)). Seed specific promoters, such as the phaseolin promoter from beans, may also be used (Sengupta-Gopalan, *Proc. Natl. Acad. Sci. USA.* 83:3320-3324 (1985). Other promoters useful in the practice of the invention are known to those of skill in the art.

Alternatively, novel tissue specific promoter sequences may be employed in the practice of the present invention. cDNA clones from a particular tissue are isolated and those clones which are expressed specifically in that tissue are identified, for example, using Northern blotting. Preferably, the gene isolated is not present in a high copy number, but is relatively abundant in specific tissues. The promoter and control elements of corresponding genomic clones can then be localized using techniques well known to those of skill in the art.

For example, the promoter can be an inducible promoter. Such inducible promoters can be activated by agents such as chemicals, hormones, sugars, metabolites, or by the age or developmental stage of the plant. For example, the promoter can be an ethanol-inducible promoter, a sugar-inducible promoter, a senescence-induced promoter or any promoter activated in vegetative tissues of dicots and monocots. One example of a sugar-inducible promoter is a patatin B33 promoter. Such a patatin B33 promoter can, for example, be used in tuber crops such as cassava, potato, rutabaga, sugar beet, and the like. An example of a sequence for the patatin B33 promoter is as follows (SEQ ID NO:20).

```
  1 AAGCTTATGT TGCCATATAG AGTAGTTTGT GATGGTATAC

41 TTCATAAACT TTAACTTATG TTAAATTTGT AATGATAAAA

81 TTTTTATTGT AAATTAAAAA TTACTTATAA AATTGGGCAT

121 TATAACATAT GAAAGACAAA TTGTGTTACA TATTTTACTT

161 TTGACTTTAA TATGAATATT TCAATTTAAA TCATTGTTTT

201 ATTTTCTCTT TCTTTTTACA GGTATAAAAG GTGAAAATTG

241 AAGCAAGATT GATTGCAAGC TATGTGTCAC CACGTTATTG

281 ATACTTTGGA AGAAATTTTT ACTTATATGT CTTTGTTTAG

321 GAGTAATATT TGATATGTTT TAGTTAGATT TTCTTGTCAT

361 TTATGCTTTA GTATAATTTT AGTTATTTTT ATTATATGAT
```

-continued
```
401 CATGGGTGAA TTTTGATACA AATATTTTTG TCATTAAATA

441 AATTAATTTA TCACAACTTG ATTACTTTCA GTGACAAAAA

481 ATGTATTGTC GTAGTACCCT TTTTTGTTGA ATATGAATAA

521 TTTTTTTTAT TTTGTGACAA TTGTAATTGT CACTACTTAT

561 GATAATATTT AGTGACATAT ATGTCGTCGG TAAAAGCAAA

601 CACTTTCAGT GACAAAATAA TAGATTTAAT CACAAAATTA

641 TTAACCTTTT TTATAATAAT AAATTTATCC CTAATTTATA

681 CATTTAAGGA CAAAGTATTT TTTTTATATA TAAAAAATAG

721 TCTTTAGTGA CGATCGTAGT GTTGAGTCTA GAAATCATAA

761 TGTTGAATCT AGAAAAATCT CATGCAGTGT AAAATAAACC

801 TCAAAAAGGA CGTTCAGTCC ATAGAGGGGG TGTATGTGAC

841 ACCCCAACCT CAGCAAAAGA AAACCTCCCT TCAACAAGGA

881 CATTTGCGGT GCTAAACAAT TTCAAGTCTC ATCACACATA

921 TATTTATTAT ATAATACTAA TAAAGAATAG AAAAGGAAAG

961 GTAAACATCA TTAAATCGTC TTTGTATATT TTTAGTGACA

1001 ACTGATTGAC GAAATCTTTT TCGTCACACA AAATTTTTAG

1041 TGACGAAACA TGATTTATAG ATGATGAAAT TATTTGTCCC

1081 TCATAATCTA ATTTGTTGTA GTGATCATTA CTCCTTTGTT

1121 TGTTTTATTT GTCATGTTAG TCCATTAAAA AAAAATATCT

1161 CTCTTCTTAT GTACGTGAAT GGTTGGAACG GATCTATTAT

1201 ATAATACTAA TAAAGAATAG AAAAAGGAAA GTGAGTGAGG

1241 TTCGAGGGAG AGAATCTGTT TAATATCAGA GTCGATCATG

1281 TGTCAATTTT ATCGATATGA CCCTAACTTC AACTGAGTTT

1321 AACCAATTCC GATAAGGCGA GAAATATCAT AGTATTGAGT

1361 CTAGAAAAAT CTCATGTAGT GTGGGGTAAA CCTCAGCAAG

1401 GACGTTGAGT CCATAGAGGG GGGTGTATGT GACACCCCAA

1441 CCTCAGCAAA AGAAAACCTC CCCTCAAGAA GGACATTTGC

1481 GGTGCTAAAC AATTTCAAGT CTCATCACAC ATATATATAT

1521 ATTATATAAT ACTAATAAAT AATAGAAAAA GGAAAGGTAA

1561 ACATCACTAA CGACAGTTGC GGTGCAAACT GAGTGAGGTA

1601 ATAAACATCA CTAACTTTTA TTGGTTATGT CAAACTCAAA

1641 GTAAAATTTC TCAACTTGTT TACGTGCCTA TATATACCAT

1681 GCTTGTTATA TGCTCAAAGC ACCAACAAAA TTTAAAAACA

1721 CTTTGAACAT TTGCAAAATG GCAACTACTA AAACTTTTTT

1761 AATTTTATTT TTTATGATAT TAGCAACTAC TAGTTCAACA

1801 TGTGCTAAGT TGGAAGAAAT GGTTACTGTT CTAAGTATTG

1841 ATGGAGGTGG AATTAAGGGA ATCATTCCAG CTATCATTCT

1881 CGAATTTCTT GAAGGACAAC TTCAGGTATT GTAAAAATAT

1921 TTTTTAATGT ATGTGCGTAA GTGTGACACT ACTACTATAG

1961 TCATTCTGGG TACCT
```

An ADP-glucose pyrophosphorylase inhibitory nucleic acid and/or a WRINKLED1 nucleic acid can be combined with the promoter by standard methods to yield an expression cassette, for example, as described in Sambrook et al. (MOLECULAR CLONING: A LABORATORY MANUAL. Second Edition (Cold Spring Harbor, N.Y.: Cold Spring Harbor Press (1989); MOLECULAR CLONING: A LABORATORY MANUAL. Third Edition (Cold Spring Harbor, N.Y.: Cold Spring Harbor Press (2000)). Briefly, a plasmid containing a promoter such as the 35S CaMV promoter can be constructed as described in Jefferson (*Plant Molecular Biology Reporter* 5:387-405 (1987)) or obtained from Clontech Lab in Palo Alto, Calif. (e.g., pBI121 or pBI221). Typically, these plasmids are constructed to have multiple cloning sites having specificity for different restriction enzymes downstream from the promoter. The ADP-glucose pyrophosphorylase inhibitory nucleic acid and/or WRINKLED1 nucleic acids can be subcloned downstream from the promoter using restriction enzymes and positioned to ensure that the DNA is inserted in proper orientation with respect to the promoter so that the DNA can be expressed as sense or antisense RNA. Once the ADP-glucose pyrophosphorylase inhibitory nucleic acid and/or the WRINKLED1 nucleic acid is operably linked to a promoter, the expression cassette so formed can be subcloned into a plasmid or other vector (e.g., an expression vector).

In some embodiments, a cDNA clone encoding a selected WRINKLED1 protein is isolated from vegetative tissue (e.g., stems, roots, and/or leaves). The cDNA clone encoding a selected WRINKLED1 protein can be isolated from mature plants. In other embodiments, cDNA clones from other species (that encode a WRINKLED1 protein) are isolated from selected plant tissues, or a nucleic acid encoding a mutant or modified WRINKLED1 protein is prepared by available methods or as described herein. For example, the nucleic acid encoding a mutant or modified WRINKLED1 protein can be any nucleic acid with a coding region that hybridizes, for example, to SEQ ID NO:8, 10, 12, 14, 18 and that has WRINKLED1 transcription factor activity.

Using restriction endonucleases, the ADP-glucose pyrophosphorylase inhibitory nucleic acid and/or the entire coding sequence for the WRINKLED1 is subcloned downstream of the promoter in a 5' to 3' sense orientation.

Targeting Sequences:

Additionally, expression cassettes can be constructed and employed to target the ADP-glucose pyrophosphorylase inhibitory nucleic acids and/or WRINKLED1 nucleic acids to an intracellular compartment within plant cells or to direct an encoded protein to the extracellular environment. This can generally be achieved by joining a DNA sequence encoding a transit or signal peptide sequence to the coding sequence of the ADP-glucose pyrophosphorylase inhibitory nucleic acid and/or WRINKLED1 nucleic acid. The resultant transit, or signal, peptide will transport the protein to a particular intracellular, or extracellular destination, respectively, and can then be posttranslational removed. Transit peptides act by facilitating the transport of proteins through intracellular membranes, e.g., vacuole, vesicle, plastid and mitochondrial membranes, whereas signal peptides direct proteins through the extracellular membrane. By facilitating transport of the protein into compartments inside or outside the cell, these sequences can increase the accumulation of a particular gene product in a particular location. For example, see U.S. Pat. No. 5,258,300.

3' Sequences:

When the expression cassette is to be introduced into a plant cell, the expression cassette can also optionally include 3' nontranslated plant regulatory DNA sequences that act as a signal to terminate transcription and allow for the polyadenylation of the resultant mRNA. The 3' nontranslated regulatory DNA sequence preferably includes from about 300 to 1,000 nucleotide base pairs and contains plant transcriptional and translational termination sequences. For example, 3' elements that can be used include those derived from the nopaline synthase gene of *Agrobacterium tumefaciens* (Bevan et al., *Nucleic Acid Research.* 11:369-385 (1983)), or the terminator sequences for the T7 transcript from the octopine synthase gene of *Agrobacterium tumefaciens*, and/or the 3' end of the protease inhibitor I or II genes from potato or tomato. Other 3' elements known to those of skill in the art can also be employed. These 3' nontranslated regulatory sequences can be obtained as described in An (*Methods in Enzymology.* 153:292 (1987)). Many such 3' nontranslated regulatory sequences are already present in plasmids available from commercial sources such as Clontech, Palo Alto, Calif. The 3' nontranslated regulatory sequences can be operably linked to the 3' terminus of the ADP-glucose pyrophosphorylase inhibitory nucleic acids and/or WRINKLED1 nucleic acids by standard methods.

Selectable and Screenable Marker Sequences: In order to improve identification of transformants, a selectable or screenable marker gene can be employed with the ADP-glucose pyrophosphorylase inhibitory nucleic acids and/or the WRINKLED1 nucleic acids. "Marker genes" are genes that impart a distinct phenotype to cells expressing the marker gene and thus allow such transformed cells to be distinguished from cells that do not have the marker. Such genes may encode either a selectable or screenable marker, depending on whether the marker confers a trait which one can 'select' for by chemical means, i.e., through the use of a selective agent (e.g., a herbicide, antibiotic, or the like), or whether it is simply a trait that one can identify through observation or testing, i.e., by 'screening' (e.g., the R-locus trait). Of course, many examples of suitable marker genes are known to the art and can be employed in the practice of the invention.

Included within the terms selectable or screenable marker genes are also genes which encode a "secretable marker" whose secretion can be detected as a means of identifying or selecting for transformed cells. Examples include markers which encode a secretable antigen that can be identified by antibody interaction, or secretable enzymes that can be detected by their catalytic activity. Secretable proteins fall into a number of classes, including small, diffusible proteins detectable, e.g., by ELISA; and proteins that are inserted or trapped in the cell wall (e.g., proteins that include a leader sequence such as that found in the expression unit of extensin or tobacco PR-S).

With regard to selectable secretable markers, the use of a gene that encodes a polypeptide that becomes sequestered in the cell wall, where the polypeptide includes a unique epitope may be advantageous. Such a secreted antigen marker can employ an epitope sequence that would provide low background in plant tissue, a promoter-leader sequence that imparts efficient expression and targeting across the plasma membrane, and can produce protein that is bound in the cell wall and yet is accessible to antibodies. A normally secreted wall protein modified to include a unique epitope would satisfy such requirements.

Examples of proteins suitable for modification in this manner include extensin or hydroxyproline rich glycoprotein (HPRG). For example, the maize HPRG (Stiefel et al., *The Plant Cell.* 2:785-793 (1990)) is well characterized in terms of molecular biology, expression, and protein structure and therefore can readily be employed. However, any one of a variety of extensins and/or glycine-rich wall proteins (Keller et al., *EMBO J.* 8:1309-1314 (1989)) could be modified by the addition of an antigenic site to create a screenable marker.

Possible selectable markers for use in connection with the present invention include, but are not limited to, a neo gene (Potrykus et al., *Mol. Gen. Genet.* 199:183-188 (1985)) which codes for kanamycin resistance and can be selected for using kanamycin, G418, and the like; a bar gene which codes for bialaphos resistance; a gene which encodes an altered EPSP synthase protein (Hinchee et al., *Bio/Technology.* 6:915-922 (1988)) thus conferring glyphosate resistance; a nitrilase gene such as bxn from *Klebsiella ozaenae* which confers resistance to bromoxynil (Stalker et al., *Science.* 242:419-423 (1988)); a mutant acetolactate synthase gene (ALS) which confers resistance to imidazolinone, sulfonylurea or other ALS-inhibiting chemicals (European Patent Application 154,204 (1985)); a methotrexate-resistant DHFR gene (Thillet et al., *J. Biol. Chem.* 263:12500-12508 (1988)); a dalapon dehalogenase gene that confers resistance to the herbicide dalapon; or a mutated anthranilate synthase gene that confers resistance to 5-methyl tryptophan. Where a mutant EPSP synthase gene is employed, additional benefit may be realized through the incorporation of a suitable chloroplast transit peptide, CTP (European Patent Application 0 218 571 (1987)).

An illustrative embodiment of a selectable marker gene capable of being used in systems to select transformants is the gene that encode the enzyme phosphinothricin acetyltransferase, such as the bar gene from *Streptomyces hygroscopicus* or the pat gene from *Streptomyces viridochromogenes* (U.S. Pat. No. 5,550,318). The enzyme phosphinothricin acetyl transferase (PAT) inactivates the active ingredient in the herbicide bialaphos, phosphinothricin (PPT). PPT inhibits glutamine synthetase, (Murakami et al., *Mol. Gen. Genet.* 205:42-50 (1986); Twell et al., *Plant Physiol.* 91:1270-1274 (1989)) causing rapid accumulation of ammonia and cell death. The success in using this selective system in conjunction with monocots was surprising because of the major difficulties that have been reported in transformation of cereals (Potrykus, *Trends Biotech.* 7:269-273 (1989)).

Screenable markers that may be employed include, but are not limited to, a β-glucuronidase or uidA gene (GUS) that encodes an enzyme for which various chromogenic substrates are known; an R-locus gene, which encodes a product that regulates the production of anthocyanin pigments (red color) in plant tissues (Dellaporta et al., In: *Chromosome Structure and Function: Impact of New Concepts*, 18$^{th}$ Stadler Genetics Symposium, J. P. Gustafson and R. Appels, eds. (New York: Plenum Press) pp. 263-282 (1988)); a β-lactamase gene (Sutcliffe, *Proc. Natl. Acad. Sci. USA.* 75:3737-3741 (1978)), which encodes an enzyme for which various chromogenic substrates are known (e.g., PADAC, a chromogenic cephalosporin; a xylE gene (Zukowsky et al., *Proc. Natl. Acad. Sci. USA.* 80:1101 (1983)) which encodes a catechol dioxygenase that can convert chromogenic catechols; an α-amylase gene (Ikuta et al., *Bio/technology* 8:241-242 (1990)); a tyrosinase gene (Katz et al., *J. Gen. Microbiol.* 129:2703-2714 (1983)) which encodes an enzyme capable of oxidizing tyrosine to DOPA and dopaquinone which in turn condenses to form the easily detectable compound melanin; a 3-galactosidase gene, which encodes an enzyme for which there are chromogenic substrates; a luciferase (lux) gene (Ow et al., *Science.* 234:856-859.1986), which allows for bioluminescence detection; or an aequorin gene (Prasher et al., *Biochem.*

*Biophys. Res. Comm.* 126:1259-1268 (1985)), which may be employed in calcium-sensitive bioluminescence detection, or a green or yellow fluorescent protein gene (Niedz et al., *Plant Cell Reports.* 14:403 (1995)).

For example, genes from the maize R gene complex can be used as screenable markers. The R gene complex in maize encodes a protein that acts to regulate the production of anthocyanin pigments in most seed and plant tissue. Maize strains can have one, or as many as four, R alleles that combine to regulate pigmentation in a developmental and tissue specific manner. A gene from the R gene complex does not harm the transformed cells. Thus, an R gene introduced into such cells will cause the expression of a red pigment and, if stably incorporated, can be visually scored as a red sector. If a maize line carries dominant alleles for genes encoding the enzymatic intermediates in the anthocyanin biosynthetic pathway (C2, A1, A2, Bz1 and Bz2), but carries a recessive allele at the R locus, transformation of any cell from that line with R will result in red pigment formation. Exemplary lines include Wisconsin 22 that contains the rg-Stadler allele and TR112, a K55 derivative that is r-g, b, Pl. Alternatively any genotype of maize can be utilized if the C1 and R alleles are introduced together.

The R gene regulatory regions may be employed in chimeric constructs in order to provide mechanisms for controlling the expression of chimeric genes. More diversity of phenotypic expression is known at the R locus than at any other locus (Coe et al., in *Corn and Corn Improvement*, eds. Sprague, G. F. & Dudley, J. W. (Am. Soc. Agron., Madison, Wis.), pp. 81-258 (1988)). It is contemplated that regulatory regions obtained from regions 5' to the structural R gene can be useful in directing the expression of genes, e.g., insect resistance, drought resistance, herbicide tolerance or other protein coding regions. In some embodiments, any of the various R gene family members may be successfully employed (e.g., P, S, Lc, etc.). However, one that can be used is Sn (particularly Sn: bol3). Sn is a dominant member of the R gene complex and is functionally similar to the R and B loci in that Sn controls the tissue specific deposition of anthocyanin pigments in certain seedling and plant cells, therefore, its phenotype is similar to R.

A further screenable marker contemplated for use in the present invention is firefly luciferase, encoded by the lux gene. The presence of the lux gene in transformed cells may be detected using, for example, X-ray film, scintillation counting, fluorescent spectrophotometry, low-light video cameras, photon counting cameras or multiwell luminometry. It is also envisioned that this system may be developed for population screening for bioluminescence, such as on tissue culture plates, or even for whole plant screening.

Elements of the present disclosure are exemplified through the use of particular marker genes. However in light of this disclosure, numerous other possible selectable and/or screenable marker genes will be apparent to those of skill in the art in addition to the one set forth herein below. Therefore, it will be understood that the discussion provided herein is exemplary rather than exhaustive. In light of the techniques disclosed herein and the general recombinant techniques that are known in the art, the present invention readily allows the introduction of any gene, including marker genes, into a recipient cell to generate a transformed plant cell, e.g., a monocot cell or dicot cell.

Other Optional Sequences:

An expression cassette of the invention can also further comprise plasmid DNA. Plasmid vectors include additional DNA sequences that provide for easy selection, amplification, and transformation of the expression cassette in prokaryotic and eukaryotic cells, e.g., pUC-derived vectors such as pUC8, pUC9, pUC18, pUC19, pUC23, pUC119, and pUC120, pSK-derived vectors, pGEM-derived vectors, pSP-derived vectors, or pBS-derived vectors. The additional DNA sequences include origins of replication to provide for autonomous replication of the vector, additional selectable marker genes, such as antibiotic or herbicide resistance, unique multiple cloning sites providing for multiple sites to insert DNA sequences, and/or sequences that enhance transformation of prokaryotic and eukaryotic cells.

Another vector that is useful for expression in both plant and prokaryotic cells is the binary Ti plasmid (as disclosed in Schilperoort et al., U.S. Pat. No. 4,940,838) as exemplified by vector pGA582. This binary Ti plasmid vector has been previously characterized by An (*Methods in Enzymology*. 153:292 (1987)). This binary Ti vector can be replicated in prokaryotic bacteria such as *E. coli* and *Agrobacterium*. The *Agrobacterium* plasmid vectors can be used to transfer the expression cassette to dicot plant cells and under certain conditions to monocot cells, such as rice cells. The binary Ti vectors preferably include the nopaline T DNA right and left borders to provide for efficient plant cell transformation, a selectable marker gene, unique multiple cloning sites in the T border regions, the colE1 replication of origin and a wide host range replicon. The binary Ti vectors carrying an expression cassette of the invention can be used to transform both prokaryotic and eukaryotic cells, but is preferably used to transform dicot plant cells.

In Vitro Screening of Expression Cassettes:

Once the expression cassette is constructed and subcloned into a suitable plasmid, it can be screened for the ability to express the encoded WRINKLED1 transcription factor(s) and/or to substantially inhibit the translation of an mRNA coding the ADP-glucose pyrophosphorylase by standard methods. For example, for hybrid selection or arrested translation of ADP-glucose pyrophosphorylase mRNA, a preselected inhibitory nucleic acid sequence can be subcloned into a selected expression cassette or vector (e.g., a SP6/T7 containing plasmid, which is supplied by ProMega Corp.). For transformation of plants cells, suitable vectors include plasmids such as described herein. For example, hybrid arrest translation is an in vitro assay that measures the inhibition of translation of an mRNA encoding the WRINKLED1. This screening method can also be used to select and identify more effective ADP-glucose pyrophosphorylase inhibitory nucleic acid. As a control, a nonsense nucleic acid is expressed from an expression cassette that is introduced into plants or plants cells. The phenotypes of the control and test cells or plants can also be assessed.

DNA Delivery of the DNA Molecules into Host Cells:

The present invention generally includes steps directed to introducing an ADP-glucose pyrophosphorylase inhibitory nucleic acid and/or a WRINKLED1 nucleic acid into a recipient cell to create a transformed cell. The frequency of occurrence of cells taking up exogenous (foreign) DNA may be low. Moreover, it is most likely that not all recipient cells receiving DNA segments or sequences will result in a transformed cell wherein the DNA is stably integrated into the plant genome and/or expressed. Some may show only initial and transient gene expression. However, certain cells from virtually any dicot or monocot species may be stably transformed, and these cells regenerated into transgenic plants, through the application of the techniques disclosed herein.

Another aspect of the invention is a plant species with increased vegetative tissue oil content, wherein the plant has an introduced inhibitory nucleic acid and/or an introduced WRINKLED1 nucleic acid. The plant can be a monocotyledon or a dicotyledon. Another aspect of the invention includes plant cells (e.g., embryonic cells or other cell lines) that can regenerate fertile transgenic plants and/or seeds. The cells can be derived from either monocotyledons or dicotyledons. The cell(s) may be in a suspension cell culture or may be in an intact plant part, such as an immature embryo, or in a specialized plant tissue, such as callus, such as Type I or Type II callus.

Examples of plants and/or plant cells that can be modified as described herein include alfalfa (e.g., forage legume alfalfa), algae, avocado, barley, broccoli, Brussels sprouts, cabbage, canola, cassava, cauliflower, cole vegetables, collards, crucifers, grain legumes, grasses (e.g., forage grasses), jatropa, kale, kohlrabi, maize, miscanthus, mustards, nut sedge, oats, oil firewood trees, oilseeds, potato, radish, rice, rutabaga, sorghum, soybean, sugar beets, sugarcane, sunflower, switchgrass, tobacco, tomato, turnips, and wheat. In some embodiments, the plant is a *Brassicaceae* or other *Solanaceae* species. In some embodiments, the plant or cell can be a maize plant or cell. In some embodiments, the plant is not a species of *Arabidopsis*, for example, in some embodiments the plant is not *Arabidopsis thaliana*.

Transformation of the cells of the plant tissue source can be conducted by any one of a number of methods known to those of skill in the art. Examples are: Transformation by direct DNA transfer into plant cells by electroporation (U.S. Pat. No. 5,384,253 and U.S. Pat. No. 5,472,869, Dekeyser et al., *The Plant Cell*. 2:591-602 (1990)); direct DNA transfer to plant cells by PEG precipitation (Hayashimoto et al., *Plant Physiol*. 93:857-863 (1990)); direct DNA transfer to plant cells by microprojectile bombardment (McCabe et al., *Bio/Technology*. 6:923-926 (1988); Gordon-Kamm et al., *The Plant Cell*. 2:603-618 (1990); U.S. Pat. No. 5,489,520; U.S. Pat. No. 5,538,877; and U.S. Pat. No. 5,538,880) and DNA transfer to plant cells via infection with *Agrobacterium*. Methods such as microprojectile bombardment or electroporation can be carried out with "naked" DNA where the expression cassette may be simply carried on any *E. coli*-derived plasmid cloning vector. In the case of viral vectors, it is desirable that the system retain replication functions, but lack functions for disease induction.

One method for dicot transformation, for example, involves infection of plant cells with *Agrobacterium tumefaciens* using the leaf-disk protocol (Horsch et al., *Science* 227:1229-1231 (1985). Monocots such as *Zea mays* can be transformed via microprojectile bombardment of embryogenic callus tissue or immature embryos, or by electroporation following partial enzymatic degradation of the cell wall with a pectinase-containing enzyme (U.S. Pat. No. 5,384,253; and U.S. Pat. No. 5,472,869). For example, embryogenic cell lines derived from immature *Zea mays* embryos can be transformed by accelerated particle treatment as described by Gordon-Kamm et al. (*The Plant Cell*. 2:603-618 (1990)) or U.S. Pat. No. 5,489,520; U.S. Pat. No. 5,538,877 and U.S. Pat. No. 5,538,880, cited above. Excised immature embryos can also be used as the target for transformation prior to tissue culture induction, selection and regeneration as described in U.S. application Ser. No. 08/112,245 and PCT publication WO 95/06128. Furthermore, methods for transformation of monocotyledonous plants utilizing *Agrobacterium tumefaciens* have been described by Hiei et al. (European Patent 0 604 662, 1994) and Saito et al. (European Patent 0 672 752, 1995).

Methods such as microprojectile bombardment or electroporation are carried out with "naked" DNA where the expression cassette may be simply carried on any *E. coli*- derived plasmid cloning vector. In the case of viral vectors, it is desirable that the system retain replication functions, but lack functions for disease induction.

The choice of plant tissue source for transformation will depend on the nature of the host plant and the transformation protocol. Useful tissue sources include callus, suspension culture cells, protoplasts, leaf segments, stem segments, tassels, pollen, embryos, hypocotyls, tuber segments, meristematic regions, and the like. The tissue source is selected and transformed so that it retains the ability to regenerate whole, fertile plants following transformation, i.e., contains totipotent cells. Type I or Type II embryonic maize callus and immature embryos are preferred Zea mays tissue sources. Selection of tissue sources for transformation of monocots is described in detail in U.S. application Ser. No. 08/112,245 and PCT publication WO 95/06128.

The transformation is carried out under conditions directed to the plant tissue of choice. The plant cells or tissue are exposed to the DNA or RNA carrying the PMT inhibitory nucleic acid(s) and/or the WRINKLED1 nucleic acids for an effective period of time. This may range from a less than one second pulse of electricity for electroporation to a 2-3 day co-cultivation in the presence of plasmid-bearing Agrobacterium cells. Buffers and media used will also vary with the plant tissue source and transformation protocol. Many transformation protocols employ a feeder layer of suspended culture cells (e.g., tobacco or Black Mexican Sweet corn, for example) on the surface of solid media plates, separated by a sterile filter paper disk from the plant cells or tissues being transformed.

Electroporation:

Where one wishes to introduce DNA by means of electroporation, it is contemplated that the method of Krzyzek et al. (U.S. Pat. No. 5,384,253) may be advantageous. In this method, certain cell wall-degrading enzymes, such as pectin-degrading enzymes, are employed to render the target recipient cells more susceptible to transformation by electroporation than untreated cells. Alternatively, recipient cells can be made more susceptible to transformation, by mechanical wounding.

To effect transformation by electroporation, one may employ either friable tissues such as a suspension cell cultures, or embryogenic callus, or alternatively, one may transform immature embryos or other organized tissues directly. The cell walls of the preselected cells or organs can be partially degraded by exposing them to pectin-degrading enzymes (pectinases or pectolyases) or mechanically wounding them in a controlled manner. Such cells would then be receptive to DNA uptake by electroporation, which may be carried out at this stage, and transformed cells then identified by a suitable selection or screening protocol dependent on the nature of the newly incorporated DNA.

Microprojectile Bombardment:

A further advantageous method for delivering transforming DNA segments to plant cells is microprojectile bombardment. In this method, microparticles may be coated with DNA and delivered into cells by a propelling force. Exemplary particles include those comprised of tungsten, gold, platinum, and the like.

It is contemplated that in some instances DNA precipitation onto metal particles would not be necessary for DNA delivery to a recipient cell using microprojectile bombardment. In an illustrative embodiment, non-embryogenic Black Mexican Sweet (BMS) cells are bombarded with intact cells of the bacteria E. coli or Agrobacterium tumefaciens containing plasmids with either the ADP-glucose pyrophosphorylase inhibitory nucleic acid and/or the WRINKLED1 nucleic acid engineered for expression in maize. Bacteria were inactivated by ethanol dehydration prior to bombardment. A low level of transient expression of the WRINKLED1 gene and/or the inhibitory nucleic acid may be observed 24-48 hours following DNA delivery. In addition, stable transformants containing the WRINKLED1 gene and/or the inhibitory nucleic acid are recovered following bombardment with either E. coli or Agrobacterium tumefaciens cells. It is contemplated that particles may contain DNA rather than be coated with DNA. Hence particles may increase the level of DNA delivery but are not, in and of themselves, necessary to introduce DNA into plant cells.

An advantage of microprojectile bombardment, in addition to it being an effective means of reproducibly stably transforming monocots, is that the isolation of protoplasts (Christou et al., PNAS. 84:3962-3966 (1987)), the formation of partially degraded cells, or the susceptibility to Agrobacterium infection is not required. An illustrative embodiment of a method for delivering DNA into maize cells by acceleration is a Biolistics Particle Delivery System, which can be used to propel particles coated with DNA or cells through a screen, such as a stainless steel or Nytex screen, onto a filter surface covered with maize cells cultured in suspension (Gordon-Kamm et al., The Plant Cell. 2:603-618 (1990)). The screen disperses the particles so that they are not delivered to the recipient cells in large aggregates. It is believed that a screen intervening between the projectile apparatus and the cells to be bombarded reduces the size of projectile aggregate and may contribute to a higher frequency of transformation, by reducing damage inflicted on the recipient cells by an aggregated projectile.

For bombardment, cells in suspension are preferably concentrated on filters or solid culture medium. Alternatively, immature embryos or other target cells may be arranged on solid culture medium. The cells to be bombarded are positioned at an appropriate distance below the macroprojectile stopping plate. If desired, one or more screens are also positioned between the acceleration device and the cells to be bombarded. Through the use of techniques set forth here-in one may obtain up to 1000 or more foci of cells transiently expressing a marker gene. The number of cells in a focus which express the exogenous gene product 48 hours post-bombardment often range from about 1 to 10 and average about 1 to 3.

In bombardment transformation, one may optimize the prebombardment culturing conditions and the bombardment parameters to yield the maximum numbers of stable transformants. Both the physical and biological parameters for bombardment can influence transformation frequency. Physical factors are those that involve manipulating the DNA/microprojectile precipitate or those that affect the path and velocity of either the macro- or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmid DNA.

One may wish to adjust various bombardment parameters in small scale studies to fully optimize the conditions and/or to adjust physical parameters such as gap distance, flight distance, tissue distance, and helium pressure. One may also minimize the trauma reduction factors (TRFs) by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation. Execution of such routine adjustments will be known to those of skill in the art.

An Example of Production and Characterization of Stable Transgenic Maize:

After effecting delivery of one or more ADP-glucose pyrophosphorylase inhibitory nucleic acid(s) and/or WRINKLED1 nucleic acid(s) to recipient cells by any of the methods discussed above (e.g., in an expression vector), the transformed cells can be identified for further culturing and plant regeneration. As mentioned above, in order to improve the ability to identify transformants, one may desire to employ a selectable or screenable marker gene as, or in addition to, the ADP-glucose pyrophosphorylase inhibitory nucleic acids and/or WRINKLED1 nucleic acids. In this case, one would then generally assay the potentially transformed cell population by exposing the cells to a selective agent or agents, or one would screen the cells for the desired marker gene trait. Alternatively, the introduced (e.g., transgenic) nucleic acids can be detected and/or characterized by use of a nucleic acid probe to detect the presence of an expression cassette and/or expressed RNA. The introduced nucleic acids can also be detected and/or evaluated by sequencing.

Selection:

An exemplary embodiment of methods for identifying transformed cells involves exposing the bombarded cultures to a selective agent, such as a metabolic inhibitor, an antibiotic, herbicide or the like. Cells which have been transformed and have stably integrated a marker gene conferring resistance to the selective agent used, will grow and divide in culture. Sensitive cells will not be amenable to further culturing.

For example, to use the bar-bialaphos or the EPSPS-glyphosate selective system, bombarded tissue is cultured for about 0-28 days on nonselective medium and subsequently transferred to medium containing from about 1-3 mg/l bialaphos or about 1-3 mM glyphosate, as appropriate. While ranges of about 1-3 mg/l bialaphos or about 1-3 mM glyphosate can be employed, it is proposed that ranges of at least about 0.1-50 mg/l bialaphos or at least about 0.1-50 mM glyphosate may be useful. Tissue can be placed on any porous, inert, solid or semi-solid support for bombardment, including but not limited to filters and solid culture medium. Bialaphos and glyphosate are provided as examples of agents suitable for selection of transformants, but the technique of this invention is not limited to them.

An example of a screenable marker trait is the red pigment produced under the control of the R-locus in maize. This pigment may be detected by culturing cells on a solid support containing nutrient media capable of supporting growth at this stage and selecting cells from colonies (visible aggregates of cells) that are pigmented. These cells may be cultured further, either in suspension or on solid media. The R-locus is useful for selection of transformants from bombarded immature embryos. In a similar fashion, the introduction of the C1 and B genes will result in pigmented cells and/or tissues.

The enzyme luciferase is also useful as a screenable marker in the context of the present invention. In the presence of the substrate luciferin, cells expressing luciferase emit light which can be detected on photographic or X-ray film, in a luminometer (or liquid scintillation counter), by devices that enhance night vision, or by a highly light sensitive video camera, such as a photon counting camera. All of these assays are nondestructive and transformed cells may be cultured further following identification. The photon counting camera is especially valuable as it allows one to identify specific cells or groups of cells which are expressing luciferase and manipulate those in real time.

It is further contemplated that combinations of screenable and selectable markers may be useful for identification of transformed cells. For example, selection with a growth inhibiting compound, such as bialaphos or glyphosate at concentrations below those that cause 100% inhibition followed by screening of growing tissue for expression of a screenable marker gene such as luciferase would allow one to recover transformants from cell or tissue types that are not amenable to selection alone. In one example, embryogenic Type II callus of $Zea\ mays$ L. can be selected with sub-lethal levels of bialaphos. Slowly growing tissue was subsequently screened for expression of the luciferase gene and transformants can be identified.

Regeneration and Seed Production:

Cells that survive the exposure to the selective agent, or cells that have been scored positive in a screening assay, are cultured in media that supports regeneration of plants. One example of a growth regulator that can be used for such purposes is dicamba or 2,4-D. However, other growth regulators may be employed, including NAA, NAA+2,4-D or perhaps even picloram. Media improvement in these and like ways can facilitate the growth of cells at specific developmental stages. Tissue can be maintained on a basic media with growth regulators until sufficient tissue is available to begin plant regeneration efforts, or following repeated rounds of manual selection, until the morphology of the tissue is suitable for regeneration, at least two weeks, then transferred to media conducive to maturation of embryoids. Cultures are typically transferred every two weeks on this medium. Shoot development signals the time to transfer to medium lacking growth regulators.

The transformed cells, identified by selection or screening and cultured in an appropriate medium that supports regeneration, can then be allowed to mature into plants. Developing plantlets are transferred to soilless plant growth mix, and hardened, e.g., in an environmentally controlled chamber at about 85% relative humidity, about 600 ppm $CO_2$, and at about 25-250 microeinsteins/sec·m$^2$ of light. Plants can be matured either in a growth chamber or greenhouse. Plants are regenerated from about 6 weeks to 10 months after a transformant is identified, depending on the initial tissue. During regeneration, cells are grown on solid media in tissue culture vessels. Illustrative embodiments of such vessels are petri dishes and Plant Con™. Regenerating plants can be grown at about 19° C. to 28° C. After the regenerating plants have reached the stage of shoot and root development, they may be transferred to a greenhouse for further growth and testing.

Mature plants are then obtained from cell lines that express the desired trait(s). In some embodiments, the regenerated plants are self pollinated. In addition, pollen obtained from the regenerated plants can be crossed to seed grown plants of agronomically important inbred lines. In some cases, pollen from plants of these inbred lines is used to pollinate regenerated plants. The trait is genetically characterized by evaluating the segregation of the trait in first and later generation progeny. The heritability and expression in plants of traits selected in tissue culture are of particular importance if the traits are to be commercially useful.

Regenerated plants can be repeatedly crossed to inbred plants in order to introgress the ADP-glucose pyrophosphorylase inhibitory nucleic acids and/or WRINKLED1 nucleic acids into the genome of the inbred plants. In some embodiments, regenerated plants can also be crossed with inbred plants to introgress the inhibitory nucleic acid(s) into the genome of the plants. This process is referred to as backcross conversion. When a sufficient number of crosses to the recurrent inbred parent have been completed in order to produce a product of the backcross conversion process that is substantially isogenic with the recurrent inbred parent except for the presence of the introduced inhibitory nucleic acid(s), ADP-glucose pyrophosphorylase and/or WRINKLED1 nucleic acids, the plant is self-pollinated at least once in order to produce a homozygous backcross converted inbred containing the inhibitory nucleic acid(s) and/or ADP-glucose pyrophosphorylase and/or WRINKLED1 nucleic acids. Progeny of these plants are true breeding.

Alternatively, seed from transformed monocot plants regenerated from transformed tissue cultures is grown in the field and self-pollinated to generate true breeding plants.

Seed from the fertile transgenic plants can then be evaluated for the presence and/or expression of the ADP-glucose pyrophosphorylase inhibitory nucleic acids and/or WRINKLED1 nucleic acids (or the related protein products). Seed from the fertile transgenic plants can then be evaluated for the presence and/or expression of such nucleic acid(s) and/or proteins. Transgenic plant and/or seed tissue can be analyzed for the inhibitory nucleic acid(s) and/or WRINKLED1 expression using standard methods such as SDS polyacrylamide gel electrophoresis, liquid chromatography (e.g., HPLC) or other means of detecting a WRINKLED1 or ADP-glucose pyrophosphorylase.

Once a transgenic seed expressing the inhibitory nucleic acid(s) and/or WRINKLED1 nucleic acid(s), and having an increase in oil in the plant tissue is identified, the seed can be used to develop true breeding plants. The true breeding plants are used to develop a line of plants with an increase in the percent of oil and/or a decreased percentage of carbohydrate in the plant tissues while still maintaining other desirable functional agronomic traits. Adding the trait of increased oil/decreased carbohydrate production to the plant can be accomplished by back-crossing with this trait and with plants that do not exhibit these traits and studying the pattern of inheritance in segregating generations.

Those plants expressing the target trait in a dominant fashion are preferably selected. Back-crossing is carried out by crossing the original fertile transgenic plants with a plant from an inbred line exhibiting desirable functional agronomic characteristics while not necessarily expressing the trait of an increased percent of oil in the plant. The resulting progeny are then crossed back to the parent that expresses the increased oil/decreased carbohydrate trait. The progeny from this cross will also segregate so that some of the progeny carry the traits and some do not. This back-crossing is repeated until an inbred line with the desirable functional agronomic traits, and with expression of the trait involving an increase in oil and/or a decrease in carbohydrate in the vegetative tissues of the plant. Such expression of the increased percentage of oil or decreased percentage of carbohydrate in plant tissues can be expressed in a dominant fashion.

Subsequent to back-crossing, the new transgenic plants can be evaluated for an increase in the weight percent of oil (TAG) incorporated into vegetative tissues of the plant. This can be done, for example, by thin layer chromatography (TLC), gas chromatography, gas chromatography-flame ionization detector (GC-FID), electrospray ionization mass spectrometry (ESI-MS), mass spectroscopy, nuclear magnetic resonance (NMR), high pressure liquid chromatography (HPLC), and/or infrared spectral analysis of plant tissue or by other available methods of detecting and quantifying oils in harvested plant tissues. The new transgenic plants can also be evaluated for a battery of functional agronomic characteristics such as lodging, kernel hardness, yield, resistance to disease, resistance to insect pests, drought resistance, and/or herbicide resistance.

Plants that may be improved by these methods include but are not limited to oil and/or starch plants (canola, potatoes, cassava, lupins, sunflower and cottonseed), forage plants (alfalfa, clover and fescue), grains (maize, wheat, barley, oats, rice, sorghum, millet and rye), grasses (switchgrass, prairie grass, wheat grass, sudangrass, sorghum, straw-producing plants), softwood, hardwood and other woody plants (e.g., those used for paper production such as poplar species, pine species, and eucalyptus). Examples of plants and/or plant cells that can be modified as described herein include alfalfa (e.g., forage legume alfalfa), algae, avocado, barley, broccoli, Brussels sprouts, cabbage, canola, cassava, cauliflower, cole vegetables, collards, crucifers, grain legumes, grasses (e.g., forage grasses), jatropa, kale, kohlrabi, maize, miscanthus, mustards, nut sedge, oats, oil firewood trees, oilseeds, potato, radish, rice, rutabaga, sorghum, soybean, sugar beets, sugarcane, sunflower, switchgrass, tobacco, tomato, turnips, and wheat. In some embodiments, the plant is a *Brassicaceae* or other *Solanaceae* species. In some embodiments, the plant or cell can be a maize plant or cell. In some embodiments, the plant is not a species of *Arabidopsis*, for example, in some embodiments, the plant is not *Arabidopsis thaliana*.

Determination of Stably Transformed Plant Tissues:

To confirm the presence of the inhibitory nucleic acid(s) and/or the WRINKLED1 nucleic acids in the regenerating plants, or seeds or progeny derived from the regenerated plant, a variety of assays may be performed. Such assays include, for example, molecular biological assays available to those of skill in the art, such as Southern and Northern blotting and PCR; biochemical assays, such as detecting the presence of a protein product, e.g., by immunological means (ELISAs and Western blots) or by enzymatic function; plant part assays, such as leaf, seed or root assays; and also, by analyzing the phenotype of the whole regenerated plant. In some embodiments, the amount of oil in plant tissues is quantified. Such a quantified oil content can be compared to a control plant, for example, a control plant of the same species that has not be modified to express the inhibitory nucleic acid(s) and/or the WRINKLED1 nucleic acids.

Whereas DNA analysis techniques may be conducted using DNA isolated from any part of a plant, RNA may only be expressed in particular cells or tissue types and so RNA for analysis can be obtained from those tissues. PCR techniques may also be used for detection and quantification of RNA produced from the introduced ADP-glucose pyrophosphorylase inhibitory nucleic acid(s) and/or the introduced WRINKLED1 nucleic acids. RT-PCR also be used to reverse transcribe expressed RNA into DNA, using enzymes such as reverse transcriptase, and then this DNA can be amplified through the use of conventional PCR techniques. Further information about the nature of the RNA product may be obtained by Northern blotting. This technique will demonstrate the presence of an RNA species and give information about the integrity of that RNA. The presence or absence of an RNA species can also be determined using dot or slot blot Northern hybridizations. These techniques are modifications of Northern blotting and also demonstrate the presence or absence of an RNA species.

Southern blotting, northern blotting and PCR may be used to detect the inhibitory nucleic acid(s) ADP-glucose pyrophosphorylase and/or WRINKLED1 nucleic acid in question. Expression may also be evaluated by specifically identifying the presence or absence of protein products of the introduced WRINKLED1 nucleic acids and/or ADP-glucose pyrophosphorylase, respectively, by assessing the level of ADP-glucose pyrophosphorylase and/or WRINKLED1 mRNA and/or enzyme expressed, or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange, liquid chromatography or gel exclusion chromatography. The unique structures of individual proteins offer opportunities for use of specific antibodies to detect their presence in formats such as an ELISA assay. Combinations of approaches may be employed with even greater specificity such as Western blotting in which antibodies are used to locate individual gene products that have been separated by electrophoretic techniques. Additional techniques may be employed to confirm the identity of the inhibitory ADP-glucose pyrophosphorylase nucleic acids and/or the WRINKLED1 protein expressed such as evaluation by nucleic acid or amino acid sequencing following purification. The Examples of this application also provide assay procedures for detecting and quantifying an inhibitory ADP-glucose pyrophosphorylase nucleic acid and/or WRINKLED1 activity. Other procedures may be additionally used.

The expression of an inhibitory nucleic acid or gene product can also be determined by evaluating the phenotypic results of its expression. These assays also may take many forms including but not limited to analyzing changes in the chemical composition, morphology, or physiological properties of the plant. Chemical composition of plant tissues may be altered by expression of the ADP-glucose pyrophosphorylase inhibitory nucleic acids and/or WRINKLED1 transcription factor(s).

Rutabaga Transformation

Figure 2:
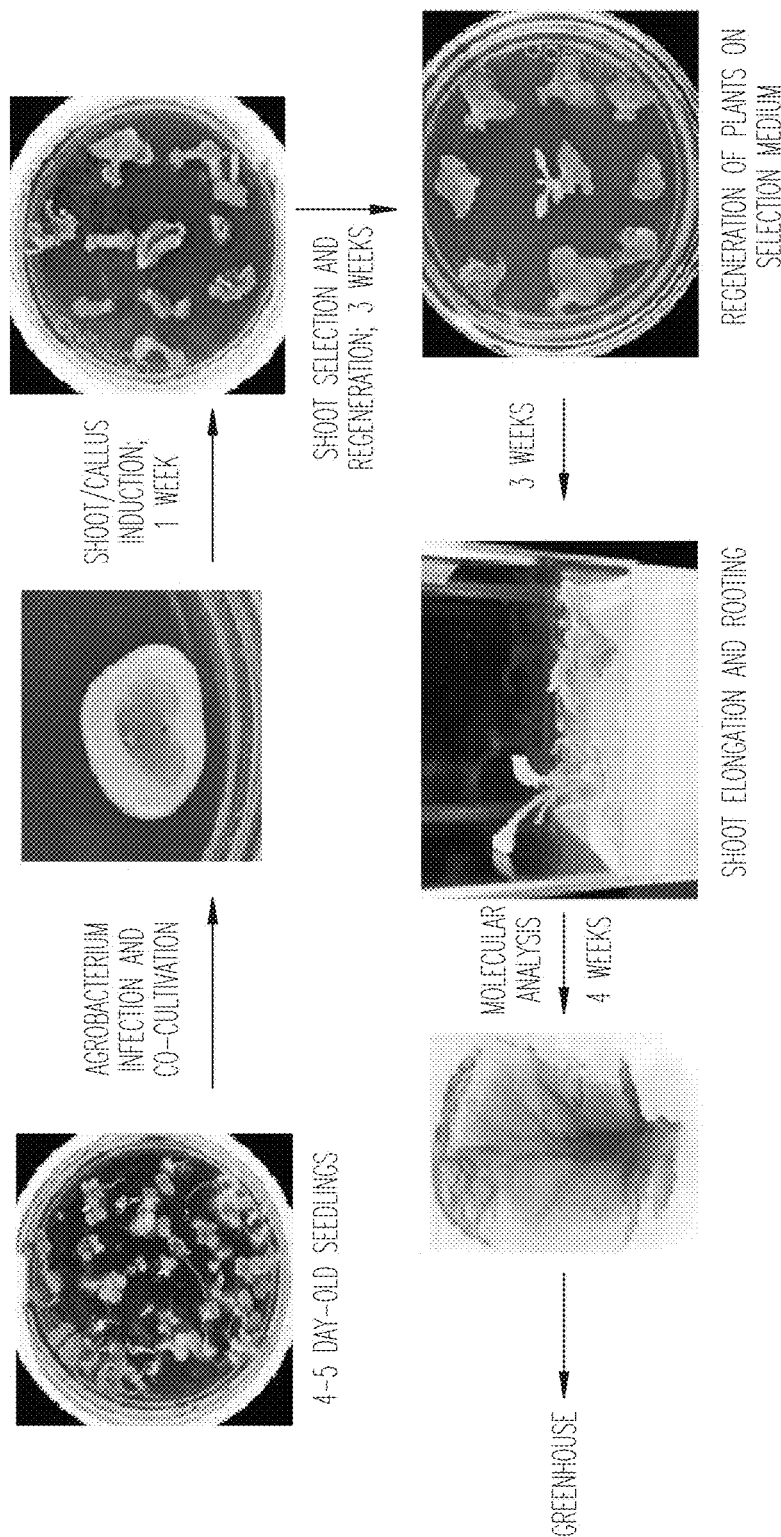
FIG. 2 illustrates the different stages involved in *Agrobacterium*-mediated transformation in rutabaga.
Figure 3A:
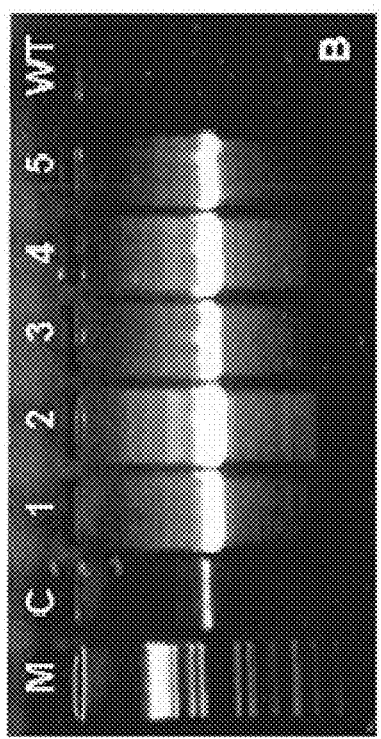
FIG. 3A-C show *Agrobacterium*-mediated transformation of rutabaga with pCAMBIA1305.2/35S::GUS-Plus.
Figure 3B:
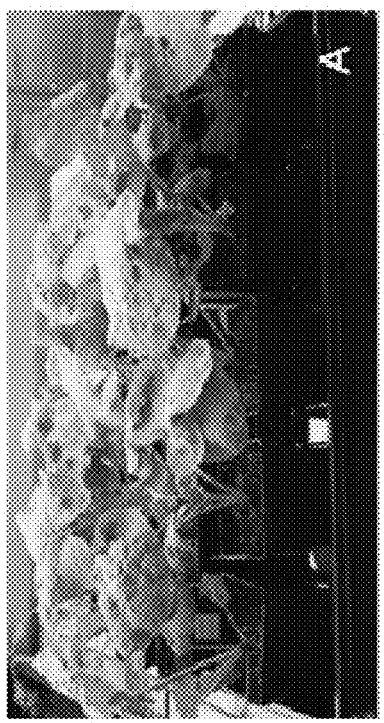
Figure 3C:
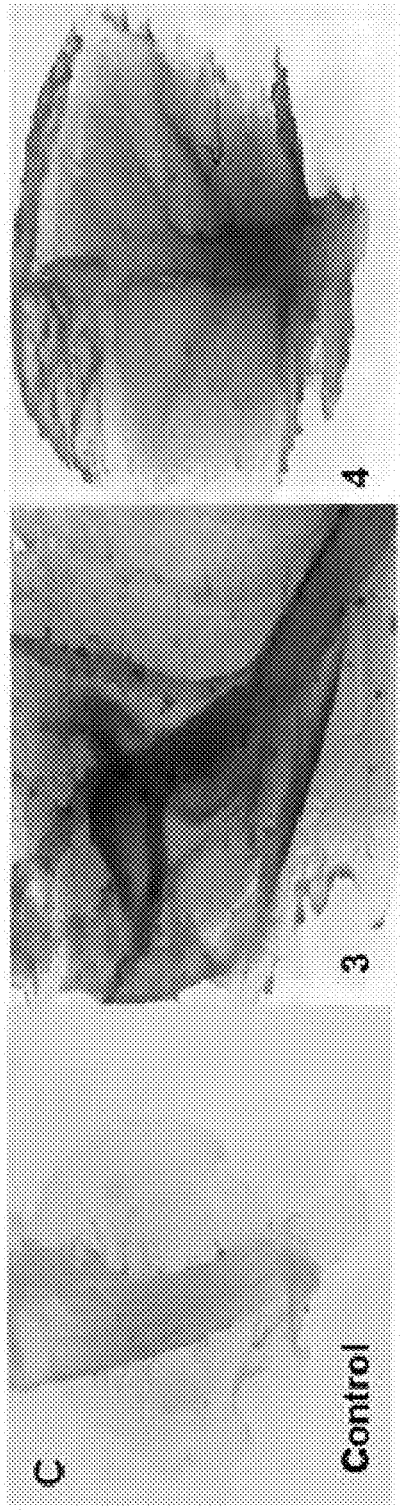

An efficient *Agrobacterium*-mediated transformation system was developed for the root vegetable crop plant rutabaga (*Brassica* var *napobrassica*) harboring binary vector carrying GUS gene. The type of explant, *Agrobacterium* strain, duration of infection and concentration of plant selection agent were optimized (see Example 3). Out of different explants tested, cotyledons derived from the 4-5-day-old seedlings responded best and formed shoots on medium containing optimized concentrations of plant growth regulators and selection agents within 3-4 weeks (FIG. 2-3). Transient reporter gene analysis indicated that all *Agrobacterium* strains GV3101, EHA105, LBA4404 and C58C tested are equally good in delivering foreign gene into rutabaga. However, LAB4404 had the highest transformation efficiency (Tables 3 and 4). Regenerated shoots were rooted on medium with optimized concentrations of auxin and selection agent within 3 weeks. The presence of foreign genes (GUS and HPTII/NPTII) was confirmed (FIG. 2-3). This system could be used in large scale production of transgenic rutabaga plants with different foreign genes.

Cultivation

Seeds, seedlings and plants containing WRINKLED1 and/or inhibitory ADP-glucose pyrophosphorylase nucleic acids can be grown in any medium which supports plant growth such as a commercial media, soil or water (hydroponically). The medium can be supplemented with a source of sugar (sugar source), such as carbohydrate or sugar. Such supplementation can increase the oil content of seedlings and plants containing WRINKLED1 and/or inhibitory ADP-glucose pyrophosphorylase nucleic acids.

As used herein, a source of sugar or a sugar source includes a material that contains or releases sugar. A material that releases sugar can be a material that is digested by agents in the environment, that erodes under cultivation conditions, that is formulated for sustained release, or that is a polymer of sugar units. "Sugar" refers to sugars, e.g., fructose, sucrose, and glucose, and to sugar alcohols, e.g., sorbitol.

The medium for growth of plants can contain about 0.1% to about 10% sugar or a source of sugar. The medium for growth of plants can also contain about 0.2% to about 7%, or about 0.5% to about 6%, or about 1% to about 5%, or about 1.5% to about 4%, or about 2% to about 4%, of sugar or a source of sugar.

Kits

One type of kit can include a seed containing WRINKLED1 and/or inhibitory ADP-glucose pyrophosphorylase nucleic acids, as well as instructions for cultivating the seeds, as well the use of any other material or reagent not included in the kit. The kit can also include a medium for growth of the seeds, or for grow of seedlings, or for induction of expression of the WRINKLED1 and/or inhibitory ADP-glucose pyrophosphorylase nucleic acids. Such a medium can also include sugar or a source of sugar. The kit can also include fertilizer. Instructions can include text on when and how to induce expression of the WRINKLED1 and/or inhibitory ADP-glucose pyrophosphorylase nucleic acids. Variations that can be implemented can also be described in the instructions.

Any of the nucleic acids, inhibitory nucleic acids, polypeptides and/or related nucleic acids and/or polypeptides described herein can also be included in a kit. In some embodiments, the kits can include a container that includes a nucleic acid, or a mixture of nucleic acids. Such a nucleic acid or mixture of nucleic acids can be used, for example, to transform plant cells and/or generate transgenic plants. In some embodiments, the nucleic acid(s) can encode a WRINKLED1 transcription factor. In another example, the kits can include a container that includes an inhibitory nucleic acid, or a mixture of inhibitory nucleic acids. Such inhibitory nucleic acids can be used, for example, to inhibit the expression of ADP-glucose pyrophosphorylase.

The kits can also include more than one container. For example, the kits can include two or more containers, where one container includes a WRINKLED1 nucleic acid, and another container includes an inhibitory nucleic acid that inhibits the expression of ADP-glucose pyrophosphorylases.

For example, the kit can include a container with a WRINKLED1 nucleic acid, where the WRINKLED1 nucleic acid can be part of an expression cassette or an expression vector.

In some embodiments, reagents for generating, assembling and/or introducing an ADP-glucose pyrophosphorylase inhibitory nucleic acid (e.g., siRNA, microRNA or RNAi) cocktail or candidate inhibitory molecules can be included in a kit. The kit may further include individual inhibitory nucleic acids that can be mixed to create an inhibitory nucleic acid cocktail or individual DNA constructs that can be mixed and transfected or transduced into cells wherein they express a cocktail of inhibitory nucleic acids. The kit may also include multiple expression cassettes or vectors encoding inhibitory nucleic acids to multiple sites in an ADP-glucose pyrophosphorylase, where expression of the expression cassettes or vectors generates a cocktail of inhibitory nucleic acids. The kit may also comprise reagents for creating or synthesizing the dsRNA and a polypeptide with RNAse III activity that can be used in combination to create of inhibitory nucleic acids cocktails.

The kit may also include one or more containers of buffers, such as buffers to dilute or stabilize the ADP-glucose pyrophosphorylase inhibitory nucleic acids or WRINKLED1 nucleic acids, or transcription buffers, or a hybridization buffers, enzymes or compounds for manipulating the nucleic acid, and components for isolating the resultant expression cassette that may be integrated into a plant genome or an inhibitory nucleic acid expressed by such an expression cassette.

The components of the kits may be packaged either in aqueous media or in lyophilized form. The containers can be vials, test tubes, flasks, bottles, syringes or other container means, into which a component may be placed, and suitably aliquoted.

Where there is more than one component in the kit, the kit also will generally contain a second, third or other additional container into which the additional components may be separately placed. However, various combinations of components may also be included in one container. The kits of the present invention also will typically include a means for containing the nucleic acids, and any other reagent containers in close confinement for commercial sale. Such containers may include injection or blow-molded plastic packages into which the desired vials are retained.

When the components of the kit are provided in one and/or more liquid solutions, the liquid solution is an aqueous solution, for example, a sterile aqueous solution. The nucleic acids can also be provided as an alcohol precipitate or as dried powder(s). When reagents and/or components are provided as a dry powder, the powder can be reconstituted by the addition of a suitable solvent. It is envisioned that the solvent may also be provided in another container.

In some embodiments, nucleic acids are provided in dried form or suspended in an appropriate buffer or solvent. It is contemplated that 0.1, 1, 5, 10, 20, 30, 40, 50, 60, 70, 80, 90, 100, 120, 120, 130, 140, 150, 160, 170, 180, 190, 200, 300, 400, 500, 600, 700, 800, 900, 1000 µg or nucleic acid can be provided in kits of the invention. The ADP-glucose pyrophosphorylase inhibitory nucleic acids are typically provided in a separate container from the WRINKLED1 encoding nucleic acids. However, in some embodiments, the ADP-glucose pyrophosphorylase inhibitory nucleic acids and the WRINKLED1 encoding nucleic acids are provided in the same container, for example, in a ratio optimized for transformation of plant cells.

The kits of the present invention will also typically include a means for containing the vials in close confinement for commercial sale, such as, e.g., injection and/or blow-molded plastic containers into which the desired vials are retained.

Such kits may also include components that preserve or maintain the nucleic acids or that protect against their degradation. Such components may be DNAse-free or RNAse free. The kits may include containers of DNase or RNase inhibitors. Such kits generally will comprise, in suitable means, distinct containers for each individual reagent or solution.

A kit will also include instructions for employing the kit components as well the use of any other reagent not included in the kit. Instructions may include variations that can be implemented.

DEFINITIONS

As used herein, "isolated" means a nucleic acid or polypeptide has been removed from its natural or native cell. Thus, the nucleic acid or polypeptide can be physically isolated from the cell, or the nucleic acid or polypeptide can be present or maintained in another cell where it is not naturally present or synthesized. The isolated nucleic acid or the isolated polypeptide can also be a nucleic acid or protein that is modified but has been introduced into a cell where it is or was naturally present. Thus, a modified isolated nucleic acid or an isolated polypeptide expressed from a modified isolated nucleic acid can be present in a cell along with a wild copy of the (unmodified) natural nucleic acid and along with wild type copies of the (natural) polypeptide.

As used herein, a "native" nucleic acid or polypeptide means a DNA, RNA or amino acid sequence or segment that has not been manipulated in vitro, i.e., has not been isolated, purified, and/or amplified.

The term "transgenic" when used in reference to a plant or leaf or vegetative tissue or seed for example a "transgenic plant," transgenic leaf," "transgenic vegetative tissue," "transgenic seed," or a "transgenic host cell" refers to a plant or leaf or tissue or seed that contains at least one heterologous or foreign gene in one or more of its cells. The term "transgenic plant material" refers broadly to a plant, a plant structure, a plant tissue, a plant seed or a plant cell that contains at least one heterologous gene in one or more of its cells.

The term "transgene" refers to a foreign gene that is placed into an organism or host cell by the process of transfection. The term "foreign nucleic acid" or refers to any nucleic acid (e.g., encoding a promoter or coding region) that is introduced into the genome of an organism or tissue of an organism or a host cell by experimental manipulations, such as those described herein, and may include nucleic acid sequences found in that organism so long as the introduced gene does not reside in the same location, as does the naturally occurring gene.

The term "host cell" refers to any cell capable of replicating and/or transcribing and/or translating a heterologous nucleic acid. Thus, a "host cell" refers to any eukaryotic or prokaryotic cell (e.g., plant cells, algal cells, bacterial cells, yeast cells, E. coli, insect cells, etc.), whether located in vitro or in vivo. For example, a host cell may be located in a transgenic plant, or located in a plant part or part of a plant tissue or in cell culture.

As used herein, the term "wild-type" when made in reference to a gene refers to a functional gene common throughout an outbred population. As used herein, the term "wild-type" when made in reference to a gene product refers to a functional gene product common throughout an outbred population. A functional wild-type gene is that which is most frequently observed in a population and is thus arbitrarily designated the "normal" or "wild-type" form of the gene.

As used herein, the term "plant" is used in its broadest sense. It includes, but is not limited to, any species of grass (e.g. turf grass), ornamental or decorative, crop or cereal, fodder or forage, fruit or vegetable, fruit plant or vegetable plant, herb plant, woody plant, flower plant or tree. It is not meant to limit a plant to any particular structure. It also refers to a unicellular plant (e.g. microalga) and a plurality of plant cells that are largely differentiated into a colony (e.g. volvox) or a structure that is present at any stage of a plant's development. Such structures include, but are not limited to, a seed, a tiller, a sprig, a stolen, a plug, a rhizome, a shoot, a stem, a leaf, a flower petal, a fruit, et cetera.

The term "plant tissue" includes differentiated and undifferentiated tissues of plants including those present in roots, shoots, leaves, pollen, seeds and tumors, as well as cells in culture (e.g., single cells, protoplasts, embryos, callus, etc.). Plant tissue may be in planta, in organ culture, tissue culture, or cell culture.

As used herein, the term "plant part" as used herein refers to a plant structure or a plant tissue, for example, pollen, an ovule, a tissue, a pod, a seed, a leaf and a cell. Plant parts may comprise one or more of a tiller, plug, rhizome, sprig, stolen, meristem, crown, and the like. In some instances the plant part can include vegetative tissues of the plant.

Vegetative tissues or vegetative plant parts do not include plant seeds, and instead include non-seed tissues or parts of a plant. The vegetative tissues can include reproductive tissues of a plant, but not the mature seeds.

The term "seed" refers to a ripened ovule, consisting of the embryo and a casing.

The term "propagation" refers to the process of producing new plants, either by vegetative means involving the rooting or grafting of pieces of a plant, or by sowing seeds. The terms "vegetative propagation" and "asexual reproduction" refer to the ability of plants to reproduce without sexual reproduction, by producing new plants from existing vegetative structures that are clones, i.e., plants that are identical in all attributes to the mother plant and to one another. For example, the division of a clump, rooting of proliferations, or cutting of mature crowns can produce a new plant.

The term "heterologous" when used in reference to a nucleic acid refers to a nucleic acid that has been manipulated in some way. For example, a heterologous nucleic acid includes a nucleic acid from one species introduced into another species. A heterologous nucleic acid also includes a nucleic acid native to an organism that has been altered in some way (e.g., mutated, added in multiple copies, linked to a non-native promoter or enhancer sequence, etc.). Heterologous nucleic acids can include cDNA forms of a nucleic acid; the cDNA may be expressed in either a sense (to produce mRNA) or anti-sense orientation (to produce an anti-sense RNA transcript that is complementary to the mRNA transcript). For example, heterologous nucleic acids can be distinguished from endogenous plant nucleic acids in that the heterologous nucleic acids are typically joined to nucleic acids comprising regulatory elements such as promoters that are not found naturally associated with the natural gene for the protein encoded by the heterologous gene. Heterologous nucleic acids can also be distinguished from endogenous plant nucleic acids in that the heterologous nucleic acids are in an unnatural chromosomal location, or are associated with portions of the chromosome not found in nature (e.g., the heterologous nucleic acids are expressed in tissues where the gene is not normally expressed).

The term "expression" when used in reference to a nucleic acid sequence, such as a gene, refers to the process of converting genetic information encoded in a gene into RNA (e.g., mRNA, rRNA, tRNA, or snRNA) through "transcription" of the gene (i.e., via the enzymatic action of an RNA polymerase), and into protein where applicable (as when a gene encodes a protein), through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

The terms "in operable combination," "in operable order," and "operably linked" refer to the linkage of nucleic acid sequences in such a manner that a nucleic acid molecule capable of directing the transcription of a coding region (e.g., gene) and/or the synthesis of a desired protein molecule is produced. The term also refers to the linkage of amino acid sequences in such a manner so that a functional protein is produced.

Transcriptional control signals in eukaryotes comprise "promoter" and "enhancer" elements. Promoters and enhancers consist of short arrays of DNA sequences that interact specifically with cellular proteins involved in transcription (see, for e.g., Maniatis, et al. (1987) Science 236:1237; herein incorporated by reference). Promoter and enhancer elements have been isolated from a variety of eukaryotic sources including genes in yeast, insect, mammalian and plant cells. Promoter and enhancer elements have also been isolated from viruses and analogous control elements, such as promoters, are also found in prokaryotes. The selection of a particular promoter and enhancer depends on the cell type used to express the protein of interest. Some eukaryotic promoters and enhancers have a broad host range while others are functional in a limited subset of cell types (for review, see Maniatis, et al. (1987), supra; herein incorporated by reference).

The terms "promoter element," "promoter," or "promoter sequence" refer to a DNA sequence that is located at the 5' end of the coding region of a DNA polymer. The location of most promoters known in nature is 5' to the transcribed region. The promoter functions as a switch, activating the expression of a gene. If the gene is activated, it is said to be transcribed, or is participating in transcription. Transcription involves the synthesis of mRNA from the gene. The promoter, therefore, serves as a transcriptional regulatory element and also provides a site for initiation of transcription of the gene into mRNA.

The term "regulatory region" refers to a gene's 5' transcribed but untranslated regions, located immediately downstream from the promoter and ending just prior to the translational start of the gene.

The term "promoter region" refers to the region immediately upstream of the coding region of a DNA polymer, and is typically between about 500 bp and 4 kb in length, and is preferably about 1 to 1.5 kb in length. Promoters may be tissue specific or cell specific.

The term "tissue specific" as it applies to a promoter refers to a promoter that is capable of directing selective expression of a nucleic acid of interest to a specific type of tissue (e.g., vegetative tissues) in the relative absence of expression of the same nucleic acid of interest in a different type of tissue (e.g., seeds). Tissue specificity of a promoter may be evaluated by, for example, operably linking a reporter gene and/or a reporter gene expressing a reporter molecule, to the promoter sequence to generate a reporter construct, introducing the reporter construct into the genome of a plant such that the reporter construct is integrated into every tissue of the resulting transgenic plant, and detecting the expression of the reporter gene (e.g., detecting mRNA, protein, or the activity of a protein encoded by the reporter gene) in different tissues of the transgenic plant. The detection of a greater level of expression of the reporter gene in one or more tissues relative to the level of expression of the reporter gene in other tissues shows that the promoter is specific for the tissues in which greater levels of expression are detected.

The term "cell type specific" as applied to a promoter refers to a promoter that is capable of directing selective expression of a nucleic acid of interest in a specific type of cell in the relative absence of expression of the same nucleic acid of interest in a different type of cell within the same tissue. The term "cell type specific" when applied to a promoter also means a promoter capable of promoting selective expression of a nucleotide sequence of interest in a region within a single tissue. Cell type specificity of a promoter may be assessed using methods well known in the art, e.g., immunohistochemical staining. Briefly, tissue sections are embedded in paraffin, and paraffin sections are reacted with a primary antibody that is specific for the polypeptide product encoded by the nucleic acid of interest whose expression is controlled by the promoter. A labeled (e.g., peroxidase conjugated) secondary antibody that is specific for the primary antibody is allowed to bind to the sectioned tissue and specific binding detected (e.g., with avidin/biotin) by microscopy.

Promoters may be "constitutive" or "inducible." The term "constitutive" when made in reference to a promoter means that the promoter is capable of directing transcription of an operably linked nucleic acid in the absence of a stimulus (e.g., heat shock, chemicals, light, etc.). Typically, constitutive promoters are capable of directing expression of a transgene in substantially any cell and any tissue. Exemplary constitutive plant promoters include, but are not limited to Cauliflower Mosaic Virus (CaMV SD; see e.g., U.S. Pat. No. 5,352,605, incorporated herein by reference), mannopine synthase, octopine synthase (ocs), superpromoter (see e.g., WO 95/14098; herein incorporated by reference), and ubi3 promoters (see e.g., Garbarino and Belknap, Plant Mol. Biol. 24:119-127 (1994); herein incorporated by reference). Such promoters have been used successfully to direct the expression of heterologous nucleic acid sequences in transformed plant tissue.

In contrast, an "inducible" promoter is one that is capable of directing a level of transcription of an operably linked nucleic acid in the presence of a stimulus (e.g., heat shock, chemicals, light, etc.) that is different from the level of transcription of the operably linked nucleic acid in the absence of the stimulus.

The term "vector" refers to nucleic acid molecules that transfer DNA segment(s). Transfer can be into a cell, cell to cell, et cetera. The term "vehicle" is sometimes used interchangeably with "vector." The vector can, for example, be a plasmid. But the vector need not be plasmid.

The following non-limiting Examples illustrate how aspects of the invention have been developed and can be made and used.

Example 1

Materials and Methods

This Example illustrates some methods that can be employed to make and use the invention.

Plasmid Construction

A WRINKLED1 (WRIJ) cDNA insert from *Arabidopsis thaliana* was obtained by PCR using primers 5'-CCAAggatccAAATCTAAACTTTCTCAGAGT-3' (SEQ ID NO:21) and 5'-CCTTacgcgtGGCAAAGACATTGATT-ATT-3' (SEQ ID NO:22). A fragment of 1463 bp containing the complete open reading frame was digested with BamHI and MluI. This fragment was then placed between a CaMV 35S (35S)/Patatin B33 (B33) promoter (Koster-Topfer et al., Mol. Gen. Genet. 219: 390-396 (1989), and a nos terminator to form an intermediate vector p35SWRI1-nos. Sequencing was performed to confirm the structure of the construct. A C-terminal His-Tag was introduced by site-directed mutagenesis with the following two inverse primers:

```
                                       (SEQ ID NO: 23)
WRI1HisR 5'-gtgatgatgGACCAAATAGTTACAAGAAAC-3'
and (SEQ ID NO: 24)
WRI1HisF 5'-catcaccatTGAGAGAGAGAGCTTT-3'.
```

This vector was then digested with SfiI and inserted into a pLH6000 vector (DNA cloning service, Hamburg, Germany) to form 35SWRI1 and B33-WRI1 (Sanjaya et al., Plant Biotechnol. J. pgs. 1-10 (2011), incorporated herein by reference in its entirety).

By way of example, the *B. napus* AGPase DNA sequence was used, which has been shown to inhibit AGPase activity in *B. napus* (Vigeolas et al., Plant Physiol. 136: 2676-2686 (2004)) when under the control of the 35S or B33 promoter. A *B. napus* AGPase (accession AJ271162) fragment from 565 to 1157 bp was synthesized; the 500-bp fragment was used for the construction of RNAi cassette in vector p35-iF2-1DCS (DNA Cloning Service). The 35S/B33 promoter was inserted (Koster-Topfer et al., 1989) to give rise to 35S/B331F2-AGPRNAi (35 SA GPRNAi). Fragment 35 S—WRI1His-nos was inserted into the NotI and NheI restriction sites of vector B331F2-AGPRNAi to form vector B331F2-AGPRNAi-WRI1His. This cassette was cut with SfiI and cloned into the SfiI restriction site of pLH6500 (DNA Cloning Service) to form the double-gene construct A GPRNAi-WRI1 (see, Sanjaya et al., *Plant Biotechnol. J. pgs.* 1-10 (2011), specifically incorporated herein by reference in its entirety).

TABLE 1

Primers for genes

| Gene | Accession No. | Forward or Reverse | Sequence | SEQ ID NO: |
|---|---|---|---|---|
| Actin2 | At3g18780 | F | TGTGACAATGGTACCGGTATGG | 25 |
|  |  | R | GCCCTGGGAGCATCATCTC | 26 |
| ACP1 | At3g05020 | F | TGTCTGGCAACAACAAGGATTAGT | 27 |
|  |  | R | GCGGAGGTTGAAGGATAGATTAGTC | 28 |
| 30AR | At1g24360 | F | AAAGCCGTCGCGAAGCTA | 29 |
|  |  | R | GGAGCCAATTGTCGGATTTG | 30 |
| APS1 | At5g48300 | F | ATGGCGTCTGTATCTGCAATTGGAG | 31 |
|  |  | R | GGATTTGAGTGAAATCTTGTCGTCG | 32 |
| BCCP2 | At5g15530 | F | AACAGGCGGGTCGGATCT | 33 |
|  |  | R | GCGGCTGCCATCTTTGAG | 34 |

TABLE 1-continued

Primers for genes

| Gene | Accession No. | Forward or Reverse | Sequence | SEQ ID NO: |
|---|---|---|---|---|
| PDHE1a | At1g01090 | F | GAGGCCAAGGTGGATCCAT | 35 |
|  |  | R | CAAAGCCACCAAGCATGTTG | 36 |
| P1-PKb1 | At5g52920 | F | CCAACGGTGGATCTGTGTCTAC | 37 |
|  |  | R | TCACTGCAAAACTCGCTGGTT | 38 |
| SUS2 | AT5G49190 | F | CAGTCTGCAGAGGAAGCCATAGT | 39 |
|  |  | R | AGGTCTGGGACGTATAGCCAAA | 40 |
| TAG1 | At2g19450 | F | TGGATTCTGCTGGCGTTACTAC | 41 |
|  |  | R | AGCCTATCAAGATCGACGAACTCT | 42 |
| WRI1 | At3g54320 | F | AAACGAGCCAAAAGGGCTAAG | 43 |
|  |  | R | GGGCTTGTCGGGTTATGAGA | 44 |

Plant Material and Transformation

*Arabidopsis* wild-type (Col2) seeds or transgenic seeds were surface sterilized and grown on half Murashige and Skoog (MS) agar plates containing 1% sucrose in a growth chamber set to 16 h light/8 h dark (70-80 μm/m$^2$/s) at 22° C. after 2 days of stratification at 4° C. Fifteen-day-old wild-type and transgenic plants were transferred onto soil and grown in a growth chamber at 16 h light/8 h dark (70-80 μm/m$^2$/s) and 22° C. The binary vectors were introduced into *Agrobacterium* strain GV3101 by electroporation, and the T-DNAs were mobilized into *Arabidopsis* by flower-dip transformation (Clough and Bent, Plant J. 16: 735-743 (1998)). Transgenic plants (Ti) were selected on ½ MS agar plates containing 1% sucrose and 20 mg/L hygromycin or 100 mg/L kanamycin. In general, wild-type and homozygous transgenic seedlings were grown on the same shelf of the growth chamber when used for metabolite analysis and other assays. To boost the production of oil, wild-type and double (AGPRNAi-WRI1) transgenic seeds were grown on ½ MS medium supplemented with 0% and 3% sucrose.

Quantitative Real-Time PCR (qRT-PCR)

Total RNA was extracted from 15-day-old plants using an RNeasy Plant Mini Kit (Qiagen, Valencia, Calif.), and samples were stored at −80° C. Approximately 0.5 μg of total RNA was reverse transcribed by SuperScript III (Invitrogen, Carlsbad, Calif.), according to the manufacturers protocol. The cDNA pool (1.0 L) was used as a template in a 23-μL PCR consisting of forward and reverse gene-specific primers (Table 1) and Fast SYBR Green master mix (Applied Biosystems, Forest City, Calif.) on an Applied Biosystems PRISM 7000 Sequence Detection System. The copy numbers of the cDNAs were quantified using a standard curve method, and the copy numbers of each sample was standardized to ACTIN2. The relative expression (as fold change) was scaled such that the expression level of the wild type was equal to one in all the graphs.

Metabolite Analysis

Fifteen-day-old wild-type and transgenic *Arabidopsis* whole seedlings were freeze-dried. Neutral lipids were extracted from dried samples using chloroform-methanol with 100 μM internal standard tri15:0 triacylglycerides (TAG) and separated on silica plate using a mixture of solvents consisting of petroleum ether: ethyl ether:acetic acid (80:20:1, by volume). After thin-layer chromatography (TLC), TAG bands were visualized with iodine vapor. For quantitative analysis, TAG bands were isolated from the TLC plate, dissolved in toluene with 1 μM internal standard tri 13:0 TAG and assayed using ESI-MS as described previously by Durrett et al. (Proc. Natl. Acad. Sci. USA, 107: 9464-9469 (2010)).

Starch and sugars were analyzed by using an NAD(P)H-linked assay (Lowry and Passonneau, A FLEXIBLE SYSTEM OF ENZYMATIC ANALYSIS. Orlando, Fla.: Academic Press, 1-291 (1972)). About 5- to 10-mg dried whole seedling samples were ground into fine powder in a Retsch Mill at a frequency of 30 (maximum speed) for 30 s, soluble sugars were extracted by the addition of 1 mL 3.5% perchloric acid. Tubes were incubated on ice for 5 min before being centrifuged at 20,000 g for 10 min at 4° C. Approximately 750 μL of supernatant was recovered and processed as described below for glucose, fructose and sucrose assays. The pellet was washed twice with 70% alcohol, resuspended in 500 μL 0.2 M KOH and incubated at 95° C. for 30 min. Samples were allowed to cool for 2-5 min before adding 90 μL of 1 M acetic acid to bring the pH to about 5. Starch in the pellet was broken down to glucose by the addition of an enzyme cocktail (50 μL) consisting of 6.6 U amyloglucosidase (E-AMGDF; Megazyme, Wicklow, Ireland) and 50 U of α-amylase (E-ANAAM; Megazyme) and incubated for 2 days on a shaker at room temperature. Samples were then centrifuged for 30 min at 20,000 g, and the supernatant was transferred to fresh microfuge tubes. Five to ten microliters of the starch sample was assayed for glucose as described below.

The 750-μL supernatant recovered as described above was neutralized to pH 7 by the addition of 150-μL of buffer consisting of 2 M KOH, 150 mM HEPES and 10 mM KCl. Samples were frozen in liquid nitrogen to help precipitate salts. Samples were then thawed and centrifuged at 20,000 g, and the supernatant was transferred to a fresh microfuge tube. Both starch and soluble sugars were assayed on a plate reader (Spectra Max M2, Molecular devices, Sunnyvale, Calif.) using an NADP(H)-linked assay at 340 nm. All samples were read in triplicate, using standard 96-well clear bottom plates. Each well that was used was filled with 200 μL of 110 mM HEPES buffer pH 7.2 consisting of 15 mM MgCl$_2$, 3 mM EDTA, 500 nmol NADP, 500 nmol ATP and 0.4 U glucose-6-phosphate dehydrogenase (G-8529; Sigma, St Louis, Mo.). Five microliters of sample was added to each well, and the reaction was started by adding 0.5 U of Hexokinase (H-4502; Sigma). Fructose and sucrose were determined by the sequential addition of 4 U Phosphoglucose isomerase (P-9544; Sigma) and 25 U Invertase (1-4504; Sigma). The change in optical densities (Δ ODs) were determined by taking endpoint assays before and after the addition of each enzyme. Because the Spectra Max M2 plate reader can also determine the path length of aqueous samples, absorbance units were normalized to a 1-cm path length and absolute glucose amounts were determined using an extinction coefficient of 6220 L/mol/cm for Nicotineamide 2-phosphoadenine dinucleotide (NADPH) at 340 nm (Lowry and Passonneau, 1972).

Microscopy

For oil droplet visualization, the first pair of leaves and main root samples from 15-day-old wild-type and transgenic seedlings were used. Freshly harvested leaf and root samples mounted in Nile red (2.5 μg/mL methanol) in 75% glycerol on a slide were examined using an Olympus FluoView 1000 Laser Scanning Confocal Microscope. Oil droplets were observed at 570-630 nm emission following 559-nm excitation by a solid state laser. Chloroplasts were observed at 655-755-nm emission using the same laser excitation. Images were captured with the Olympus FluoView 1000 ASW software (Olympus, Center Valley, Pa.).

Results from modification of *Arabidopsis thaliana* are provided in Sanjaya et al., *Plant Biotechnology J. pgs.* 1-10 (2011).

Example 2

Modification of *Brassicaceae* to Produce More Oil

This Example discusses methods for genetically modifying *Brassicaceae* (e.g., *Brassica* var *napobrassica*) plants to produce more oil in their vegetative tissues.

Methods:

Constructs for reduction of ADP-glucose pyrophosphorylase in *Brassica napus* were designed to express RNAi (referred to as AGPRNAi constructs). These AGPRNAi constructs were designed to reduce *B. napus* synthesis of carbohydrate by targeting a region of the ADP-glucose pyrophosphorylase small subunit sequence conserved across *Arabidopsis* and *Brassica*. A sequence from *B. napus* AGPase (accession AJ271162) with 82% DNA sequence identity to the most similar *Arabidopsis* gene APS1 (At5g48300) was used to design the RNAi construct.

APS1 encodes one of the major catalytic isoforms of the small subunit of AGPase. The following *Brassica napus* mRNA for ADP-glucose pyrophosphorylase small subunit (AGPase), with accession number AJ271162 and SEQ ID NO:4, was used as a template for expression of an ADP-glucose pyrophosphorylase RNAi:

```
  1 GGACTACGAG AAGTTCATTC AAGCGCATCG TGAGACCGAC
 41 GCTGATATCA CTGTTGCTGC TCTTCCTATG GATGAGAAAC
 81 GTGCCACGGC TTTTGGACTT ATGAAGATTG ATGACGAAGG
121 AAGGATCATT GAGTTTGCTG AGAAGCCTAA AGGAGAGCAG
161 TTAAAGGCTA TGAAGGTTGA TACAACAATC TTGGGACTTG
201 ATGACGAAAG GGCCAAAGAG ATGCCCTTTA TTGCTAGTAT
241 GGGGATATAT GTTGTTAGCA AGAATGTGAT GTTGGACTTG
281 CTCCGAGACC AGTTCCCTGG AGCTAATGAC TTCGGGAGTG
321 AAGTTATCCC TGGTGCTACT GATCTTGGAC TCAGAGTGCA
361 AGCTTATCTG TATGATGGAT ACTGGGAAGA TATTGGTACC
401 ATTGAAGCCT TTTACAATGC TAATCTTGGG ATCACCAAGA
441 AACCAGTACC AGATTTCAGC TTCTATGACC GTTCAGCACC
481 AATCTACACA CAGCCTCGGT
```

To form an expression vector to express the ADP-glucose pyrophosphorylase RNAi, one copy of a nucleic acid encoding the 5' to 3' orientation of SEQ ID NO:4 shown above was ligated to an 'intron' (linker) sequence that was then ligated to a nucleic acid encoding the 3' to 5' orientation of SEQ ID NO:4 (see FIG. 1).

A nucleic acid encoding the WRINKLED1 transcription factor can be inserted into an expression vector in preparation for expression in plants. For example, the WRINKLED1 sequence with accession number AY254038.2 (GI:51859605) can be employed; this sequence is reproduced below as SEQ ID NO:14

```
   1 AAACCACTCT GCTTCCTCTT CCTCTGAGAA ATCAAATCAC
  41 TCACACTCCA AAAAAAATC TAAACTTTCT CAGAGTTTAA
  81 TGAAGAAGCG CTTAACCACT TCCACTTGTT CTTCTTCTCC
 121 ATCTTCCTCT GTTTCTTCTT CTACTACTAC TTCCTCTCCT
 161 ATTCAGTCGG AGGCTCCAAG GCCTAAACGA GCCAAAAGGG
 201 CTAAGAAATC TTCTCCTTCT GGTGATAAAT CTCATAACCC
 241 GACAAGCCCT GCTTCTACCC GACGCAGCTC TATCTACAGA
 281 GGAGTCACTA GACATAGATG GACTGGGAGA TTCGAGGCTC
 301 ATCTTTGGGA CAAAAGCTCT TGGAATTCGA TTCAGAACAA
 361 GAAAGGCAAA CAAGTTTATC TGGGAGCATA TGACAGTGAA
 401 GAAGCAGCAG CACATACGTA CGATCTGGCT GCTCTCAAGT
 421 ACTGGGGACC CGACACCATC TTGAATTTTC CGGCAGAGAC
 481 GTACACAAAG GAATTGGAAG AAATGCAGAG AGTGACAAAG
 521 GAAGAATATT TGGCTTCTCT CCGCCGCCAG AGCAGTGGTT
 581 TCTCCAGAGG CGTCTCTAAA TATCGCGGCG TCGCTAGGCA
 601 TCACCACAAC GGAAGATGGG AGGCTCGGAT CGGAAGAGTG
 641 TTTGGGAACA AGTACTTGTA CCTCGGCACC TATAATACGC
 681 AGGAGGAAGC TGCTGCAGCA TATGACATGG CTGCGATTGA
 721 GTATCGAGGC GCAAACGCGG TTACTAATTT CGACATTAGT
 761 AATTACATTG ACCGGTTAAA GAAGAAAGGT GTTTTCCCGT
 801 TCCCTGTGAA CCAAGCTAAC CATCAAGAGG GTATTCTTGT
 841 TGAAGCCAAA CAAGAAGTTG AAACGAGAGA AGCGAAGGAA
 881 GAGCCTAGAG AAGAAGTGAA ACAACAGTAC GTGGAAGAAC
 921 CACCGCAAGA AGAAGAAGAG AAGGAAGAAG AGAAAGCAGA
 961 GCAACAAGAA GCAGAGATTG TAGGATATTC AGAAGAAGCA
1001 GCAGTGGTCA ATTGCTGCAT AGACTCTTCA ACCATAATGG
1041 AAATGGATCG TTGTGGGGAC AACAATGAGC TGGCTTGGAA
1081 CTTCTGTATG ATGGATACAG GGTTTTCTCC GTTTTTGACT
1121 GATCAGAATC TCGCGAATGA GAATCCCATA GAGTATCCGG
1141 AGCTATTCAA TGAGTTAGCA TTTGAGGACA CATCGACTTG
1201 CATGTTCGAT GATGGGAAGC ACGAGTGCTT GAACTTGGAA
1241 AATCTGGATT GTTGCGTGGT GGGAAGAGAG AGCCCACCCT
1281 CTTCTTCTTC ACCATTGTCT TGCTTATCTA CTGACTCTGC
1321 TTCATCAACA ACAACAACAA CAACCTCGGT TTCTTGTAAC
1361 TATTTGGTCT GAGAGAGAGA GCTTTGCCTT CTAGTTTGAA
1401 TTTCTATTTC TTCCGCTTCT TCTTCTTTTT TTTCTTTTGT
1441 TGGGTTCTGC TCAGGGCTTG TATTTCAGTT TCAGGGCTTG
```

-continued

1481 TTCGTTGGTT CTGAATAATC AATGTCTTTG CCCCTTTTCT

1501 AATGGGTACC TGAAGGGCGA

Primers are selected from the SEQ ID NO: 14 nucleic acid sequence for isolation of WRINKLED1 nucleic acids from other species. Such primers can be used to identify and/or isolate WRINKLED1 nucleic acids from other species, for example, by hybridization, polymerase chain reaction, reverse transcription, and combinations of these and other methods. For example, a forward primer spanning nucleotides 56 to 75 of the SEQ ID NO: 14 nucleic acid can have the following sequence, or be complementary to the following sequence (SEQ ID NO:15):

AAATCTAAAC TTTCTCAGAG.

A reverse primer spanning nucleotides 1471 to 1512 of the SEQ ID NO:14 sequence can have the following sequence, or be complementary to the following sequence (SEQ ID NO:16):

TCAGGGCTTG TTCGTTGGTT CTGAATAATC AATGTCTTTG CC.

Example 3

Improved *Agrobacterium*-Mediated Transformation of *Brassica*

With few exceptions, *Agrobacterium tumefaciens* transformation experiments with *B. napus* have been performed principally with the spring variety *B. napus* L. ssp. *oleifera* cv. Westar, Oscar, Taparoo, Charlton, Rainbow, *B. oleracea* var *botrytis*, B-4, *B. oleracea* var *botrytis*, WG-11-1, Italia and capitata. These older procedures are somewhat inefficient and not particularly successful for the winter variety *B. napobrassica* American purple Top. For example, there are only isolated reports on transgenic rutabaga, and no transformation report for American purple Top variety (Christey & Braun, Transgenic vegetable and forage *Brassica* species: rape, kale, turnip and rutabaga (swede), In BIOTECHNOLOGY IN AGRICULTURE AND FORESTRY, Vol. 47, Transgenic crops II (ed. By Y. P. S. Bajaj), Springer-Verlag Berlin Heidelberg, pp. 87-101 (2001); Li et al., *Plant Cell Rep* 15: 97-101 (1995)). The following procedures are improvement over the older techniques of *Agrobacterium*-mediated transformation in *B. napobrassica* and other *Brassica* species.

Materials and Methods

Media
KCMS medium: MS salts (Sigma)—4.4 g/l; $KH_2PO_4$—200 mg/l.
AB medium:
 20×AB Salts (g/l)
 $NH_4Cl$—20
 $MgSO_4 \cdot 7H_2O$—6
 KCl—3
 $CaCl_2$—0.2
 $FeSO_4$—50 mg/l
 20×AB Buffer (g/l)
 $K_2HPO_4$—60
 $NaH_2PO_4 \cdot H_2O$—23

All the stock solutions were autoclaved and 50 ml of the AB salts and the AB buffer was added to 900 ml autoclaved water. Five percent glucose was included while growing *Agrobacterium*.

Surface Sterilization of Seeds

Seeds (winter variety *B. napobrassica* American purple Top) were placed in sterile 50 ml plastic tubes and approximately 35-40 ml of 20% sodium hypochlorite was added. The tube was sealed tightly and placed it on a shaker, then shaken vigorously at room temperature (RT, 22-25° C.) for 20 min. The sodium hypochlorite was discarded and the seeds were rinsed five times with shaking for approximately 30 seconds in 40-45 ml sterile distilled water. The seeds were decanted into a sterile Petri plate.

Seed Germination

The surface-sterilized seeds were transferred into Petri plates containing seed germination medium, with about 10-12 seeds per plate. The seeds were germinated the in the dark/partial light at RT (22-25 1° C.) for 4-5 days.

*Agrobacterium* Preparation

On the same day as seed germination, *Agrobacterium* strains LBA4404; GV3101; C58; and EHA105 harboring the binary vector was streaked onto LB plates containing 100 μg/ml rifampicin and 50 μg/ml kanamycin. The plates were incubated for 2 days at 28° C. After such incubation, a single colony of *Agrobacterium* from each of the plates was inoculated into 10 ml LB/AB liquid medium containing 100 μg/ml rifampicin and 50 μg/ml kanamycin. Each inoculum was cultured at 28° C. with shaking (250 rpm) for 36 hours while the optical density at 650 nm was monitored using a spectrophotometer. The *Agrobacterium* cultures were centrifuged (7,000 rpm) for 10 min at 4° C., the supernatants were decanted and the pellets were rinsed in liquid ½ MS medium (without antibiotics). Alternatively, the *Agrobacterium* cultures can be grown in AB (OD 0.3-0.5) directly for infection with or without acetosyringone, and the pellets can be resuspended as above. In either case the OD (650 nm) of the cultures was adjusted to 0.3-0.5 with MS minimal organic medium.

*Agrobacterium* Infection and Cocultivation

The seedlings were removed from the germination medium and placed in an empty Petri plate. The cotyledons were cut from the seedling, including approximately 2 mm stalk (petiole) and hypocotyls (0.5-1.0 cm), using a scalpel blade (FIG. 2). The cotyledons (proximal end) and hypocotyl explants were precultured on KCMS medium for 2-days under partial light or dark conditions at room temperature. The cut ends of the cotyledon (proximal end) and hypocotyl explants were then dipped in *Agrobacterium* (harboring binary vector) suspension (OD 0.3-0.5) for 30 seconds to 1 minute. The infected explants were placed into cocultivation medium (KCMS supplemented with acetosyringone), the Petri plates were sealed using 3M surgical tape and incubated in the dark at 25° C. for 2-days.

Shoot/Callus Induction

The *Agrobacterium* infected explants were washed 3 times in liquid ½ MS medium supplemented with 200 mg/liter Timentin at 30 minute intervals; the cells were collected after each wash by 50 rpm centrifugation. The shoot/callus or explants were transferred into induction medium containing 200 mg/l Timentin (Table 2). The Petri dishes were sealed with 3M surgical tape and incubated under dim light at 22-23° C. for 1 week.

TABLE 2

Preferred conditions for rutabaga cultivar American Top transformation

| | Pre-culture | Cocultivation | Shoot/callus regeneration | Selection | Shoot elongation | Root Formation |
|---|---|---|---|---|---|---|
| Growth medium | KCMS | KCMS | MS | MS | MS | ½ MS |
| Plant growth regulators (mg/l) | Kn 0.1, 2,4-D 0.2 | Kn 0.1, 2,4-D 0.2 | BAP 2.0 + TDZ 1.0 + NAA 0.1 + GA₃ 0.05 | BAP 2.0 + TDZ 1.0 + NAA 0.1 + GA₃ 0.05 | BAP 0.5 | IBA 1.0 |
| Sucrose (%) | 3 | 3 | 1 | 1 | 1 | 1 |
| Vitamins (with MS medium, Sigma) | Thiamin HCl (100 mg/l) | Thiamin HCl (100 mg/l) | B5 | B5 | B5 | B5 |
| Silver nitrate (mg/l) | — | — | 5 | 5 | 5 | — |
| Acetosyringone (μM) | — | 100 | — | — | — | — |
| Selection (mg/l) | — | — | — | Kan 75 or Hyg 10 | Kan 75 or Hyg 10 | Kan 75 or Hyg 10 |
| Timentin (mg/l) | — | — | 200 | 200 | 200 | 200 |

Abbreviations:
NAA: α-Naphthaleneacetic acid
MS: Murashige and Skoog's medium
2,4-D: Dichlorophenoxy acetic acid
BAP: 6-Benzylaminopurine
GA3: Gibberellic acid
IBA: Indole 3-butyric acid
TDZ: Thidiazuron; 1-phenyl-3-(1,2,3,-thidiazol-5-yl) urea
Kn: Kinetin
Kan: Kanamycin
Hyg: Hygromycin
GUS: β-Glucuronidase
B5: Gamborg vitamin Shoot Selection The explants were transferred to shoot selection medium containing 200 mg/liter Timentin and 100 mg/liter kanamycin or 10 mg/liter hygromycin, and then incubated in light (16 h light and 8 h dark) at 22° C. for 3 weeks.

Shoot Elongation

The explants with shoot initials were transferred to shoot elongation medium containing 200 mg/liter Timentin and 100 mg/liter kanamycin or 10 mg/liter hygromycin then incubated under light (16 h) at 22° C. for 2-3 weeks.

Root Initiation and Plant Establishment

The green shoots were transferred to magenta jars containing root initiation medium with 200 mg/liter Timentin so that the base/ends of the shoots were well placed in the medium. The shoots were incubated in light at 22° C. for 2 weeks. The plants were removed from the magenta jars and washed briefly with reverse osmosis water to remove traces of Agargel, then transplanted into the potting mix at depths consistent with the root length. The shoots were watered lightly after soil compaction, and the shoots were maintained in a growth chamber for 2-3 week before transfer to normal glasshouse conditions. Leaf samples were collected for molecular or GUS assays (Tables 3 and 4).

Results

Transformation efficiencies of different *Agrobacterium* strains were measured as a proportion of blue inclusions in shoots or callus after transformation. The results show that strain LBA4404 has highest transformation efficiency of the strains tested.

TABLE 3

Transformation efficiencies of different *Agrobacterium tumefaciens* strains

| *Agrobacterium* strain | GUS positive shoot | % GUS Positive |
|---|---|---|
| GV3101 | 25/65 | 39 |
| EHA105 | 23/58 | 40 |
| LBA4404 | 48/70 | 69 |
| C58C1 | 31/62 | 50 |

Moreover, hygromycin selection of putative transgenic plants was very stringent. The escape rate was about 14% for hygromycin and 48% for kanamycin. Use of higher antibiotic concentrations has a negative impact on shoot regeneration and subsequent rooting.

TABLE 4

Transgenic shoot regeneration frequency in rutabaga

| Selection | Green shoots per explant (cotyledon) | % | Number of GUS positive plants | % | Escapes | % |
|---|---|---|---|---|---|---|
| Hygromycin | 30/205 | 15 | 26/205 | 13 | 4/30 | 14 |
| Kanamycin | 40/210 | 20 | 21/210 | 10 | 19/40 | 48 |

Example 4

Transgenic Rutabaga (*Brassica* var *napobrassica*) Produces More Oil

This Example describes genetically modified *Brassica napobrassica* (rutabaga) plants that have 5% oil/triacylglycerols (TAGs) per dry weight compared to wild type plants that have only 0.06% oil per dry weight in their vegetative tissues.

Methods:

The constructs described in Example 2 for reduction of ADP-glucose pyrophosphorylase by expression of RNAi and for increased expression of WRINKLED1 were transformed into rutabaga plant cells, rutabaga tissues and rutabaga plants were generated as described in Example 3.

Results

Figure 4A:
FIG. 4A-D illustrates that rutabaga plants expressing the WRINKLED1 transcription factor and the ADP-glucose pyrophosphorylase RNAi have increased oil content relative to wild type rutabaga (double construct).
Figure 4B:
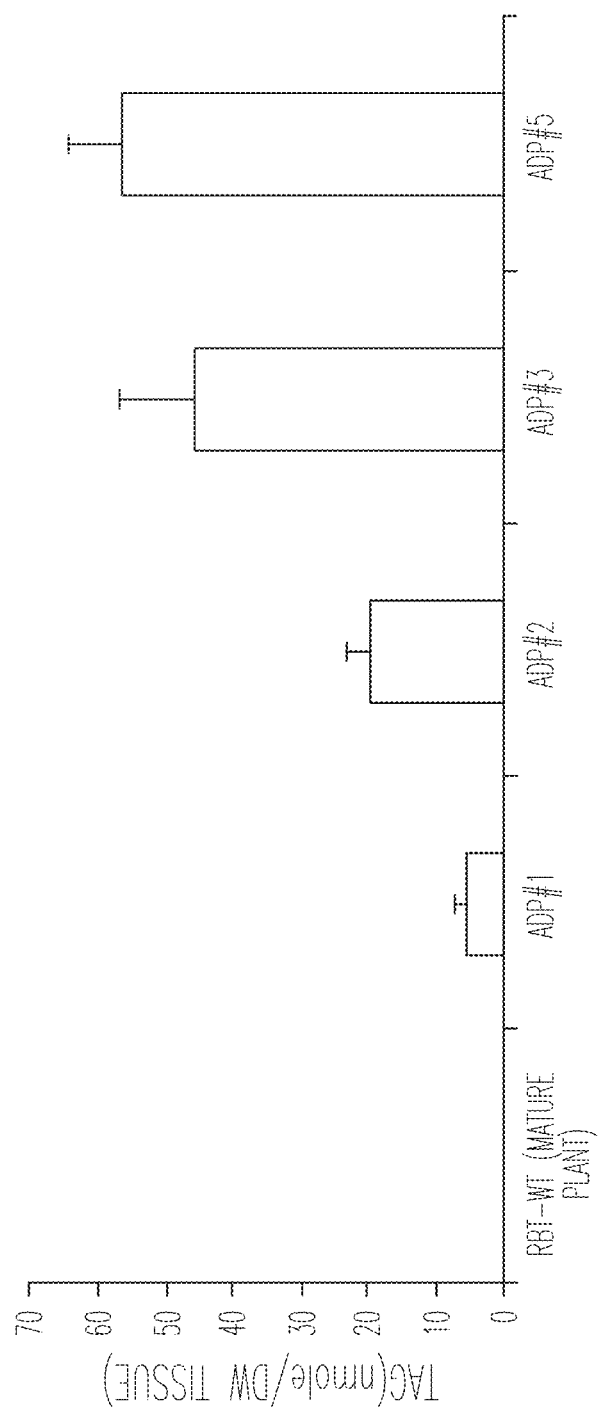
Figure 4C:
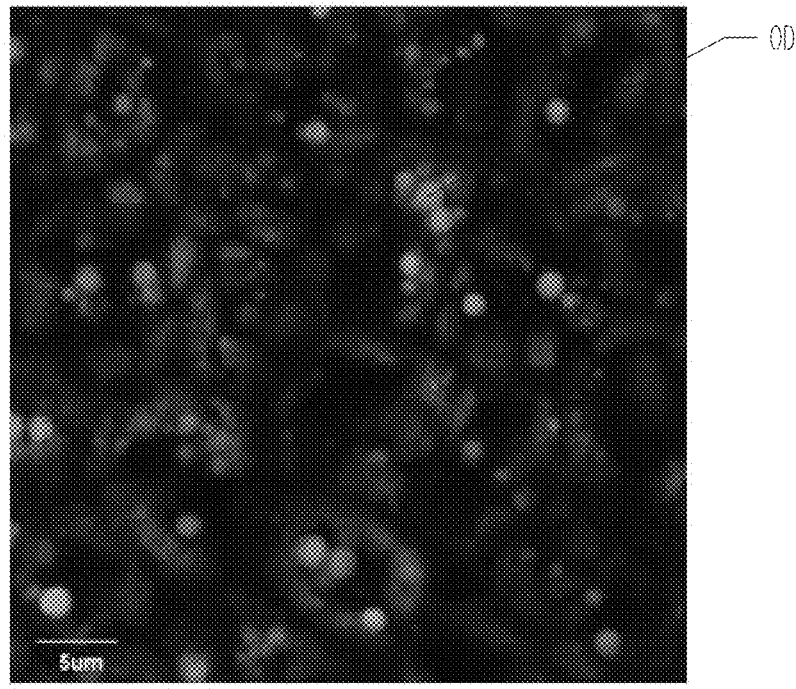
Figure 4D:
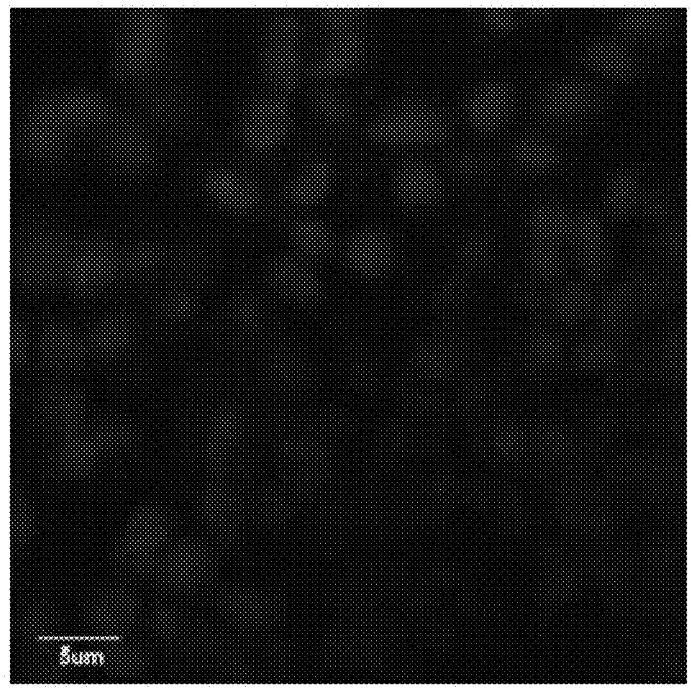

FIG. 4A shows images of 3-month old rutabaga expressing the WRINKLED1 transcription factor and RNAi directed against ADP-glucose pyrophosphorylase transcripts. FIG. 4C shows oil droplets in WRINKLED1/AGPase RNAi transformant #5, while FIG. 4D shows that wild type rutabaga has essentially no oil droplets in vegetative tissues. As illustrated in FIG. 4B, the WRINKLED1/AGPase RNAi transformed plants had about 5-58 nmole triacylglycerols per gram dry weight of vegetative tissue, compared to wild type rutabaga with only about 1 nmole triacylglycerols per gram dry weight of vegetative tissue. Although there was some variation in the amount of oil produced by different rutabaga transformants at 3 months of age, each of the examined WRINKLED1/AGPase RNAi transformed plants expressed significantly more oil than wild type rutabaga. For example, rutabaga transformant line #1 had at least 5 times more oil than wild type rutabaga, while rutabaga transformant line #5 had at least 50 times more oil than wild type rutabaga.

Example 5

Transgenic Oil-Rich Plants are Energy-Rich Fodder

The results described in Example 1 and 2 demonstrate that concerting carbon sources that would be destined to sugar into oil within vegetative tissues is effective in *Arabidopsis* and rutabaga. As a preliminary test of the effectiveness of oil-rich rutabaga as fodder, moth (*Spodoptera*) larvae were grown on several the transgenic *Arabidopsis* plants described in Example 1.

Figure 5A:
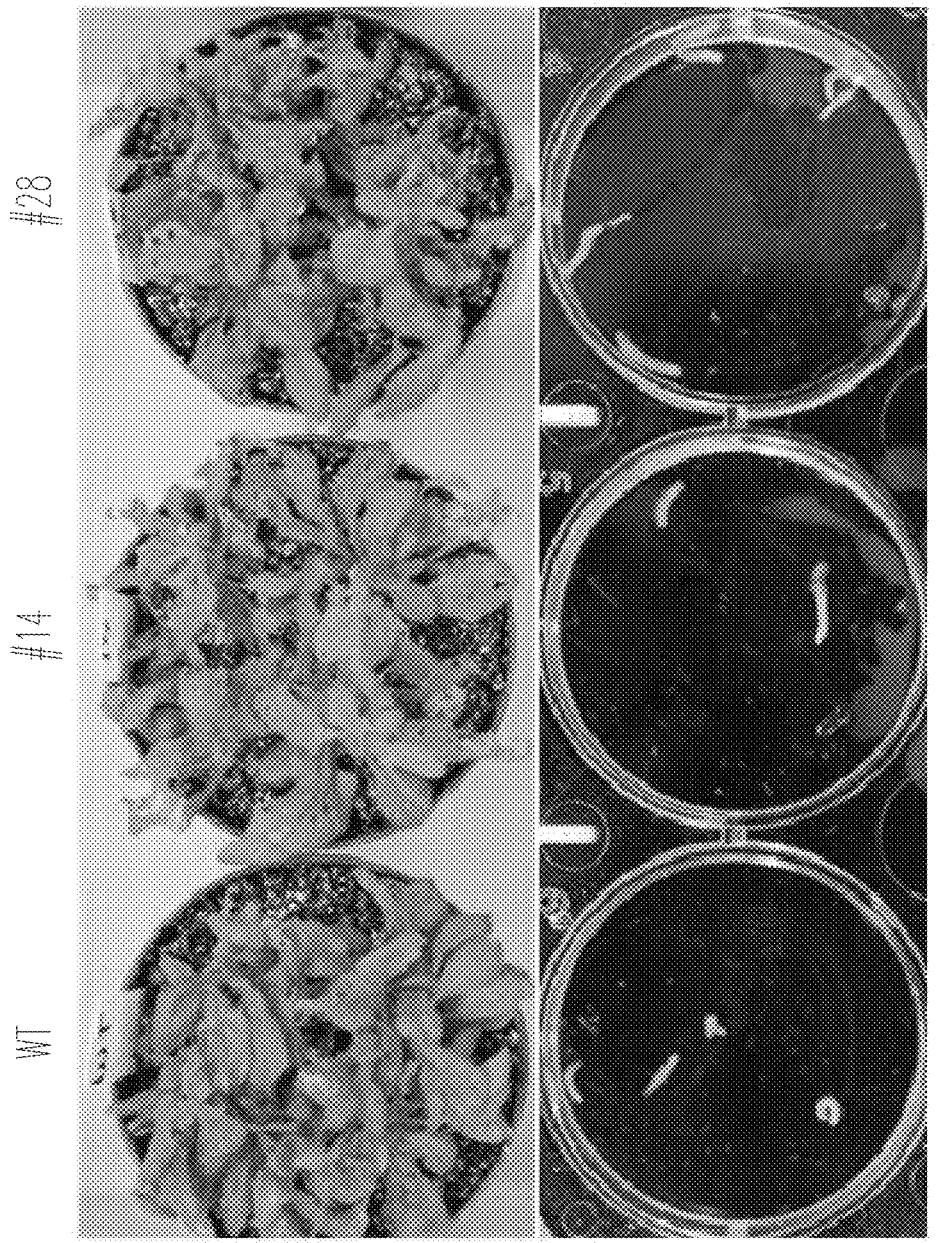
FIG. 5A shows a wild *Arabidopsis* plant compared to two transgenic *Arabidopsis* plants (#14 and #28) that express the WRINKLED1 transcription factor and the ADP-glucose pyrophosphorylase RNAi; each of these plants was contacted with *Spodoptera* (moth) larvae for 14 days. The amount of leaf damage observed for transgenic and wild type *Arabidopsis* plants was not significantly different.

FIG. 5A shows two transgenic *Arabidopsis* plants (#14 and #28) that express the WRINKLED1 transcription factor and the RNAi directed against ADP-glucose pyrophosphorylase transcripts, as well as one wild type plant. *Spodoptera* larvae were introduced onto each of these plants. After 14 days, the *Spodoptera* larvae were collected and the average larval weight was recorded.

Figure 5B:
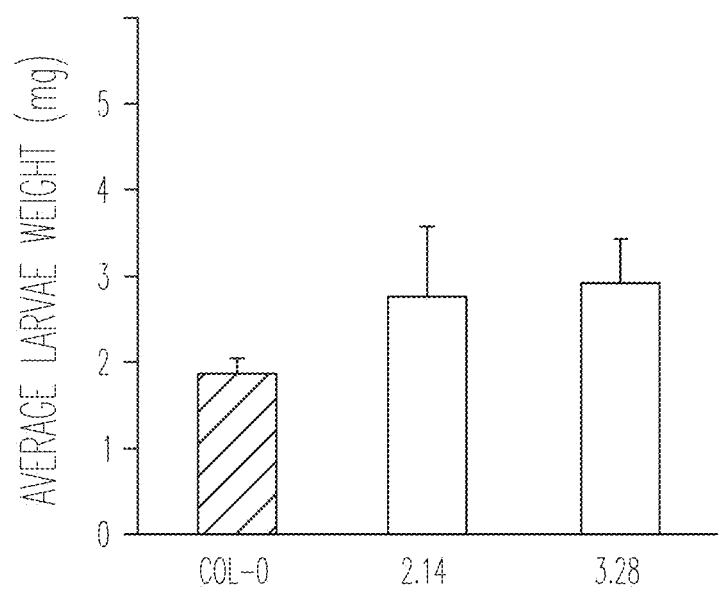
FIG. 5B graphically illustrates that the average larval weight of *Spodoptera* larvae grown on the transgenic plants (2.14 and 3.28) was significantly greater than the average weight of larvae grown on wild type plants.

As shown in FIG. 5B, while the average weight of larvae grown on wild type *Arabidopsis* was less than 2 mg, the average weight of larvae grown on the transgenic plants was close or equal to 3 mg.

There was no significant difference in insect damage to the different plants was observed. Thus, it does not appear that the insect larvae were more attracted to the transgenic plants or ate more of the transgenic plants.

These data indicate that transgenic plants that express the WRINKLED1 transcription factor and the RNAi directed against ADP-glucose pyrophosphorylase transcripts can be used as oil-rich, energy-rich fodder for efficient production of cattle and other foraging animals.

Example 6

Sugar Increases Oil Content of Transgenic Plants

Transgenic *Arabidopsis* were engineered to overproduce the transcription factor WRINKELED1 (WRI1) required for oil accumulation and reduced the expression of ADP-glucose pyrophosphorylase (AGPase) involved in starch biosynthesis using an RNAi approach in the leaf and roots, as described in the foregoing Examples.

Figure 6B:
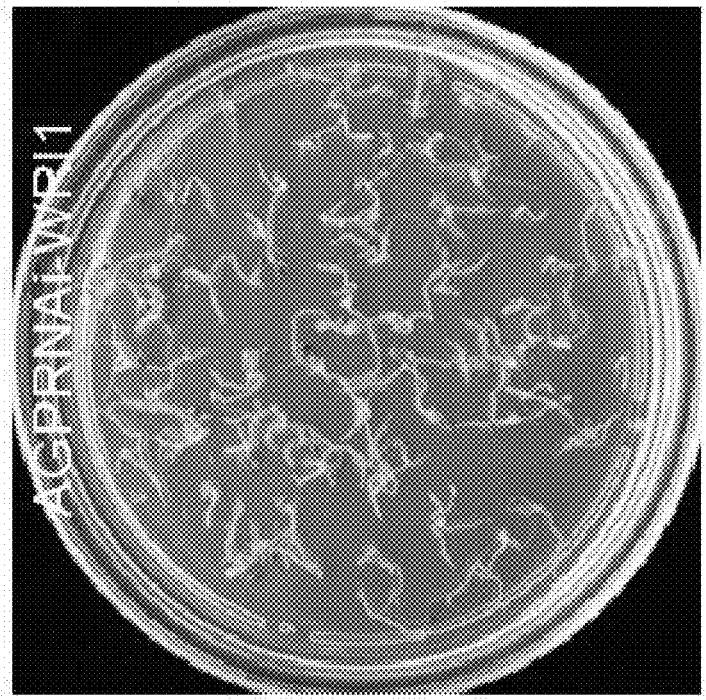
FIG. 6A-6B shows images of *Arabidopsis* wild type seedlings (FIG. 6A) and *Arabidopsis* seedlings that express the WRINKLED1 transcription factor and the ADP-glucose pyrophosphorylase RNAi (AGPRNAi-WRI1) (FIG. 6B) after 10 days growth on medium supplemented with 3% sugar.
Figure 6A:
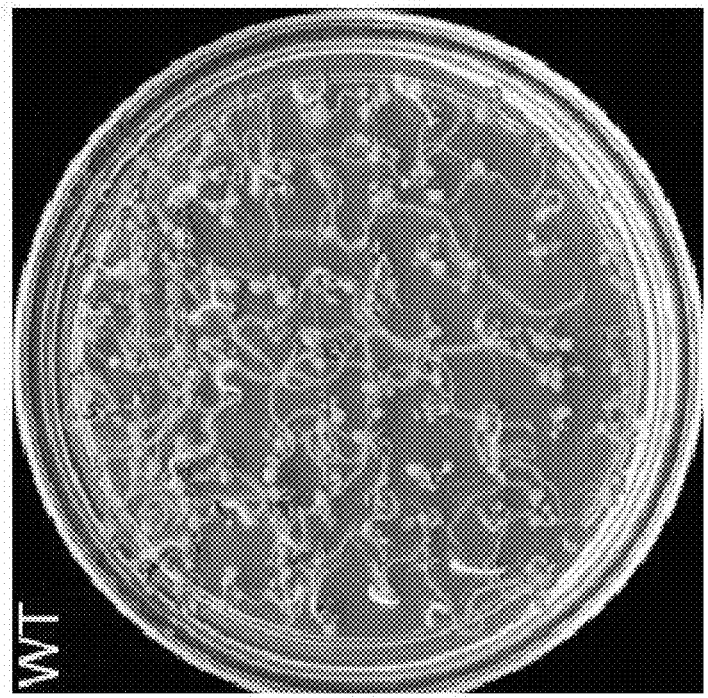
Figure 7:
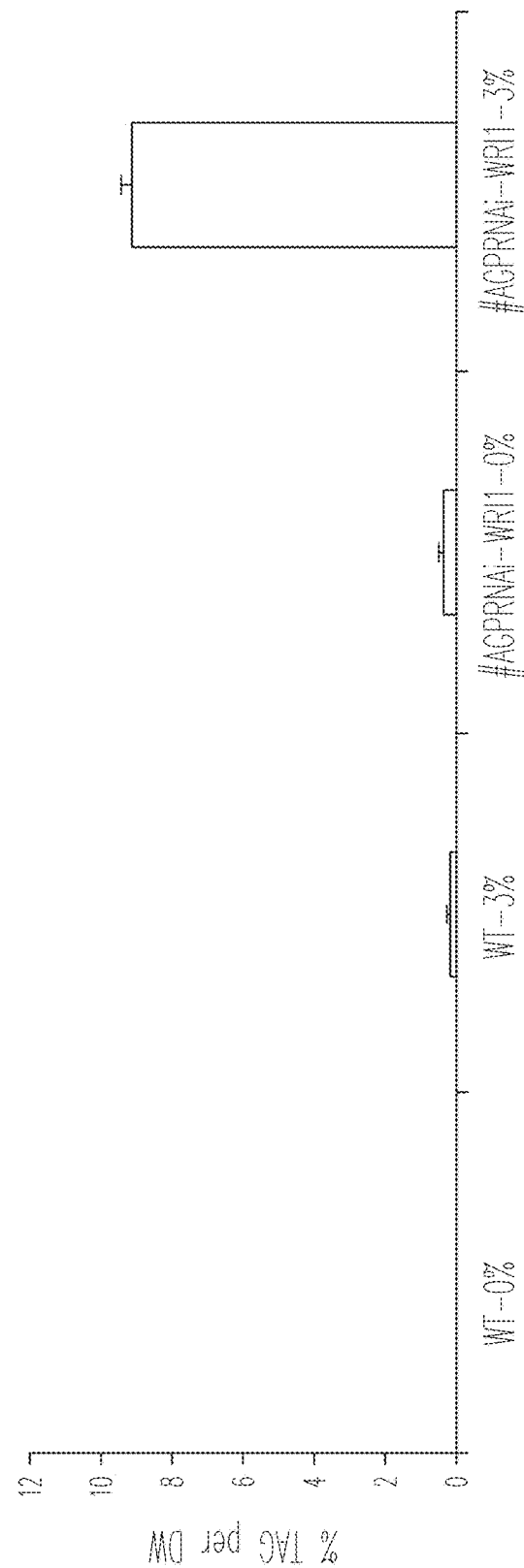
FIG. 7 graphically illustrates the percent oil (triacylglycerols per dry weight) in *Arabidopsis* wild type seedlings (WT) and in *Arabidopsis* seedlings that express the WRINKLED1 transcription factor and the ADP-glucose pyrophosphorylase RNAi (AGPRNAi-WRI1) when grown in normal growth medium without sucrose (0%) and in growth medium supplemented with 3% sucrose (3%). As shown, wild type plants had almost negligible levels of oil, but the AGPRNAi-WRI1 seedlings grown in media with 3% sucrose had up to 10% oil as a dry weight of plant material.

FIG. 7 shows that the resulting transgenic plants with AGPRNAi-WRI1 (double gene) accumulated less carbohydrate (starch) and more oil in the vegetative tissues. Interestingly, these AGPRNAi-WRI1 (double gene) transgenic plants developed very distinct phenotype when they are germinated and grown on a medium with 3% sucrose (FIG. 6A-6B). These double gene seedlings grown on 3% sucrose accumulated up to 10% TAG per dry weight with distinct oil droplets in the leaf tissue (FIG. 7). This approach can be used to convert sugar to oil in vegetative tissues.

REFERENCES

Abbadi, A., Domergue, F., Bauer, J., Napier, J. A., Welti, R., Zahringer, U., Cirpus, P. and Heinz, E. (2004) Biosynthesis of very-long-chain polyunsaturated fatty acids in transgenic oilseeds: constraints on their accumulation. Plant Cell, 16, 2734-2748.

Andrianov, V., Borisjuk, N., Pogrebnyak, N., Brinker, A., Dixon, J., Spitsin, S., Flynn, J., Matyszczuk, P., Andryszak, K., Laurelli, M., Golovkin, M. and Koprowski, H. (2010) Tobacco as a production platform for biofuel: overexpression of *Arabidopsis* DGAT and LEC2 genes increases accumulation and shifts the composition of lipids in green biomass. Plant Biotechnol. J. 8, 277-287.

Angeles-Nunez, J. G. and Tiessen, A. (2010) *Arabidopsis* sucrose synthase 2 and 3 modulate metabolic homeostasis and direct carbon towards starch synthesis in developing seeds. Planta, 232, 701-718.

Ballicora, M. A., Iglesias, A. A. and Preiss, J. (2004) ADP-glucose pyrophosphorylase: a regulatory enzyme for plant starch synthesis. Photosynth. Res. 79, 1-24.

Baud, S, and Lepiniec, L. (2010) Physiological and developmental regulation of seed oil production. Prog. Lipid Res. 49, 235-249.

Baud, S., Mendoza, M. S., To, A., Harscoet, E., Lepiniec, L. and Dubreucq, B. (2007) WRINKLED1 specifies the regulatory action of LEAFY COTYLEDON2 towards fatty acid metabolism during seed maturation in *Arabidopsis*. Plant J. 50, 825-838.

Baud, S., Wuilleme, S., To, A., Rochat, C. and Lepiniec, L. (2009) Role of WRINKLED1 in the transcriptional regulation of glycolytic and fatty acid biosynthetic genes in *Arabidopsis*. Plant J. 60, 933-947.

Baumlein, H., Misera, S., LierBen, H., Kolle, K., Horstmann, C., Wobus, U. and Muller, A. J. (1994) The FUS3 gene of *Arabidopsis thaliana* is a regulator of gene expression during late embryogenesis. Plant J. 6, 379-387.

Capell, T. and Christou, P. (2004) Progress in plant metabolic engineering. Curr. Opin. Biotechnol. 15, 148-154.

Cernac, A. and Benning, C. (2004) WRINKLED1 encodes an AP2/EREB domain protein involved in the control of storage compound biosynthesis in *Arabidopsis*. Plant J. 40, 575-585.

Cernac, A., Andre, C., Hoffmann-Benning, S, and Benning, C. (2006) WRI1 is required for seed germination and seedling establishment. Plant Physiol. 141, 745-757.

Clough, S. J. and Bent, A. F. (1998) Floral dip: a simplified method for *Agrobacterium*-mediated transformation of *Arabidopsis thaliana*. Plant J. 16, 735-743.

CRC Handbook of Chemistry and Physics (2008) Internet Version, 88th edn. (Lide, D., ed.). Boca Raton: CRC Press/Taylor and Francis.

Crevillen, P., Ventriglia, T., Pinto, F., Orea, A., Merida, A. and Romero, J. M. (2005) Differential pattern of expression and sugar regulation of *Arabidopsis thaliana* ADP-glucose pyrophosphorylase-encoding genes. J. Biol. Chem. 280, 8143-8149.

Durrett, T. P., Benning, C. and Ohlrogge, J. (2008) Plant triacylglycerols as feedstocks for the production of biofuels. Plant J. 54, 593-607.

Durrett, T. P., McClosky, D. D., Tumaney, A. W., Elzinga, D. A., Ohlrogge, J. and Pollard, M. (2010) A distinct DGAT with sn-3 acetyltransferase activity that synthesizes unusual, reduced-viscosity oils in Euonymus and transgenic seeds. Proc. Natl. Acad. Sci. USA, 107, 9464-9469.

Ekman, A., Hayden, D. M., Dehesh, K., Bulow, L. and Stymne, S. (2008) Carbon partitioning between oil and carbohydrates in developing oat (*Avena sativa* L.) seeds. J. Exp. Bot. 59, 4247-4257.

Focks, N. and Benning, C. (1998) wrinkledl: a novel, low-seed-oil mutant of *Arabidopsis* with a deficiency in the seed-specific regulation of carbohydrate metabolism. Plant Physiol. 118, 91-101.

Freedman, B. and Bagby, M. O. (1989) Heats of combustion of fatty esters and triglycerides. J. Am. Oil Chem. Soc. 66, 1601-1605.

Ihemere, U., Arias-Garzon, D., Lawrence, S, and Sayre, R. (2006) Genetic modification of cassava for enhanced starch production. Plant Biotechnol. J. 4, 453-465.

Jolivet, P., Roux, E., D'Andrea, S., Davanture, M., Negroni, L., Zivy, M. and Chardot, T. (2004) Protein composition of oil bodies in *Arabidopsis thaliana* ecotype WS. Plant Physiol. Biochem. 42, 501-509.

Koster-Topfer, M., Frommer, W. B., Rocha-Sosa, M., Rosahl, S., Schell, J. and Willmitzer, L. (1989) A class II patatin promoter is under developmental control in both transgenic potato and tobacco plants. Mol. Gen. Genet. 219, 390-396.

Liu, J., Hua, W., Zhan, G., Wei, F., Wang, X., Liu, G. and Wang, H. (2010) Increasing seed mass and oil content in transgenic *Arabidopsis* by the overexpression of wril-like gene from *Brassica napus*. Plant Physiol. Biochem. 48, 9-15.

Lowry, O. H. and Passonneau, J. V. (1972) A Flexible System of Enzymatic Analysis. Orlando, Fla.: Academic Press, 1-291.

Maeo, K., Tokuda, T., Ayame, A., Mitsui, N., Kawai, T., Tsukagoshi, H., Ishiguro, S, and Nakamura, K. (2009) An AP2-type transcription factor, WRINKLED1, of *Arabidopsis thaliana* binds to the AW-box sequence conserved among proximal upstream regions of genes involved in fatty acid synthesis. Plant J. 60, 476-487.

Masaki, T., Mitsui, N., Tsukagoshi, H., Nishii, T., Morikami, A. and Nakamura, K. (2005) ACTIVATOR of Spomin:: LUC 1/WRINKLED1 of *Arabidopsis thaliana* transactivates sugar-inducible promoters. Plant Cell Physiol. 46, 547-556.

Meinke, D. W., Franzmann, L. H., Nickle, T. C. and Yeung, E. C. (1994) Leafy cotyledon mutants of *Arabidopsis*. Plant Cell, 6, 1049-1064.

Mu, J., Tan, H., Zheng, Q., Fu, F., Liang, Y., Zhang, J., Yang, X., Wang, T., Chong, K., Wang, X. J. and Zuo, J. (2008) LEAFY COTYLEDON1 is a key regulator of fatty acid biosynthesis in *Arabidopsis*. Plant Physiol. 148, 1042-1054.

Ohlrogge, J. B. and Jaworski, J. G. (1997) Regulation of fatty acid synthesis. Annu. Rev. Plant Physiol Plant Mol. Biol. 48, 109-136.

Rolland, F., Baena-Gonzalez, E. and Sheen, J. (2006) Sugar sensing and signaling in plants: conserved and novel mechanisms. Annu. Rev. Plant Biol. 57, 675-709.

Ruuska, S. A., Girke, T., Benning, C. and Ohlrogge, J. B. (2002) Contrapuntal networks of gene expression during *Arabidopsis* seed filling. Plant Cell, 14, 1191-1206.

Shen, B., Allen, W. B., Zheng, P., Li, C., Glassman, K., Ranch, J., Nubel, D. and Tarczynski, M. C. (2010) Expression of ZmLEC1 and ZmWRI1 increases seed oil production in maize. Plant Physiol. 153, 980-987.

Slocombe, S. P., Comah, J., Pinfield-Wells, H., Soady, K., Zhang, Q., Gilday, A., Dyer, J. M. and Graham, I. A. (2009) Oil accumulation in leaves directed by modification of fatty acid breakdown and lipid synthesis pathways. Plant Biotechnol. J. 7, 694-703.

Smidansky, E. D., Clancy, M., Meyer, F. D., Lanning, S. P., Blake, N. K., Talbert, L. E. and Giroux, M. J. (2002) Enhanced ADP-glucose pyrophosphorylase activity in wheat endosperm increases seed yield. Proc. Natl. Acad. Sci. USA, 99, 1724-1729.

Smith, A. M. (2008) Prospects for increasing starch and sucrose yields for bioethanol production. Plant J. 54, 546-558.

Stark, D. M., Timmerman, K. P., Barry, G. F., Preiss, J. and Kishore, G. M. (1992) Regulation of the amount of starch in plant tissues by ADP glucose pyrophosphorylase. Science, 258, 287-292.

Stoller, E. W. and Weber, E. J. (1975) Differential cold tolerance, starch, sugar, protein, and lipid of yellow and purple nutsedge tubers. Plant Physiol. 55, 859-863.

Stone, S. L., Kwong, L. W., Yee, K. M., Pelletier, J., Lepiniec, L., Fischer, R. L., Goldberg, R. B. and Harada, J. J. (2001) LEAFY COTYLEDON2 encodes a B3 domain transcription factor that induces embryo development. Proc. Natl. Acad. Sci. USA, 98, 11806-11811.

Takenaga, F., Matsuyama, K., Abe, S., Torii, Y. and Itoh, S. (2008) Lipid and fatty acid composition of mesocarp and seed of avocado fruits harvested at northern range in Japan. J. Oleo. Sci. 57, 591-597.

Taylor, D. C., Francis, T., Guo, Y., Brost, J. M., Katavic, V., Mietkiewska, E., Michael, G. E., Lozinsky, S, and Hoffman, T. (2009) Molecular cloning and characterization of a KCS gene from Cardamine graeca and its heterologous expression in *Brassica* oilseeds to engineer high nervonic acid oils for potential medical and industrial use. Plant Biotechnol. J. 7, 925-938.

Thelen, J. J. and Ohlrogge, J. B. (2002) Metabolic engineering of fatty acid biosynthesis in plants. Metab. Eng. 4, 12-21.

Vigeolas, H., Mohlmann, T., Martini, N., Neuhaus, H. E. and Geigenberger, P. (2004) Embryo-specific reduction of ADP-Glc pyrophosphorylase leads to an inhibition of starch synthesis and a delay in oil accumulation in developing seeds of oilseed rape. Plant Physiol. 136, 2676-2686.

Wang, G., Lin, Q. and Xu, Y. (2007) *Tetraena mongolica* Maxim can accumulate large amounts of triacylglycerol in phloem cells and xylem parenchyma of stems. Phytochemistry, 68, 2112-2117.

Weigelt, K., Kuster, H., Rutten, T., Fait, A., Fernie, A. R., Miersch, O., Wasternack, C., Emery, R. J., Desel, C., Hosein, F., Muller, M., Saalbach, I. and Weber, H. (2009) ADP-glucose pyrophosphorylase-deficient pea embryos reveal specific transcriptional and metabolic changes of carbonnitrogen metabolism and stress responses. Plant Physiol. 149, 395-411.

Weise, S. E., Weber, A. P. and Sharkey, T. D. (2004) Maltose is the major form of carbon exported from the chloroplast at night. Planta, 218, 474-482.

Weselake, R. J., Taylor, D. C., Rahman, M. H., Shah, S., Laroche, A., McVetty, P. B. and Harwood, J. L. (2009) Increasing the flow of carbon into seed oil. Biotechnol. Adv. 27, 866-878.

Work, V. H., Radakovits, R., Jinkerson, R. E., Meuser, J. E., Elliott, L. G., Vinyard, D. J., Laurens, L. M., Dismukes, G. C. and Posewitz, M. C. (2010) Increased lipid accumulation in the *Chlamydomonas* reinhardtii sta7-10 starchless isoamylase mutant and increased carbohydrate synthesis in complemented strains. Eukaryot. Cell, 9, 1251-1261.

Xu, J., Francis, T., Mietkiewska, E., Giblin, E. M., Barton, D. L., Zhang, Y., Zhang, M. and Taylor, D. C. (2008) Cloning and characterization of an acyl-CoA-dependent diacylglycerol acyltransferase 1 (DGAT 1) gene from Tropaeolum majus, and a study of the functional motifs of the DGAT protein using site-directed mutagenesis to modify enzyme activity and oil content. Plant Biotechnol. J. 6, 799-818.

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The following embodiments of the invention are intended to describe some aspects of the invention.

EMBODIMENTS OF THE INVENTION

Embodiment 1

A method of increasing oil content in vegetative tissues of a plant, comprising genetically modifying the agricultural plant to comprise a plant expression system comprising
 (a) a first expression cassette comprising a nucleic acid segment encoding a WRINKLED1 transcription factor,
 (b) a second expression cassette comprising a nucleic acid segment encoding an inhibitory nucleic acid capable of hybridizing to an ADP-glucose pyrophosphorylase nucleic acid, or
 (c) a combination thereof,
 wherein a plant modified to contain the plant expression system produces more oil in vegetative tissues than an agricultural plant of the same agricultural plant species that has not been modified to contain the plant expression system.

Embodiment 2

The method of embodiment 1, wherein the plant expression system can inhibit expression or translation of ADP-glucose pyrophosphorylase mRNA in food plants, vegetable oil plants, and plants useful for forage or fodder.

Embodiment 3

The method of any of embodiments 1 or 2, wherein the plant expression system can inhibit expression or translation of ADP-glucose pyrophosphorylase mRNA in a *Brassicaceae* or other *Solanaceae* species.

Embodiment 4

The method of any of embodiments 1-3, wherein the plant expression system can inhibit expression or translation of ADP-glucose pyrophosphorylase mRNA in alfalfa, algae, avocado, barley, broccoli, Brussels sprouts, cabbage, canola, cassava, cauliflower, cole vegetables, collards, crucifers, grain legumes, forage grasses, jatropa, kale, kohlrabi, maize, miscanthus, mustards, nut sedge, oats, oil firewood trees, oilseeds, potato, radish, rice, rutabaga, sorghum, soybean, sugar beets, sugarcane, sunflower, switchgrass, tobacco, tomato, turnips, or wheat.

Embodiment 5

The method of any of embodiments 1-4, wherein the plant expression system does not inhibit expression or translation of ADP-glucose pyrophosphorylase mRNA in *Arabidopsis thaliana*.

Embodiment 6

The method of any of embodiments 1-5, wherein the agricultural plant is not *Arabidopsis thaliana*.

Embodiment 7

The method of any of embodiments 1-6, wherein food plants, vegetable oil plants, and plants useful for forage or fodder that comprise the plant expression system express higher levels of the WRINKLED1 transcription factor than a plant of the same species that has not been modified to contain the plant expression system.

Embodiment 8

The method of any of embodiments 1-7, wherein plants of *Brassicaceae* or other *Solanaceae* species that comprise the plant expression system express higher levels of the WRINKLED1 transcription factor than a plant of the same species that has not been modified to contain the plant expression system.

Embodiment 9

The method of any of embodiments 1-8, wherein plants selected from the group consisting of alfalfa, algae, avocado, barley, broccoli, Brussels sprouts, cabbage, canola, cassava, cauliflower, cole vegetables, collards, crucifers, grain legumes, forage grasses, jatropa, kale, kohlrabi, maize, miscanthus, mustards, nut sedge, oats, oil firewood trees, oilseeds, potato, radish, rice, rutabaga, sorghum, soybean, sugar beets, sugarcane, switchgrass, tobacco, tomato, turnips, and wheat that comprise the plant expression system express higher levels of the WRINKLED1 transcription factor than a plant of the same species that has not been modified to contain the plant expression system.

Embodiment 10

The method of any of embodiments 1-9, wherein the inhibitory nucleic acid can hybridize to any of the SEQ ID NO:2, 4 and 6 sequences, or to a complementary strand of any of the SEQ ID NO:2, 4, and 6 sequences under physiological conditions present in the agricultural plant.

Embodiment 11

The method of any of embodiments 1-10, wherein the inhibitory nucleic acid can hybridize to any of the SEQ ID NO:2, 4 and 6 sequences, or to a complementary strand of any of the SEQ ID NO:2, 4, and 6 sequences under stringent hybridization conditions.

Embodiment 12

The method of any of embodiments 1-11, wherein the inhibitory nucleic acid comprises nucleic acid segment consisting essentially of SEQ ID NO:4 in a 5' to 3' orientation linked to an linker that is linked to a second nucleic acid segment consisting essentially of SEQ ID NO:4 in a 3' to 5' orientation.

Embodiment 13

The method of any of embodiments 1-12, wherein the WRINKLED1 nucleic acids can hybridize to a nucleic acid comprising any of the SEQ ID NO:8, 10, 12, 14 and/or 18 sequences Embodiment 14

The method of any of embodiments 1-13, wherein the WRINKLED1 nucleic acids can hybridize under stringent conditions to a nucleic acid comprising any of the SEQ ID NO:8, 10, 12, 14 and/or 18 sequences.

Embodiment 15

The method of any of embodiments 1-14, wherein the plant has at at least about 1.2-fold, at least about 1.5-fold, least about 2-fold, at least about 3-fold, at least about 4-fold, at least about 5-fold, at least about 7-fold, at least about 10-fold, at least about 12-fold, at least about 15-fold, more oil, as measured by percent oil per dry weight, than a plant of the same species that has not been modified to contain the plant expression system Embodiment 16

The method of any of embodiments 1-15, wherein the plant has about 0.5% to about 20%, or about 1% to about 18%, or about 2% to about 15%, or about 3% to about 15%, or about 5% to about 15% oil content.

Embodiment 17

The method of any of embodiments 1-16, further comprising cultivating or growing the plant in the presence of sugar or a source of sugar.

Embodiment 18

The method of any of embodiments 1-17, further comprising cultivating or growing the plant in a medium comprising about 0.2% to about 10% sugar or about 0.2% to about 10% of a source of sugar.

Embodiment 19

A plant expression system comprising (1) a first expression cassette comprising a nucleic acid segment encoding a WRINKLED1 transcription factor, (2) a second expression cassette comprising a nucleic acid segment encoding an inhibitory nucleic acid capable of hybridizing to an ADP-glucose pyrophosphorylase nucleic acid, or (3) a combination thereof, wherein agricultural plants modified to contain the plant expression system produce more oil in vegetative tissues than an agricultural plant of the same agricultural plant species that has not been modified to contain the plant expression system.

Embodiment 20

The plant expression system of embodiment 19, wherein the plant expression system can inhibit expression or translation of ADP-glucose pyrophosphorylase mRNA in food plants, vegetable oil plants, and plants useful for forage or fodder.

Embodiment 21

The plant expression system of any of embodiments 19 or 20, wherein the plant expression system can inhibit expression or translation of ADP-glucose pyrophosphorylase mRNA in a *Brassicaceae* or other *Solanaceae* species.

Embodiment 22

The plant expression system of any of embodiments 19-21, wherein the plant expression system can inhibit expression or translation of ADP-glucose pyrophosphorylase mRNA in alfalfa, algae, avocado, barley, broccoli, Brussels sprouts, cabbage, canola, cassava, cauliflower, cole vegetables, collards, crucifers, grain legumes, forage grasses, jatropa, kale, kohlrabi, maize, miscanthus, mustards, nut sedge, oats, oil firewood trees, oilseeds, potato, radish, rice, rutabaga, sorghum, soybean, sugar beets, sugarcane, sunflower, switchgrass, tobacco, tomato, turnips, or wheat.

Embodiment 23

The plant expression system of any of embodiments 19-22, wherein the plant expression system does not inhibit expression or translation of ADP-glucose pyrophosphorylase mRNA in *Arabidopsis thaliana*.

Embodiment 24

The plant expression system of any of embodiments 19-23, wherein the agricultural plant is not *Arabidopsis thaliana*.

Embodiment 25

The plant expression system of any of embodiments 19-24, wherein food plants, vegetable oil plants, and plants useful for forage or fodder that comprise the plant expression system express higher levels of the WRINKLED1 transcription factor than a plant of the same species that has not been modified to contain the plant expression system.

Embodiment 26

The plant expression system of any of embodiments 19-25, wherein plants of *Brassicaceae* or other *Solanaceae* species that comprise the plant expression system express higher levels of the WRINKLED1 transcription factor than a plant of the same species that has not been modified to contain the plant expression system.

Embodiment 27

The plant expression system of any of embodiments 19-26, wherein plants selected from the group consisting of alfalfa, algae, avocado, barley, broccoli, Brussels sprouts, cabbage, canola, cassava, cauliflower, cole vegetables, collards, crucifers, grain legumes, forage grasses, jatropa, kale, kohlrabi, maize, miscanthus, mustards, nut sedge, oats, oil firewood trees, oilseeds, potato, radish, rice, rutabaga, sorghum, soybean, sugar beets, sugarcane, sunflower, switchgrass, tobacco, tomato, turnips, and wheat that comprise the plant expression system express higher levels of the WRINKLED1 transcription factor than a plant of the same species that has not been modified to contain the plant expression system.

Embodiment 28

The plant expression system of any of embodiments 19-27, wherein the inhibitory nucleic acid can hybridize to any of the SEQ ID NO:2, 4 and 6 sequences, or to a complementary strand of any of the SEQ ID NO:2, 4, and 6 sequences under physiological conditions present in the agricultural plant.

Embodiment 29

The plant expression system of any of embodiments 19-28, wherein the inhibitory nucleic acid can hybridize to any of the SEQ ID NO:2, 4 and 6 sequences, or to a complementary strand of any of the SEQ ID NO:2, 4, and 6 sequences under stringent hybridization conditions.

Embodiment 30

The plant expression system of any of embodiments 19-29, wherein the inhibitory nucleic acid comprises nucleic acid segment consisting essentially of SEQ ID NO:4 in a 5' to 3' orientation linked to an linker that is linked to a second nucleic acid segment consisting essentially of SEQ ID NO:4 in a 3' to 5' orientation.

Embodiment 31

The plant expression system of any of embodiments 19-30, wherein the WRINKLED1 nucleic acids can hybridize to a nucleic acid comprising any of the SEQ ID NO:8, 10, 12, 14 and/or 18 sequences

Embodiment 32

The plant expression system of any of embodiments 19-31, wherein the WRINKLED1 nucleic acids can hybridize under stringent conditions to a nucleic acid comprising any of the SEQ ID NO:8, 10, 12, 14 and/or 18 sequences.

Embodiment 33

The plant expression system of any of embodiments 19-32, wherein a plant comprising the plant expression system has at least about 1.2-fold, at least about 1.5-fold, least about 2-fold, at least about 3-fold, at least about 4-fold, at least about 5-fold, at least about 7-fold, at least about 10-fold, at least about 12-fold, at least about 15-fold, more oil, as measured by percent oil per dry weight, than a plant of the same species that has not been modified to contain the plant expression system

Embodiment 34

The plant expression system of any of embodiments 19-33, wherein a plant comprising the plant expression system has about 0.5% to about 20%, or about 1% to about 18%, or about 2% to about 15%, or about 3% to about 15%, or about 5% to about 15% oil content.

Embodiment 35

A plant cell comprising the plant expression system of any of embodiments 19-34.

Embodiment 36

The plant cell of embodiment 35, wherein the plant cell is a cell from a food plant species, vegetable oil plant species, or a plant species useful for forage or fodder.

Embodiment 37

The plant cell of any of embodiments 35 or 36, wherein the plant cell is a cell from a *Brassicaceae* or other *Solanaceae* species.

Embodiment 38

The plant cell of any of embodiments 35-37, wherein the plant cell is a cell from an alfalfa, algae, avocado, barley, broccoli, Brussels sprouts, cabbage, canola, cassava, cauliflower, cole vegetables, collards, crucifers, grain legumes, forage grasses, jatropa, kale, kohlrabi, maize, miscanthus, mustards, nut sedge, oats, oil firewood trees, oilseeds, potato, radish, rice, rutabaga, sorghum, soybean, sugar beets, sugarcane, sunflower, switchgrass, tobacco, tomato, turnips, or wheat species.

Embodiment 39

The plant cell of any of embodiments 35-38, wherein the plant cell is not an *Arabidopsis thaliana* plant cell.

Embodiment 40

An agricultural plant comprising the plant expression system of any of embodiments 19-34.

Embodiment 41

An agricultural plant comprising the plant cell of any of embodiments 35-39.

Embodiment 42

Vegetative tissue comprising the plant expression system of any of embodiments 19-34.

Embodiment 43

Vegetative tissue comprising the plant cell of any of embodiments 35-39.

Embodiment 44

A seed comprising the plant expression system of any of embodiments 19-34.

Embodiment 45

A method of increasing oil content in vegetative tissues of a plant, comprising inducing expression of a heterologous WRINKLED1 transcription factor, a heterologous inhibitory nucleic acid capable of hybridizing to an ADP-glucose pyrophosphorylase nucleic acid, or a combination thereof in at least one vegetative tissue of the plant, to thereby increase oil content in the vegetative tissues of the plant.

The specific compositions and methods described herein are representative, exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by embodiments and optional features, modification and variation of the concepts herein disclosed may be resorted to by those skilled in the art, and that such modifications and variations are considered to be within the scope of this invention as defined by the appended claims and statements of the invention.

The invention illustratively described herein may be practiced in the absence of any element or elements, or limitation or limitations, which is not specifically disclosed herein as essential. The methods and processes illustratively described herein may be practiced in differing orders of steps, and the methods and processes are not necessarily restricted to the orders of steps indicated herein or in the claims.

As used herein and in the appended claims, the singular forms "a," "an," and "the" include plural reference unless the context clearly dictates otherwise. Thus, for example, a reference to "a compound" or "a catalyst" or "a ligand" includes a plurality of such compounds, catalysts or ligands, and so forth. In this document, the term "or" is used to refer to a nonexclusive or, such that "A or B" includes "A but not B," "B but not A," and "A and B," unless otherwise indicated.

Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group.

The Abstract is provided to comply with 37 C.F.R. §1.72(b) to allow the reader to quickly ascertain the nature and gist of the technical disclosure. The Abstract is submitted with the understanding that it will not be used to interpret or limit the scope or meaning of the claims.

---

What is claimed:

1. A method of increasing oil content in vegetative tissues of a plant, comprising genetically modifying the plant to comprise a plant expression system, or inducing expression of a plant expression system, wherein the plant expression system comprises a combination of:
   (a) a first expression cassette comprising a nucleic add segment encoding a WRINKLED 1 transcription factor with at least 95% sequence identity to the amino add sequences of SEQ ID NO: 7, 9, or 11, and
   (b) a second expression cassette comprising a nucleic add segment encoding an inhibitory nucleic add comprising a nucleic add with at least 95% sequence identity to at least 20 nucleotides of the nucleotide sequence SEQ ID NO: 2 or 6 encoding an ADP-glucose pyrophosphorylases;
   wherein the plants modified to contain or induced to express the plant expression system produce at least 10-fold more oil in vegetative tissues than a plant of the same species that has not been modified to contain the plant expression system.

2. The method of claim 1, wherein the plant expression system inhibits expression or translation of ADP-glucose pyrophosphorylase mRNA in food plants, vegetable oil plants, and plants useful for forage or fodder.

3. The method of claim 1, wherein the plant expression system inhibits expression or translation of ADP-glucose pyrophosphorylase mRNA in a *Brassicaceae* or *Solanaceae* species.

4. The method of claim 1, wherein the plant expression system inhibits expression or translation of ADP-glucose pyrophosphorylase mRNA in alfalfa, algae, avocado, barley, broccoli, Brussels sprouts, cabbage, canola, cassava, cauliflower, cole vegetables, collards, crucifers, grain legumes, forage grasses, jatropa, kale, kohlrabi, maize, miscanthus, mustards, nut sedge, oats, oil firewood trees, oilseeds, potato, radish, rice, rutabaga, sorghum, soybean, sugar beets, sugarcane, sunflower, switchgrass, tobacco, tomato, turnips, or wheat.

5. The method of claim 1, wherein the plants comprising the plant expression system express higher levels of the WRINKLED1 transcription factor than a plant of the same species that has not been modified to contain the plant expression system.

6. The method of claim 1, wherein plants of *Brassicaceae* or *Solanaceae* species that comprise the plant expression system express higher levels of the WRINKLED1 transcription factor than plants of the same species that have not been modified to contain the plant expression system.

7. The method of claim 1, wherein the plant is selected from the group consisting of alfalfa, algae, avocado, barley, broccoli, Brussels sprouts, cabbage, canola, cassava, cauliflower, cole vegetables, collards, crucifers, grain legumes, forage grasses, jatropa, kale, kohlrabi, maize, miscanthus, mustards, nut sedge, oats, oil firewood trees, oilseeds, potato, radish, rice, rutabaga, sorghum, soybean, sugar beets, sugarcane, switchgrass, tobacco, tomato, turnips, and wheat and express higher levels of the WRINKLED1 transcription factor than a plant of the same species that has not been modified to contain the plant expression system.

8. The method of claim 1, wherein the inhibitory nucleic add inhibits expression or translation of an mRNA with SEQ ID NO: 2 or 6 under physiological conditions present in the plant.

9. The method of claim 1, further comprising contacting the plant with sugar or a sugar source.

10. A plant expression system comprising:
   (a) a first expression cassette comprising a nucleic acid segment encoding a WRINKLED1 transcription factor with at least 95% sequence identity to the amino acid sequences of SEQ ID NO: 7, 9, or 11, and
   (b) a second expression cassette comprising a nucleic acid segment encoding an inhibitory nucleic acid comprising a nucleic acid with at least 95% sequence identity to the nucleotide sequence of SEQ ID NO: 2 or 6 encoding an ADP-glucose pyrophosphorylase,
   wherein the plant expression system produces at least 10-fold more oil in plant vegetative tissues compared to plant vegetative tissues that have not been modified to contain the plant expression system.

11. The plant expression system of claim 10, wherein the plant expression system inhibits expression or translation of ADP-glucose pyrophosphorylase mRNA in food plants, vegetable oil plants, and plants useful for forage or fodder.

12. The plant expression system of claim 10, wherein the plant expression system inhibits expression or translation of ADP-glucose pyrophosphorylase mRNA in a *Brassicaceae* or *Solanaceae* species.

13. The plant expression system of claim 10, wherein the plant expression system inhibits expression or translation of ADP-glucose pyrophosphorylase mRNA in alfalfa, algae, avocado, barley, broccoli, Brussels sprouts, cabbage, canola, cassava, cauliflower, cole vegetables, collards, crucifers, grain legumes, forage grasses, jatropa, kale, kohlrabi, maize, miscanthus, mustards, nut sedge, oats, oil firewood trees, oilseeds, potato, radish, rice, rutabaga, sorghum, soybean, sugar beets, sugarcane, switchgrass, tobacco, tomato, turnips, or wheat.

14. The plant expression system of claim 10, wherein the plant is not *Arabidopsis thaliana*.

15. The plant expression system of claim 10, wherein the plant vegetative tissues that comprise the plant expression system express higher levels of the WRINKLED1 transcription factor than plant vegetative tissues of the same species that have not been modified to contain the plant expression system.

16. The plant expression system of claim 10, wherein plants of *Brassicaceae* or *Solanaceae* species that comprise the plant expression system express higher levels of the WRINKLED 1 transcription factor than a plant of the same species that has not been modified to contain the plant expression system.

17. The plant expression system of claim 10, wherein plants selected from the group consisting of alfalfa, algae, avocado, barley, broccoli, Brussels sprouts, cabbage, canola, cassava, cauliflower, cole vegetables, collards, crucifers, grain legumes, forage grasses, jatropa, kale, kohlrabi, maize, miscanthus, mustards, nut sedge, oats, oil firewood trees, oilseeds, potato, radish, rice, rutabaga, sorghum, soybean, sugar beets, sugarcane, switchgrass, tobacco, tomato, turnips, and wheat that comprise the plant expression system express higher levels of the WRINKLED1 transcription factor than a plant of the same species that has not been modified to contain the plant expression system.

18. The plant expression system of claim 10, wherein the inhibitory nucleic add inhibits expression or translation of an mRNA with SEQ ID NO: 2 or 6 under physiological conditions.

19. A plant cell or seed comprising the plant expression system of claim 10, wherein the cell or seed is not an *Arabidopsis thaliana* cell or seed.

20. The plant cell or seed of claim 19, wherein the plant cell or seed is from a food plant species, vegetable oil plant species, or a plant species useful for forage or fodder.

21. The plant cell or seed of claim 19, wherein the plant cell or seed is from a *Brassicaceae* or *Solanaceae* species.

22. The plant cell or seed of claim 19, wherein the plant cell or seed is from an alfalfa, algae, avocado, barley, broccoli, Brussels sprouts, cabbage, canola, cassava, cauliflower, cole vegetables, collards, crucifers, grain legumes, forage grasses, jatropa, kale, kohlrabi, maize, miscanthus, mustards, nut sedge, oats, oil firewood trees, oilseeds, potato, radish, rice, rutabaga, sorghum, soybean, sugar beets, sugarcane, sunflower, switchgrass, tobacco, tomato, turnips, or wheat species.

23. The plant cell or seed of claim 19, wherein the plant cell or seed is not an *Arabidopsis thaliana* plant cell or seed.

24. A plant comprising the plant expression system of claim 10, wherein the plant is not an *Arabidopsis thaliana* plant.

25. A plant comprising the plant cell of claim 19.

26. A plant vegetative tissue comprising the plant expression system of claim 10, wherein the vegetative tissue is not *Arabidopsis thaliana* vegetative tissue.

27. A plant vegetative tissue comprising the plant cell of claim 19.

28. A plant comprising a plant expression system that comprises a combination of:
(a) a first expression cassette comprising a nucleic acid segment encoding a WRINKLED 1 transcription factor with at least 95% sequence identity to the amino acid sequences of SEQ ID NO: 7, 9, or 11; and
(b) a second expression cassette comprising a nucleic acid segment encoding an inhibitory nucleic add comprising a nucleic add with at least 95% sequence identity to at least 20 nucleotides of the nucleotide sequence SEQ ID NO: 2 or 6 encoding an ADP-glucose pyrophosphorylase;
wherein the plant is a food plant, vegetable oil plant, forage plant, or fodder plant, and the plant's vegetative tissues have at least 10-fold more oil than a plant of the same species that does not contain the plant expression system.

29. A seed comprising a plant expression system that comprises a combination of:
(a) a first expression cassette comprising a nucleic acid segment encoding a WRINKLED 1 transcription factor with at least 95% sequence identity to the amino acid sequences SEQ ID NO: 7, 9, or 11; and
(b) a second expression cassette comprising a nucleic add segment encoding an inhibitory nucleic add comprising a nucleic add with at least 95% sequence identity to at least 20 nucleotides of the nucleotide sequence SEQ ID NO: 2 or 6 encoding an ADP-glucose pyrophosphorylase;
wherein the seed develops into a food plant, vegetable oil plant, forage plant, or fodder plant with vegetative tissues that have at least 10-fold more oil than a plant developed from a seed of the same species that does not contain the plant expression system.

30. The method of claim 1, where the oil content is measured by percent oil per dry weight.

31. A plant grown from the seed of claim 19.

* * * * *

UNITED STATES PATENT AND TRADEMARK OFFICE
CERTIFICATE OF CORRECTION

PATENT NO. : 9,657,304 B2
APPLICATION NO. : 13/938784
DATED : May 23, 2017
INVENTOR(S) : Benning et al.

Page 1 of 1

It is certified that error appears in the above-identified patent and that said Letters Patent is hereby corrected as shown below:

In Column 119, Line 25, in Claim 1, delete "add" and insert --acid-- therefor

In Column 119, Line 27, in Claim 1, delete "add" and insert --acid-- therefor

In Column 119, Line 29, in Claim 1, delete "add" and insert --acid-- therefor

In Column 119, Line 30, in Claim 1, delete "add" and insert --acid-- therefor

In Column 119, Line 31, in Claim 1, delete "add" and insert --acid-- therefor

In Column 119, Line 33-34, in Claim 1, delete "pyrophosphorylases;" and insert --pyrophosphorylase;-- therefor In Column 120, Line 31, in Claim 8, delete "add" and insert --acid-- therefor In Column 121, Line 28, in Claim 18, delete "add" and insert --acid-- therefor In Column 122, Line 18, in Claim 28, delete "add" and insert --acid-- therefor In Column 122, Line 19, in Claim 28, delete "add" and insert --acid-- therefor In Column 122, Line 35, in Claim 29, delete "add" and insert --acid-- therefor In Column 122, Line 36, in Claim 29, delete "add" and insert --acid-- therefor In Column 122, Line 37, in Claim 29, delete "add" and insert --acid-- therefor Signed and Sealed this
Eighth Day of May, 2018

Andrei Iancu
*Director of the United States Patent and Trademark Office*

SEQUENCE LISTING

<160> NUMBER OF SEQ ID NOS: 44

<210> SEQ ID NO 1
<211> LENGTH: 521
<212> TYPE: PRT
<213> ORGANISM: Zea mays

<400> SEQUENCE: 1

Met Gln Phe Ser Ser Val Leu Pro Leu Glu Gly Lys Ala Cys Met Ser
 1               5                  10                  15

Pro Val Arg Arg Gly Ser Gly Gly Tyr Gly Ser Glu Arg Met Arg Ile
             20                  25                  30

-continued

```
Asn Cys Cys Ser Ile Arg Arg Asn Lys Ala Leu Arg Met Cys Phe
         35                  40                  45

Ser Ala Arg Gly Ala Val Ser Ser Thr Gln Cys Val Leu Thr Ser Asp
 50                  55                  60

Ala Gly Pro Asp Thr Leu Val Arg Pro Asn His Pro Phe Arg Arg Asn
 65                  70                  75                  80

Tyr Ala Asp Pro Asn Glu Val Ala Ala Val Ile Leu Gly Gly Gly Thr
                 85                  90                  95

Gly Thr Gln Leu Phe Pro Leu Thr Ser Thr Arg Ala Thr Pro Ala Val
             100                 105                 110

Pro Ile Gly Gly Cys Tyr Arg Leu Ile Asp Ile Pro Met Ser Asn Cys
         115                 120                 125

Phe Asn Ser Gly Ile Asn Lys Ile Phe Val Met Thr Gln Phe Asn Ser
130                 135                 140

Ala Ser Leu Asn Arg His Ile His Arg Thr Tyr Leu Gly Gly Gly Ile
145                 150                 155                 160

Asn Phe Thr Asp Gly Ser Val Glu Val Leu Ala Ala Thr Gln Met Pro
                 165                 170                 175

Gly Glu Ala Ala Gly Trp Phe Gln Gly Thr Ala Asp Ala Val Arg Lys
             180                 185                 190

Phe Ile Trp Val Leu Glu Asp Tyr Tyr Lys His Lys Ala Ile Glu His
         195                 200                 205

Ile Leu Ile Leu Ser Gly Asp Gln Leu Tyr Arg Met Asp Tyr Met Glu
     210                 215                 220

Leu Val Gln Lys His Val Asp Asp Asn Ala Asp Ile Thr Leu Ser Cys
225                 230                 235                 240

Ala Pro Val Gly Glu Ser Arg Ala Ser Asp Tyr Gly Leu Val Lys Phe
                 245                 250                 255

Asp Ser Ser Gly Arg Val Ile Gln Phe Ser Glu Lys Pro Lys Gly Ala
             260                 265                 270

Ala Leu Glu Glu Met Lys Val Asp Thr Ser Phe Leu Asn Phe Ala Thr
         275                 280                 285

Cys Thr Leu Pro Ala Glu Tyr Pro Tyr Ile Ala Ser Met Gly Val Tyr
290                 295                 300

Val Phe Lys Arg Asp Val Leu Leu Asp Leu Leu Lys Ser Arg Tyr Ala
305                 310                 315                 320

Glu Leu His Asp Phe Gly Ser Glu Ile Leu Pro Lys Ala Leu His Glu
                 325                 330                 335

His Asn Val Gln Ala Tyr Val Phe Thr Asp Tyr Trp Glu Asp Ile Gly
             340                 345                 350

Thr Ile Arg Ser Phe Phe Asp Ala Asn Met Ala Leu Cys Glu Gln Pro
         355                 360                 365

Pro Lys Phe Glu Phe Tyr Asp Pro Lys Thr Pro Phe Phe Thr Ser Pro
370                 375                 380

Arg Tyr Leu Pro Pro Thr Lys Ser Asp Lys Cys Arg Ile Lys Asp Ala
385                 390                 395                 400

Ile Ile Ser His Gly Cys Phe Leu Arg Glu Cys Ala Ile Glu His Ser
                 405                 410                 415

Ile Val Gly Val Pro Ser Arg Leu Asn Ser Gly Cys Glu Leu Lys Asn
             420                 425                 430

Thr Met Met Met Gly Ala Asp Leu Tyr Glu Thr Glu Asp Glu Ile Ser
         435                 440                 445

Arg Leu Leu Ala Glu Gly Lys Val Pro Ile Gly Val Gly Glu Asn Thr
```

```
                450           455           460
Lys Ile Ser Asn Cys Ile Ile Asp Met Asn Cys Gln Gly Trp Lys Glu
465                 470                 475                 480

Arg Leu His Asn Lys Gln Arg Gly Arg Ser Lys Ser Pro Asp Arg Pro
                485                 490                 495

Gly Arg Arg Ile Leu Ile Arg Ser Gly Ile Val Val Leu Lys Asn
            500                 505                 510

Ala Thr Ile Lys Asp Gly Thr Val Ile
        515                 520

<210> SEQ ID NO 2
<211> LENGTH: 2123
<212> TYPE: DNA
<213> ORGANISM: Zea mays

<400> SEQUENCE: 2
```

| | | | | | |
|---|---|---|---|---|---|
| ggctcgctcg | ccttcctcct | ccccactcca | ctccattcca | acgcaacgcc | tcgccccgct | 60 |
| ttataggccg | ccgcccgcgc | cacatcgcca | ccgtctcgca | ccgtcgcggc | cacccattct | 120 |
| ctctcgtcca | tcgcatcgct | ccggctccca | gcgcaatcga | tccatccgtc | cctaggtgtg | 180 |
| cttcagctat | gcagttcagc | agcgtgcttc | ccctagaggg | aaaagcgtgt | atgagcccag | 240 |
| tgaggagagg | cagtggaggt | tatgggagtg | agaggatgag | gatcaactgc | tgcagcatca | 300 |
| ggcgcaacaa | ggcactgagg | aggatgtgtt | tcagtgcaag | gggtgctgtg | agcagcacgc | 360 |
| agtgtgtgct | cacatcagat | gctggcccag | acactcttgt | acgtccgaac | catccttttc | 420 |
| ggaggaatta | tgctgatcct | aatgaagtcg | ctgccgtcat | tttgggtggt | ggtaccggga | 480 |
| ctcagctttt | ccctctcaca | agcacaaggg | ccaccctgc | tgttcctatt | ggaggatgtt | 540 |
| acaggctat | tgatatcccc | atgagcaact | gtttcaacag | tggcataaac | aagatatttg | 600 |
| ttatgactca | gttcaactca | gcttctctta | accgtcacat | tcatcgtacc | tatcttggtg | 660 |
| gggggatcaa | cttcactgat | ggatctgttg | aggtgctggc | tgcaacacaa | atgcctgggg | 720 |
| aggctgctgg | ttggttccag | ggcacagcag | acgccgttag | aaaatttatc | tgggtacttg | 780 |
| aggattatta | caagcataaa | gctatagaac | acattttgat | tttgtcagga | gatcaactct | 840 |
| atcgtatgga | ttacatggag | cttgtgcaga | acatgtcga | tgacaatgca | gacataactt | 900 |
| tatcatgcgc | tcctgttgga | gagagtcgag | catctgacta | tggattagtt | aagttcgata | 960 |
| gttcaggccg | tgtaattcag | ttctctgaga | accaaaggg | tgctgccttg | aagaaatga | 1020 |
| aagtggatac | cagcttcctc | aatttcgcca | cttgcactct | cccagctgaa | tatccctata | 1080 |
| tcgcttcaat | gggagtttac | gttttaaga | gagatgtttt | gttagacctt | ctaaagtcac | 1140 |
| ggtatgctga | actgcatgac | tttggttctg | aaattctgcc | caaggctttg | catgagcaca | 1200 |
| atgtacaggc | atatgttttc | actgactact | gggaggacat | tggaacaatc | agatctttct | 1260 |
| ttgatgcaaa | catggccctc | tgcgagcagc | ctccaaagtt | cgagttttac | gatccgaaaa | 1320 |
| caccattctt | cacttcccct | cggtacttgc | caccaacgaa | gtcggataag | tgcaggatta | 1380 |
| aagacgcgat | catttcacac | ggctgcttct | tgcgtgagtg | tgccatcgag | cactctattg | 1440 |
| ttggtgttcc | gtcacgccta | aactctggat | gcgagctcaa | gaataccatg | atgatgggtg | 1500 |
| cggatttgta | tgagaccgaa | gacgagatct | caaggctact | ggcagagggc | aaggtgccaa | 1560 |
| ttggcgtagg | ggagaacacg | aagataagca | actgcatcat | cgacatgaat | tgccagggtt | 1620 |
| ggaaggaacg | tctccataac | aaacaaagag | gggcgttcca | agagtcccga | cggcctggac | 1680 |
| gaaggatact | aatccggtct | gggatcgtgg | tagtcctgaa | gaacgcaacc | atcaaggacg | 1740 |

```
gcaccgtcat atagagacta actttggcct tacgcatggc ctgcaaggtt acaggttagt    1800
catcgtcttg agagttgaga cttagtttga ggcgcgcccg accttgactt gagccgtcgg    1860
agggacaaga acatgaggaa gaagggctgg tggtgccgga tgttgccatg gacgacgaga    1920
aatggtttgg ctggtcgcat cggtccagta gctagctctt ccgatgttat taatatatgt    1980
atctagtgga gtagtgcgaa cagtgcaata agctgggcga gcaaagccgc ggcaactctt    2040
ggcttgggga ttggttggtg catcttgtaa ataataaact cggacgcagc aaatgaaaca    2100
tgcccctcat cttcttccaa aaa                                             2123
```

<210> SEQ ID NO 3
<211> LENGTH: 166
<212> TYPE: PRT
<213> ORGANISM: Brassica napus

<400> SEQUENCE: 3

```
Asp Tyr Glu Lys Phe Ile Gln Ala His Arg Glu Thr Asp Ala Asp Ile
 1               5                  10                  15

Thr Val Ala Ala Leu Pro Met Asp Glu Lys Arg Ala Thr Ala Phe Gly
                20                  25                  30

Leu Met Lys Ile Asp Asp Glu Gly Arg Ile Ile Glu Phe Ala Glu Lys
            35                  40                  45

Pro Lys Gly Glu Gln Leu Lys Ala Met Lys Val Asp Thr Thr Ile Leu
        50                  55                  60

Gly Leu Asp Asp Glu Arg Ala Lys Glu Met Pro Phe Ile Ala Ser Met
65                  70                  75                  80

Gly Ile Tyr Val Val Ser Lys Asn Val Met Leu Asp Leu Leu Arg Asp
                85                  90                  95

Gln Phe Pro Gly Ala Asn Asp Phe Gly Ser Glu Val Ile Pro Gly Ala
               100                 105                 110

Thr Asp Leu Gly Leu Arg Val Gln Ala Tyr Leu Tyr Asp Gly Tyr Trp
           115                 120                 125

Glu Asp Ile Gly Thr Ile Glu Ala Phe Tyr Asn Ala Asn Leu Gly Ile
       130                 135                 140

Thr Lys Lys Pro Val Pro Asp Phe Ser Phe Tyr Asp Arg Ser Ala Pro
145                 150                 155                 160

Ile Tyr Thr Gln Pro Arg
                165
```

<210> SEQ ID NO 4
<211> LENGTH: 500
<212> TYPE: DNA
<213> ORGANISM: Brassica napus

<400> SEQUENCE: 4

```
ggactacgag aagttcattc aagcgcatcg tgagaccgac gctgatatca ctgttgctgc      60
tcttcctatg gatgagaaac gtgccacggc ttttggactt atgaagattg atgacgaagg     120
aaggatcatt gagtttgctg agaagcctaa aggagagcag ttaaaggcta tgaaggttga     180
tacaacaatc ttgggacttg atgacgaaag ggccaaagag atgccctta ttgctagtat      240 ggggatatat gttgttagca agaatgtgat gttggacttg ctccgagacc agttccctgg     300
agctaatgac ttcgggagtg aagttatccc tggtgctact gatcttggac tcagagtgca     360
agcttatctg tatgatggat actgggaaga tattggtacc attgaagcct ttacaatgc      420 taatcttggg atcaccaaga aaccagtacc agatttcagc ttctatgacc gttcagcacc     480
```
aatctacaca cagcctcggt                                                   500

<210> SEQ ID NO 5
<211> LENGTH: 570
<212> TYPE: PRT
<213> ORGANISM: Brassica napus

<400> SEQUENCE: 5

Met Val Ala Ser Pro Asp Cys Arg Ile Ser Leu Ser Ala Pro Ser Cys
 1               5                  10                  15

Leu Arg Gly Ser Ser Gly Tyr Thr Lys His Ile Lys Leu Gly Ser Phe
            20                  25                  30

Cys Asn Gly Glu Leu Met Gly Lys Lys Leu Asn Leu Ala Gln Leu Arg
        35                  40                  45

Ser Ser Ser Thr Asn Ser Ser Gln Lys Arg Ile Gln Met Ser Leu Asn
    50                  55                  60

Ser Val Ala Gly Glu Ser Lys Val Gln Glu Ile Glu Ser Glu Lys Arg
65                  70                  75                  80

Asp Pro Lys Thr Val Ala Ser Ile Ile Leu Gly Gly Ala Gly Thr
                85                  90                  95

Arg Leu Phe Pro Leu Thr Lys Arg Arg Ala Lys Pro Ala Val Pro Ile
            100                 105                 110

Gly Gly Ala Tyr Arg Leu Ile Asp Val Pro Met Ser Asn Cys Ile Asn
        115                 120                 125

Ser Gly Ile Asn Lys Val Tyr Ile Leu Thr Gln Tyr Asn Ser Ala Ser
    130                 135                 140

Leu Asn Arg His Leu Thr Arg Ala Tyr Asn Ser Asn Gly Val Phe Gly
145                 150                 155                 160

Asp Gly Phe Val Glu Ala Leu Ala Ala Thr Gln Thr Pro Gly Glu Thr
                165                 170                 175

Gly Lys Arg Trp Phe Gln Gly Thr Ala Asp Ala Val Arg Gln Phe His
            180                 185                 190

Trp Leu Phe Glu Asp Ala Arg Ser Lys Glu Ile Glu Asp Val Leu Ile
        195                 200                 205

Leu Ser Gly Asp His Leu Tyr Arg Met Asp Tyr Met Asp Phe Val Gln
    210                 215                 220

Asp Gln Ser Thr Lys Arg Arg Asp Ile Ser Ile Ser Cys Ile Pro Ile
225                 230                 235                 240

Asp Asp Arg Glu Cys Lys Arg Val Gln Gln Ile His Ser Lys Ile Met
                245                 250                 255

Val Ser Tyr Lys Ser Leu Ser Val Leu His Gly Arg Arg Ala Ser Asp
            260                 265                 270

Phe Gly Leu Met Lys Ile Asp Asp Lys Gly Arg Val Ile Ser Phe Ser
        275                 280                 285

Glu Lys Pro Lys Gly Asp Asp Leu Lys Ala Met Ala Val Asp Thr Thr
    290                 295                 300

Val Leu Gly Leu Ser Lys Glu Glu Ala Glu Lys Lys Pro Tyr Ile Ala
305                 310                 315                 320

Ser Met Gly Val Tyr Val Phe Lys Lys Glu Ile Leu Leu Asn Leu Leu
                325                 330                 335

Arg Trp Arg Phe Pro Thr Ala Asn Asp Phe Gly Ser Glu Ile Ile Pro
            340                 345                 350

Phe Ser Ala Lys Glu Phe Tyr Val Asn Ala Tyr Leu Phe Asn Asp Tyr
        355                 360                 365

```
Trp Glu Asp Ile Gly Thr Ile Arg Ser Phe Phe Asp Ala Asn Leu Ala
        370                 375                 380

Leu Thr Glu His Pro Pro Ala Phe Ser Phe Tyr Asp Ala Ala Lys Pro
385                 390                 395                 400

Ile Tyr Thr Ser Arg Arg Asn Leu Pro Pro Ser Lys Ile Asp Gly Ser
                405                 410                 415

Lys Leu Ile Asp Ser Ile Ser His Gly Ser Phe Leu Thr Asn Cys
                420                 425                 430

Leu Ile Glu His Ser Ile Val Gly Ile Arg Ser Arg Val Gly Ser Asn
                435                 440                 445

Val Gln Leu Lys Asp Thr Val Met Leu Gly Ala Asp Phe Tyr Glu Thr
        450                 455                 460

Glu Ala Glu Val Ala Ala Leu Leu Ala Glu Glu Lys Val Pro Ile Gly
465                 470                 475                 480

Ile Gly Glu Asn Thr Lys Ile Ser Ser Lys Thr Lys Arg Ser Leu Ser
                485                 490                 495

Asn Gly Leu Pro Ser Lys Gln Lys Val Leu Asp Ser Phe Phe Pro Ser
                500                 505                 510

His Phe Pro Tyr Arg Glu Cys Ile Ile Asp Lys Asn Ala Arg Val Gly
                515                 520                 525

Lys Asn Val Val Ile Ala Asn Ser Glu Gly Val Gln Glu Ala Asp Arg
        530                 535                 540

Ser Ser Asp Gly Phe Tyr Ile Arg Ser Gly Ile Thr Val Ile Leu Lys
545                 550                 555                 560

Asn Ser Val Ile Ala Asp Gly Val Val Ile
                565                 570

<210> SEQ ID NO 6
<211> LENGTH: 1862
<212> TYPE: DNA
<213> ORGANISM: Brassica napus

<400> SEQUENCE: 6
ttcggcacga ggcaactctc ttttcttctc tgttatctct ccacttgtct cagaactctt      60
caacagccaa tatttccagc aaaaatggtt gcctctcctg actgcagaat ctccctctct     120
gctccgagct gcctacgcgg ctcctcgggc tacaccaagc acattaagct aggaagcttc     180
tgcaatgggg agctcatggg gaagaagctt aacttggctc agcttcgatc ttcttcaacc     240
aactcctctc aaaagagaat ccaaatgtct taaacagtg tagctggaga gagtaaggta      300
caagaaattg agtctgagaa aagagatcca agacagtag cttccattat tcttggaggt      360
ggagcaggaa ctcgactctt tcctctcaca aagcgtcgcg ctaagcctgc tgtccctatc     420
ggaggagcct ataggttgat agatgtaccg atgagcaact gcatcaacag tggaatcaac     480
aaagtctaca tactcacaca atacaactca gcgtcactga acaggcatct aactcgtgct     540
tacaactcca atggagtttt tggagacggc tttgttgagg ctcttgcagc cactcaaacg     600
ccaggagaaa caggtaaaag gtggttccaa ggtacagcag atgcggttcg gcagttccat     660 tggcttttg aggatgcaag aagcaaggag atagaggatg tgttgatcct ctctggtgat      720
cacctttaca ggatggatta catggatttt gtacaggatc agtcgacaaa gcggcgagat     780
ataagcattt cctgcatacc aatagatgac agggaatgca aaagagtcca acaaatccat     840
tcaaagatca tggtttctta taagtctctg tctgtgttac atggtagacg tgcttcagat     900
tttggtctaa tgaagataga tgacaaagga agagtcatct ctttcagtga aaaacctaaa     960
```

```
ggagatgacc tgaaagcaat ggcagtagac acaactgttc taggactttc taaggaggaa   1020
gctgaaaaga aaccatacat agcatcaatg ggagtttatg ttttcaagaa agaaatactg   1080
ttgaatctct tgagatggcg tttcccaaca gcaaacgact ttggttcaga gattataccc   1140
ttctcagcta aagagttcta tgtgaatgct tatctcttta tgactactg ggaagatata    1200 ggaaccataa gatctttctt tgatgcaaat ctcgccctca ctgagcatcc accagcattc   1260
agtttctacg acgcagcgaa accaatatat acatcaagga gaaacctgcc accatcaaag   1320
atagacggct ctaagctcat tgattcgatc atttctcatg gaagcttctt aacaaactgc   1380
ttaattgagc acagcattgt gggaattaga tcaagagtag gtagtaatgt tcagttgaag   1440
gacactgtga tgcttggggc agacttctac gaaactgaag cagaagttgc agcactactt   1500
gctgaggaaa aagttcccat tggaatagga gagaacacaa agatatcaag taagactaaa   1560
cgttcacttt caaatggttt accttcgaaa caaaaggttc ttgattcctt ttttccttct   1620
catttcccct acagagaatg cattatagac aagaatgcta gagttggcaa gaatgtagtt   1680 atagcaaaact cagagggagt acaagaagca gataggtcat cagatggatt ttacatcaga   1740
tctggcatta cagtaatctt gaagaactca gtaattgcag atggagttgt catatgagac   1800
ttttaagtca aaactatatt aataaaagca atttatttga taataaaaaa aaaaaaaaaa   1860
aa                                                                  1862

<210> SEQ ID NO 7
<211> LENGTH: 415
<212> TYPE: PRT
<213> ORGANISM: Brassica napus

<400> SEQUENCE: 7

Met Lys Arg Pro Leu Thr Thr Ser Pro Ser Thr Ser Ser Thr Ser
 1               5                  10                  15

Ser Ser Ala Cys Ile Leu Pro Thr Gln Pro Glu Thr Pro Arg Pro Lys
            20                  25                  30

Arg Ala Lys Arg Ala Lys Lys Ser Ser Ile Pro Thr Asp Val Lys Pro
        35                  40                  45

Gln Asn Pro Thr Ser Pro Ala Ser Thr Arg Arg Ser Ser Ile Tyr Arg
    50                  55                  60

Gly Val Thr Arg His Arg Trp Thr Gly Arg Tyr Glu Ala His Leu Trp
65                  70                  75                  80

Asp Lys Ser Ser Trp Asn Ser Ile Gln Asn Lys Lys Gly Lys Gln Val
                85                  90                  95

Tyr Leu Gly Ala Tyr Asp Ser Glu Glu Ala Ala Ala His Thr Tyr Asp
            100                 105                 110

Leu Ala Ala Leu Lys Tyr Trp Gly Pro Asp Thr Ile Leu Asn Phe Pro
        115                 120                 125

Ala Glu Thr Tyr Thr Lys Glu Leu Glu Glu Met Gln Arg Cys Thr Lys
    130                 135                 140

Glu Glu Tyr Leu Ala Ser Leu Arg Arg Gln Ser Ser Gly Phe Ser Arg
145                 150                 155                 160

Gly Val Ser Lys Tyr Arg Gly Val Ala Arg His His Asn Gly Arg
                165                 170                 175

Trp Glu Ala Arg Ile Gly Arg Val Phe Gly Asn Lys Tyr Leu Tyr Leu
            180                 185                 190

Gly Thr Tyr Asn Thr Gln Glu Glu Ala Ala Ala Tyr Asp Met Ala
        195                 200                 205
```

```
Ala Ile Glu Tyr Arg Gly Ala Asn Ala Val Thr Asn Phe Asp Ile Ser
        210                 215                 220

Asn Tyr Ile Asp Arg Leu Lys Lys Lys Gly Val Phe Pro Phe Pro Val
225                 230                 235                 240

Ser Gln Ala Asn His Gln Glu Ala Val Leu Ala Glu Ala Lys Gln Glu
                245                 250                 255

Val Glu Ala Lys Glu Glu Pro Thr Glu Glu Val Lys Gln Cys Val Glu
            260                 265                 270

Lys Glu Glu Pro Gln Glu Ala Lys Glu Glu Lys Thr Glu Lys Lys Gln
        275                 280                 285

Gln Gln Gln Glu Val Glu Ala Val Val Thr Cys Cys Ile Asp Ser
    290                 295                 300

Ser Glu Ser Asn Glu Leu Ala Trp Asp Phe Cys Met Met Asp Ser Gly
305                 310                 315                 320

Phe Ala Pro Phe Leu Thr Asp Ser Asn Leu Ser Ser Glu Asn Pro Ile
                325                 330                 335

Glu Tyr Pro Glu Leu Phe Asn Glu Met Gly Phe Glu Asp Asn Ile Asp
            340                 345                 350

Phe Met Phe Glu Glu Gly Lys Gln Asp Cys Leu Ser Leu Glu Asn Leu
        355                 360                 365

Asp Cys Cys Asp Gly Val Val Val Gly Arg Glu Ser Pro Thr Ser
370                 375                 380

Leu Ser Ser Ser Pro Leu Ser Cys Leu Ser Thr Asp Ser Ala Ser Ser
385                 390                 395                 400

Thr Thr Thr Thr Thr Ile Thr Ser Val Ser Cys Asn Tyr Ser Val
                405                 410                 415

<210> SEQ ID NO 8
<211> LENGTH: 1248
<212> TYPE: DNA
<213> ORGANISM: Brassica napus

<400> SEQUENCE: 8
atgaagagac ccttaaccac ttctccttct acctcctctt ctacttcttc ttcggcttgt      60
atacttccga ctcaaccaga gactccaagg cccaaacgag ccaaaagggc taagaaatct     120
tctattccta ctgatgttaa accacagaat cccaccagtc ctgcctccac cagacgcagc     180
tctatctaca gaggagtcac tagacataga tggacaggga gatacgaggc tcatctatgg     240
gacaaaagct cgtggaattc gattcagaac aagaaaggca acaagtttat ctgggagca     300
tatgacagcg aggaagcagc agcgcatacg tacgatctag ctgctctcaa gtactggggt     360
cccgacacca tcttgaactt tccggctgag acgtacacaa ggagttgga ggagatgcag     420
agatgtacaa aggaagagta tttggcttct ctccgccgcc agagcagtgg tttctctaga     480
ggcgtctcta aatatcgcgg cgtcgccagg catcaccata acggaagatg ggaagctagg     540
attggaaggg tgtttggaaa caagtacttg tacctcggca cttataatac gcaggaggaa     600
gctgcagctg catatgacat ggcggctata gagtacagag gcgcaaacgc agtgaccaac     660
ttcgacatta gtaactacat cgaccggtta aagaaaaaag tgtcttccc attccctgtg      720
agccaagcca atcatcaaga agctgttctt gctgaagcca acaagaagt ggaagctaaa      780
gaagagccta cagaagaagt gaagcagtgt gtcgaaaaag aagaaccgca agaagctaaa     840
gaagagaaga ctgagaaaaa acaacaacaa caagaagtgg aggaggcggt ggtcacttgc     900
tgcattgatt cttcggagag caatgagctg gcttgggact tctgtatgat ggattcaggg     960
```

-continued

```
tttgctccgt ttttgacgga ttcaaatctc tcgagtgaga atcccattga gtatcctgag      1020
cttttcaatg agatggggtt tgaggataac attgacttca tgttcgagga agggaagcaa      1080
gactgcttga gcttggagaa tctggattgt tgcgatggtg ttgttgtggt gggaagagag      1140
agcccaactt cattgtcgtc ttcaccgttg tcttgcttgt ctactgactc tgcttcatca      1200
acaacaacaa caacaataac ctctgtttct tgtaactatt ctgtctga                  1248
```

<210> SEQ ID NO 9
<211> LENGTH: 413
<212> TYPE: PRT
<213> ORGANISM: Brassica napus

<400> SEQUENCE: 9

```
Met Lys Arg Pro Leu Thr Thr Ser Pro Ser Ser Ser Ser Thr Ser
 1               5                  10                  15

Ser Ser Ala Cys Ile Leu Pro Thr Gln Ser Glu Thr Pro Arg Pro Lys
                20                  25                  30

Arg Ala Lys Arg Ala Lys Lys Ser Ser Leu Arg Ser Asp Val Lys Pro
            35                  40                  45

Gln Asn Pro Thr Ser Pro Ala Ser Thr Arg Arg Ser Ser Ile Tyr Arg
        50                  55                  60

Gly Val Thr Arg His Arg Trp Thr Gly Arg Tyr Glu Ala His Leu Trp
65                  70                  75                  80

Asp Lys Ser Ser Trp Asn Ser Ile Gln Asn Lys Lys Gly Lys Gln Val
                85                  90                  95

Tyr Leu Gly Ala Tyr Asp Ser Glu Glu Ala Ala Ala His Thr Tyr Asp
            100                 105                 110

Leu Ala Ala Leu Lys Tyr Trp Gly Pro Asn Thr Ile Leu Asn Phe Pro
        115                 120                 125

Val Glu Thr Tyr Thr Lys Glu Leu Glu Glu Met Gln Arg Cys Thr Lys
    130                 135                 140

Glu Glu Tyr Leu Ala Ser Leu Arg Arg Gln Ser Ser Gly Phe Ser Arg
145                 150                 155                 160

Gly Val Ser Lys Tyr Arg Gly Val Ala Arg His His Asn Gly Arg
                165                 170                 175

Trp Glu Ala Arg Ile Gly Arg Val Phe Gly Asn Lys Tyr Leu Tyr Leu
            180                 185                 190

Gly Thr Tyr Asn Thr Gln Glu Glu Ala Ala Ala Tyr Asp Met Ala
        195                 200                 205

Ala Ile Glu Tyr Arg Gly Ala Asn Ala Val Thr Asn Phe Asp Ile Gly
    210                 215                 220

Asn Tyr Ile Asp Arg Leu Lys Lys Lys Gly Val Phe Pro Phe Pro Val
225                 230                 235                 240

Ser Gln Ala Asn His Gln Glu Ala Val Leu Ala Glu Thr Lys Gln Glu
                245                 250                 255

Val Glu Ala Lys Glu Glu Pro Thr Glu Val Lys Gln Cys Val Glu
            260                 265                 270

Lys Glu Glu Ala Lys Glu Lys Thr Glu Lys Gln Gln Gln Glu
        275                 280                 285

Val Glu Glu Ala Val Ile Thr Cys Cys Ile Asp Ser Ser Glu Ser Asn
    290                 295                 300

Glu Leu Ala Trp Asp Phe Cys Met Met Asp Ser Gly Phe Ala Pro Phe
305                 310                 315                 320
```

Leu Thr Asp Ser Asn Leu Ser Glu Asn Pro Ile Glu Tyr Pro Glu
            325                 330                 335

Leu Phe Asn Glu Met Gly Phe Glu Asp Asn Ile Asp Phe Met Phe Glu
        340                 345                 350

Glu Gly Lys Gln Asp Cys Leu Ser Leu Glu Asn Leu Asp Cys Cys Asp
            355                 360                 365

Gly Val Val Val Gly Arg Glu Ser Pro Thr Ser Leu Ser Ser Ser
    370                 375                 380

Pro Leu Ser Cys Leu Ser Thr Asp Ser Ala Ser Ser Thr Thr Thr Thr
385                 390                 395                 400

Ala Thr Thr Val Thr Ser Val Ser Trp Asn Tyr Ser Val
            405                 410

<210> SEQ ID NO 10
<211> LENGTH: 1242
<212> TYPE: DNA
<213> ORGANISM: Brassica napus

<400> SEQUENCE: 10
atgaagagac ccttaaccac ttctccttct tcctcctctt ctacttcttc ttcggcctgt      60
atacttccga ctcaatcaga gactccaagg cccaaacgag ccaaaagggc taagaaatct     120
tctctgcgtt ctgatgttaa accacagaat cccaccagtc ctgcctccac cagacgcagc     180
tctatctaca gaggagtcac tagacataga tggacaggga gatacgaagc tcatctatgg     240
gacaaaagct cgtggaattc gattcagaac aagaaaggca acaagtttta tctgggagca     300
tatgacagcg aggaagcagc agcacatacg tacgatctag ctgctctcaa gtactggggt     360
cccaacacca tcttgaactt tccggttgag acgtacacaa aggagctgga ggagatgcag     420
agatgtacaa aggaagagta tttggcttct ctccgccgcc agagcagtgg tttctctaga     480
ggcgtctcta aatatcgcgg cgtcgccagg catcaccata tggaagatg ggaagctcgg      540
attggaaggg tgtttggaaa caagtacttg tacctcggca cctataatac gcaggaggaa     600
gctgcagctg catatgacat ggcggctata gagtacagag gtgcaaacgc agtgaccaac     660
ttcgacattg gtaactacat cgaccggtta agaaaaaaag gtgtcttccc gttccccgtg     720
agccaagcta atcatcaaga agctgttctt gctgaaacca acaagaagt ggaagctaaa      780
gaagagccta cagaagaagt gaagcagtgt gtcgaaaaag aagaagctaa agaagagaag     840
actgagaaaa acaacaaca agaagtggag gaggcggtga tcacttgctg cattgattct      900
tcagagagca atgagctggc ttgggacttc tgtatgatgg attcagggtt tgctccgttt     960
ttgactgatt caaatctctc gagtgagaat cccattgagt atcctgagct tttcaatgag    1020
atgggttttg aggataacat tgacttcatg ttcgaggaag ggaagcaaga ctgcttgagc    1080
ttggagaatc ttgattgttg cgatggtgtt gttgtggtgg gaagagagag cccaacttca    1140
ttgtcgtctt ctccgttgtc ctgcttgtct actgactctg cttcatcaac aacaacaaca    1200
gcaacaacag taacctctgt ttcttggaac tattctgtct ga                        1242

<210> SEQ ID NO 11
<211> LENGTH: 413
<212> TYPE: PRT
<213> ORGANISM: Brassica napus

<400> SEQUENCE: 11

Met Lys Arg Pro Leu Thr Thr Ser Pro Ser Ser Ser Ser Thr Ser
1               5                   10                  15

```
Ser Ser Ala Cys Ile Leu Pro Thr Gln Ser Glu Thr Pro Arg Pro Lys
                20                  25                  30

Arg Ala Lys Arg Ala Lys Lys Ser Ser Leu Arg Ser Asp Val Lys Pro
             35                  40                  45

Gln Asn Pro Thr Ser Pro Ala Ser Thr Arg Arg Ser Ser Ile Tyr Arg
 50                  55                  60

Gly Val Thr Arg His Arg Trp Thr Gly Arg Tyr Glu Ala His Leu Trp
 65                  70                  75                  80

Asp Lys Ser Ser Trp Asn Ser Ile Gln Asn Lys Gly Lys Gln Val
                 85                  90                  95

Tyr Leu Gly Ala Tyr Asp Ser Glu Glu Ala Ala His Thr Tyr Asp
                100                 105                 110

Leu Ala Ala Leu Lys Tyr Trp Gly Pro Asn Thr Ile Leu Asn Phe Pro
             115                 120                 125

Val Glu Thr Tyr Thr Lys Glu Leu Glu Glu Met Gln Arg Cys Thr Lys
130                 135                 140

Glu Glu Tyr Leu Ala Ser Leu Arg Arg Gln Ser Ser Gly Phe Ser Arg
145                 150                 155                 160

Gly Val Ser Lys Tyr Arg Gly Val Ala Arg His His His Asn Gly Arg
                165                 170                 175

Trp Glu Ala Arg Ile Gly Arg Val Phe Gly Asn Lys Tyr Leu Tyr Leu
             180                 185                 190

Gly Thr Tyr Asn Thr Gln Glu Glu Ala Ala Ala Ala Tyr Asp Met Ala
                195                 200                 205

Ala Ile Glu Tyr Arg Gly Ala Asn Ala Val Thr Asn Phe Asp Ile Gly
210                 215                 220

Asn Tyr Ile Asp Arg Leu Lys Lys Lys Gly Val Phe Pro Phe Pro Val
225                 230                 235                 240

Ser Gln Ala Asn His Gln Glu Ala Val Leu Ala Glu Thr Lys Gln Glu
                245                 250                 255

Val Glu Ala Lys Glu Glu Pro Thr Glu Glu Val Lys Gln Cys Val Glu
             260                 265                 270

Lys Glu Glu Ala Lys Glu Glu Lys Thr Glu Lys Lys Gln Gln Gln Glu
             275                 280                 285

Val Glu Glu Ala Val Ile Thr Cys Cys Ile Asp Ser Ser Glu Ser Asn
290                 295                 300

Glu Leu Ala Trp Asp Phe Cys Met Met Asp Ser Gly Phe Ala Pro Phe
305                 310                 315                 320

Leu Thr Asp Ser Asn Leu Ser Ser Glu Asn Pro Ile Glu Tyr Pro Glu
                325                 330                 335

Leu Phe Asn Glu Met Gly Phe Glu Asp Asn Ile Asp Phe Met Phe Glu
             340                 345                 350

Glu Gly Lys Gln Asp Cys Leu Ser Leu Glu Asn Leu Asp Cys Cys Asp
             355                 360                 365

Gly Val Val Val Val Gly Arg Glu Ser Pro Thr Ser Leu Ser Ser Ser
370                 375                 380

Pro Leu Ser Cys Leu Ser Thr Asp Ser Ala Ser Ser Thr Thr Thr Thr
385                 390                 395                 400

Ala Thr Thr Val Thr Ser Val Ser Trp Asn Tyr Ser Val
                405                 410
```

<210> SEQ ID NO 12
<211> LENGTH: 3609
<212> TYPE: DNA

<213> ORGANISM: Brassica napus

<400> SEQUENCE: 12

```
atgaagagac ccttaaccac ttctcctctct tcctcctctt ctacttcttc ttcggcctgt     60
atacttccga ctcaatcaga gactccaagg cccaaacgag ccaaaagggc taagaaatct    120
tctctgcgtt ctgatgttaa accacagaat cccaccagtc ctgcctccac cagacgcagc    180
tctatctaca gaggagtcac taggttgaga aaaataaaat aaaatgattg attcttttag    240
atttgatttg ggttatgttt tttttttttt tttttctaaa ctgcatttcg attgcatgtt    300
acagacatag atggacaggg agatacgaag ctcatctatg gacaaaagc tcgtggaatt     360
cgattcagaa caagaaaggc aaacaaggtt cttaattttt acaaaaaacc catcttgatt    420
ctgtaataaa gatctggcct ttttttttgtt ttgttttaat ctgattttgg tttctgttgt   480
ttgatctcaa cctcactgcc tcactctgcg ccttgttctt ctactcatca gtttatctgg    540
gtaattttt taattgagaa attaaaaaga gtttgatttg gtcaagagga tgaacgaatg     600
gaatctcaac tgctctgacg ccgtaattgc aggagcatat gacagcgagg aagcagcagc    660
acatacgtac gatctagctg ctctcaagta ctggggtccc aacaccatct tgaactttcc    720
ggtaagaaaa aataacttga ttgattgatt gatgcatgtt tgttcttgtt gaattaatta    780
aaaaaaatga tccaaacagg ttgagacgta cacaaaggag ctggaggaga tgcagagatg    840
tacaaaggaa gagtatttgg cttctctccg ccgccagagc agtggtttct ctagaggcgt    900
ctctaaatat cgcggcgtcg ccaggttctc tcttttttct ttttctttaa ttacgtgttt    960
gttttttaatt tgatttggta aattaattac accaaaatca ggaattaaat tttccttttc   1020
cgcatttttt gaaaaattaa ttaatagggt ggtgactaag aaaaagaaaa caaaatagga    1080
aatgtgattt tttggaaatt aaaaaagctg gacttttttca taagatttgc ttttagaatt   1140
tttatctctc tctctctctc tatcataatt aacttttgtt taagtacttg tcctgcaatt    1200
gagatgttta ttgtaattttg taaatatgtg atagctatag cttgattttc gcaaatgatt   1260
catttatcaa acattttttg ttatttcttt cccattttat attctgaaaa aacaagaaa     1320
gtaataaaaa ttgcaaatta tgggaaaaca ggcatcacca taatgaaga tgggaagctc     1380
ggattggaag ggtgtttgga acaagtact tgtacctcgg cacctatagt acgtacatcc     1440
ttgactcttt attcttaaat aataaattgt ttaaaataat atcagattaa ttttaaaaa    1500
aatttaagaa tcattatcgt aatcgaatat ttacaagggc ataacggatc ctttaaaaac    1560
aaaaactact ctggtatttg atttgaaaat agatattaca atgttttgag ttagtttata    1620
ctttatacta ctatttctta cgagttttat attatacttg tgattaagca ataattatt    1680
tgtttagttg gtcaattaga ataaacataa tggggaggca gtgagtgggg gtttacacac    1740
tcacgtgaga cgagagtttt gacatcatgt cccctcactt catactaatt gatttttatc    1800
tttaatatca gcattttcag agtattattt aactatctga ccctgcata attacctttt    1860
aaattctgca ttttgtggat ccaatactct gaacacgaaa attaaaaact ctgcagaagg    1920
gaatattaac accaactctt tactgaaaag taatactacc cttttttcaat tctttttgatc  1980
gggtccttag gttattaatg gatcttactt ttgaaaaaaa aaacaagtta caaaaaattc    2040
aagatgtttt tagagtttct cggattcagt tttgcaaaaa tataggcagt gttataacaa    2100
aagggcacat attattcaga tttattttt ttaaaagaaa aaaataggag agccaggagc    2160
ataataacaa aaaaatgaaa gtagtagatg tgaataaatg tatagaataa tgtaacgtta    2220
caagtgtaaa ggcgcgtgta gcgcgtagct cacgtggtaa cactctcctc tcacttcata   2280
```

```
aaaaggacaa attagttcag aagggctagg accaaacccg aggtcgatct ggtctacttt     2340 ttttgttg ggtggtggtt cattaaagaa tggttttaag agttgagtct gttctcagta      2400
gcagtcacga gccctcacgt gcatgtttca tctctctctc tctctaccat atctttcatc    2460
ttgtcctcag gaacaaaatc tggtctgctt tatttttaaa tgcaaattat tgtcttcata    2520
tttattatgt aaactatgaa gttaatagtg atagttatta cgtattagga gcttagagtt    2580
gacactaggt tggtatttt atttgctaac tagtcagtaa ttgtacgttc gtgtaattat     2640
ttatatattg ttgcatttgt ttaagctaca aacttggact cttttagcg tttagagcgg     2700 cggagagtgg agtagaaatg gtctcgtcca cgcctcaact ctatacgcat ctcacacacc    2760
tatagtgtaa ccctagttgt ccccactaac acgtcaccta attcccttg gttttttgtc     2820 tttattaggc atcttaaaat tctaaaaata aatattaaa atacatactg aaacacatgt     2880
ttggtgaagt aacacaaaca attatgtgaa aactgttact ttcaaaacac gctgactttg    2940
tttggttgtg cagatacgca ggaggaagct gcagctgcat atgacatggc ggctatagag    3000
tacagaggtg caaacgcagt gaccaacttc gacattggta actacatcga ccggttaaag    3060
aaaaaaggtg tcttcccgtt ccccgtgagc caagctaatc atcaagaagc tgttcttgct    3120
gaaaccaaac aagaagtgga agctaaagaa gagcctacag aagaagtgaa gcagtgtgtc    3180 gaaaagaag aagctaaaga agagaagact gagaaaaaac aacaacaaga agtggaggag     3240
gcggtgatca cttgctgcat tgattcttca gagagcaatg agctggcttg ggacttctgt    3300
atgatggatt cagggtttgc tccgtttttg actgattcaa atctctcgag tgagaatccc    3360
attgagtatc ctgagctttt caatgagatg ggttttgagg ataacattga cttcatgttc    3420
gaggaaggga agcaagactg cttgagcttg gagaatcttg attgttgcga tggtgttgtt    3480
gtggtgggaa gagagagccc aacttcattg tcgtcttctc cgttgtcctg cttgtctact    3540
gactctgctt catcaacaac aacaacagca acaacagtaa cctctgtttc ttggaactat    3600
tctgtctga                                                             3609
```

<210> SEQ ID NO 13
<211> LENGTH: 430
<212> TYPE: PRT
<213> ORGANISM: Arabidopsis thaliana

<400> SEQUENCE: 13

```
Met Lys Lys Arg Leu Thr Thr Ser Thr Cys Ser Ser Ser Pro Ser Ser
 1               5                  10                  15

Ser Val Ser Ser Ser Thr Thr Thr Ser Ser Pro Ile Gln Ser Glu Ala
                20                  25                  30

Pro Arg Pro Lys Arg Ala Lys Arg Ala Lys Lys Ser Ser Pro Ser Gly
            35                  40                  45

Asp Lys Ser His Asn Pro Thr Ser Pro Ala Ser Thr Arg Arg Ser Ser
        50                  55                  60

Ile Tyr Arg Gly Val Thr Arg His Arg Trp Thr Gly Arg Phe Glu Ala
 65                  70                  75                  80

His Leu Trp Asp Lys Ser Ser Trp Asn Ser Ile Gln Asn Lys Lys Gly
                85                  90                  95

Lys Gln Val Tyr Leu Gly Ala Tyr Asp Ser Glu Glu Ala Ala Ala His
                100                 105                 110

Thr Tyr Asp Leu Ala Ala Leu Lys Tyr Trp Gly Pro Asp Thr Ile Leu
            115                 120                 125
```

```
Asn Phe Pro Ala Glu Thr Tyr Thr Lys Glu Leu Glu Glu Met Gln Arg
    130                 135                 140

Val Thr Lys Glu Glu Tyr Leu Ala Ser Leu Arg Arg Gln Ser Ser Gly
145                 150                 155                 160

Phe Ser Arg Gly Val Ser Lys Tyr Arg Gly Val Ala Arg His His His
                165                 170                 175

Asn Gly Arg Trp Glu Arg Ile Gly Arg Val Phe Gly Asn Lys Tyr
                180                 185                 190

Leu Tyr Leu Gly Thr Tyr Asn Thr Gln Glu Glu Ala Ala Ala Tyr
        195                 200                 205

Asp Met Ala Ala Ile Glu Tyr Arg Gly Ala Asn Ala Val Thr Asn Phe
    210                 215                 220

Asp Ile Ser Asn Tyr Ile Asp Arg Leu Lys Lys Lys Gly Val Phe Pro
225                 230                 235                 240

Phe Pro Val Asn Gln Ala Asn His Gln Glu Gly Ile Leu Val Glu Ala
                245                 250                 255

Lys Gln Glu Val Glu Thr Arg Glu Ala Lys Glu Pro Arg Glu Glu
                260                 265                 270

Val Lys Gln Gln Tyr Val Glu Glu Pro Gln Glu Glu Glu Glu Lys
            275                 280                 285

Glu Glu Glu Lys Ala Glu Gln Gln Ala Glu Ile Val Gly Tyr Ser
    290                 295                 300

Glu Glu Ala Ala Val Val Asn Cys Cys Ile Asp Ser Ser Thr Ile Met
305                 310                 315                 320

Glu Met Asp Arg Cys Gly Asp Asn Asn Glu Leu Ala Trp Asn Phe Cys
                325                 330                 335

Met Met Asp Thr Gly Phe Ser Pro Phe Leu Thr Asp Gln Asn Leu Ala
                340                 345                 350

Asn Glu Asn Pro Ile Glu Tyr Pro Glu Leu Phe Asn Glu Leu Ala Phe
                355                 360                 365

Glu Asp Asn Ile Asp Phe Met Phe Asp Asp Gly Lys His Glu Cys Leu
    370                 375                 380

Asn Leu Glu Asn Leu Asp Cys Cys Val Val Gly Arg Glu Ser Pro Pro
385                 390                 395                 400

Ser Ser Ser Ser Pro Leu Ser Cys Leu Ser Thr Asp Ser Ala Ser Ser
                405                 410                 415

Thr Thr Thr Thr Thr Thr Ser Val Ser Cys Asn Tyr Leu Val
                420                 425                 430

<210> SEQ ID NO 14
<211> LENGTH: 1540
<212> TYPE: DNA
<213> ORGANISM: Arabidopsis thaliana

<400> SEQUENCE: 14
aaaccactct gcttcctctt cctctgagaa atcaaatcac tcacactcca aaaaaaaatc      60
taaactttct cagagtttaa tgaagaagcg cttaaccact tccacttgtt cttcttctcc     120
atcttcctct gtttcttctt ctactactac ttcctctcct attcagtcgg aggctccaag     180
gcctaaacga gccaaaaggg ctaagaaatc ttctccttct ggtgataaat ctcataaccc     240
gacaagccct gcttctaccc gacgcagctc tatctacaga ggagtcacta gacatagatg     300
gactgggaga ttcgaggctc atctttggga caaaagctct tggaattcga ttcagaacaa     360
gaaaggcaaa caagtttatc tgggagcata tgacagtgaa gaagcagcag cacatacgta     420
```

-continued

```
cgatctggct gctctcaagt actggggacc cgacaccatc ttgaattttc cggcagagac      480
gtacacaaag gaattggaag aaatgcagag agtgacaaag gaagaatatt tggcttctct      540
ccgccgccag agcagtggtt tctccagagg cgtctctaaa tatcgcggcg tcgctaggca      600
tcaccacaac ggaagatggg aggctcggat cggaagagtg tttgggaaca agtacttgta      660
cctcggcacc tataatacgc aggaggaagc tgctgcagca tatgacatgg ctgcgattga      720
gtatcgaggc gcaaacgcgg ttactaattt cgacattagt aattacattg accggttaaa      780
gaagaaaggt gttttcccgt tccctgtgaa ccaagctaac catcaagagg gtattcttgt      840
tgaagccaaa caagaagttg aaacgagaga agcgaaggaa gagcctagag aagaagtgaa      900
acaacagtac gtggaagaac caccgcaaga agaagaagag aaggaagaag agaaagcaga      960
gcaacaagaa gcagagattg taggatattc agaagaagca gcagtggtca attgctgcat     1020
agactcttca accataatgg aaatggatcg ttgtggggac aacaatgagc tggcttggaa     1080
cttctgtatg atggatacag ggttttctcc gttttttgact gatcagaatc tcgcgaatga     1140
gaatcccata gagtatccgg agctattcaa tgagttagca tttgaggaca acatcgactt     1200
catgttcgat gatgggaagc acgagtgctt gaacttggaa atctggatt gttgcgtggt      1260 gggaagagag agcccaccct cttcttcttc accattgtct tgcttatcta ctgactctgc     1320
ttcatcaaca acaacaacaa caacctcggt ttccttgtaac tatttggtct gagagagaga    1380
gctttgcctt ctagtttgaa tttctatttc ttccgcttct tcttcttttt tttcttttgt     1440
tgggttctgc ttagggtttg tatttcagtt tcagggcttg ttcgttggtt ctgaataatc     1500
aatgtctttg cccctttct aatgggtacc tgaagggcga                            1540
```

<210> SEQ ID NO 15
<211> LENGTH: 20
<212> TYPE: DNA
<213> ORGANISM: Arabidopsis thaliana

<400> SEQUENCE: 15

```
aaatctaaac tttctcagag                                                   20
```

<210> SEQ ID NO 16
<211> LENGTH: 42
<212> TYPE: DNA
<213> ORGANISM: Arabidopsis thaliana

<400> SEQUENCE: 16

```
tcagggcttg ttcgttggtt ctgaataatc aatgtctttg cc                          42
```

<210> SEQ ID NO 17
<211> LENGTH: 356
<212> TYPE: PRT
<213> ORGANISM: Arabidopsis thaliana

<400> SEQUENCE: 17

```
Met Asp Trp Glu Ile Arg Gly Ser Ser Leu Gly Gln Lys Leu Leu Glu
 1               5                  10                  15

Phe Asp Ser Glu Gln Glu Arg Gln Thr Arg Phe Arg Ala Tyr Asp Ser
                20                  25                  30

Glu Glu Ala Ala Ala His Thr Tyr Asp Leu Ala Ala Leu Lys Tyr Trp
            35                  40                  45

Gly Pro Asp Thr Ile Leu Asn Phe Pro Ala Glu Thr Tyr Thr Lys Glu
        50                  55                  60

Leu Glu Glu Met Gln Arg Val Thr Lys Glu Glu Tyr Leu Ala Ser Leu
```

```
                65                  70                  75                  80
Arg Arg Gln Ser Ser Gly Phe Ser Arg Gly Val Ser Lys Tyr Arg Gly
                    85                  90                  95

Val Ala Arg His His His Asn Gly Arg Trp Glu Ala Arg Ile Gly Arg
                100                 105                 110

Val Phe Gly Asn Lys Tyr Leu Tyr Leu Gly Thr Tyr Asn Thr Gln Glu
                115                 120                 125

Glu Ala Ala Ala Tyr Asp Met Ala Ala Ile Glu Tyr Arg Gly Ala
            130                 135                 140

Asn Ala Val Thr Asn Phe Asp Ile Ser Asn Tyr Ile Asp Arg Leu Lys
145                 150                 155                 160

Lys Lys Gly Val Phe Pro Phe Pro Val Asn Gln Ala Asn His Gln Glu
                165                 170                 175

Gly Ile Leu Val Glu Ala Lys Gln Glu Val Thr Arg Glu Ala Lys
            180                 185                 190

Glu Glu Pro Arg Glu Glu Val Lys Gln Gln Tyr Val Glu Gly Pro Pro
                195                 200                 205

Gln Glu Glu Glu Glu Lys Glu Glu Lys Ala Glu Gln Gln Glu Ala
            210                 215                 220

Glu Ile Val Gly Tyr Ser Glu Glu Ala Ala Val Val Asn Cys Cys Ile
225                 230                 235                 240

Asp Ser Ser Thr Ile Met Glu Met Asp Arg Cys Gly Asp Asn Glu
            245                 250                 255

Leu Ala Trp Asn Phe Cys Met Met Asp Thr Gly Phe Ser Pro Phe Leu
                260                 265                 270

Thr Asp Gln Asn Leu Ala Asn Glu Asn Pro Ile Glu Tyr Pro Glu Leu
            275                 280                 285

Phe Asn Glu Leu Ala Phe Glu Asp Asn Ile Asp Phe Met Phe Asp Asp
        290                 295                 300

Gly Lys His Glu Cys Leu Asn Leu Glu Asn Leu Asp Cys Cys Val Val
305                 310                 315                 320

Gly Arg Glu Ser Pro Pro Ser Ser Ser Pro Leu Ser Cys Leu Ser
            325                 330                 335

Thr Asp Ser Ala Ser Ser Thr Thr Thr Thr Thr Ser Val Ser Cys
            340                 345                 350

Asn Tyr Leu Val
        355

<210> SEQ ID NO 18
<211> LENGTH: 1580
<212> TYPE: DNA
<213> ORGANISM: Arabidopsis thaliana

<400> SEQUENCE: 18
cagggtttat ttaacttgcc ctttctcgtt tcctcctttt tttcttaaac cactctgctt      60
cctcttcctc tgagaaatca aatcactcac actccaaaaa aaaatctaaa ctttctcaga     120
gtttaatgaa gaagcgctta accacttcca cttgttcttc ttctccatct tcctctgttt     180
cttcttctac tactacttcc tctcctattc agtcggaggc tccaaggcct aaacgagcca     240
aaagggctaa gaaatcttct ccttctggtg ataaatctca taacccgaca agccctgctt     300
ctacccgacg cagctctatc tacagaggag tcactagaca tagatggact gggagattcg     360
aggctcatct ttgggacaaa agctcttgga attcgattca gaacaagaaa ggcaaacaag     420
gtttcgagca tatgacagtg aagaagcagc agcacatacg tacgatctgg ctgctctcaa     480
```

```
gtactgggga cccgacacca tcttgaattt tccggcagag acgtacacaa aggaattgga      540
agaaatgcag agagtgacaa aggaagaata tttggcttct ctccgccgcc agagcagtgg      600
tttctccaga ggcgtctcta aatatcgcgg cgtcgctagg catcaccaca acggaagatg      660
ggaggctcgg atcggaagag tgtttgggaa caagtacttg tacctcggca cctataatac      720
gcaggaggaa gctgctgcag catatgacat ggctgcgatt gagtatcgag gcgcaaacgc      780
ggttactaat ttcgacatta gtaattacat tgaccggtta aagaagaaag gtgttttccc      840
gttccctgtg aaccaagcta accatcaaga gggtattctt gttgaagcca aacaagaagt      900
tgaaacgaga gaagcgaagg aagagcctag agaagaagtg aaacaacagt acgtggaaga      960
accaccgcaa gaagaagaag agaaggaaga agagaaagca gagcaacaag aagcagagat     1020
tgtaggatat tcagaagaag cagcagtggt caattgctgc atagactctt caaccataat     1080
ggaaatggat cgttgtgggg acaacaatga gctggcttgg aacttctgta tgatggatac     1140
agggttttct ccgttttga ctgatcagaa tctcgcgaat gagaatccca tagagtatcc     1200
ggagctattc aatgagttag catttgagga caacatcgac ttcatgttcg atgatgggaa     1260
gcacgagtgc ttgaacttgg aaaatctgga ttgttgcgtg gtgggaagag agagcccacc     1320
ctcttcttct tcaccattgt cttgcttatc tactgactct gcttcatcaa caacaacaac     1380
aacaacctcg gtttcttgta actatttggt ctgagagaga gagctttgcc ttctagtttg     1440
aatttctatt tcttccgctt cttcttcttt ttttctttt gttgggttct gcttagggtt     1500
tgtatttcag tttcagggct tgttcgttgg ttctgaataa tcaatgtctt tgcccctttt     1560
ctaatgctcc aagttcagat                                                 1580

<210> SEQ ID NO 19
<211> LENGTH: 9
<212> TYPE: RNA
<213> ORGANISM: Artificial Sequence
<220> FEATURE:
<223> OTHER INFORMATION: A synthetic oligonucleotide.

<400> SEQUENCE: 19 uucaagaga                                                                9

<210> SEQ ID NO 20
<211> LENGTH: 1975
<212> TYPE: DNA
<213> ORGANISM: Solanum tuberosum L.

<400> SEQUENCE: 20
aagcttatgt tgccatatag agtagtttgt gatggtatac ttcataaact ttaacttatg       60
ttaaatttgt aatgataaaa ttttattgt aaattaaaaa ttacttataa aattgggcat      120
tataacatat gaaagacaaa ttgtgttaca tattttactt ttgactttaa tatgaatatt      180
tcaatttaaa tcattgttt attttctctt tcttttaca ggtataaaag gtgaaaattg      240
aagcaagatt gattgcaagc tatgtgtcac cacgttattg atactttgga agaaatttt      300 acttatatgt ctttgtttag gagtaatatt tgatatgttt tagttagatt ttcttgtcat      360
ttatgcttta gtataatttt agttatttt attatatgat catgggtgaa ttttgataca      420 aatattttg tcattaaata aattaattta tcacaacttg attactttca gtgacaaaaa      480
atgtattgtc gtagtaccct ttttgttga atatgaataa ttttttttat tttgtgacaa      540
ttgtaattgt cactacttat gataatattt agtgacatat atgtcgtcgg taaaagcaaa      600
```

-continued

```
cactttcagt gacaaaataa tagatttaat cacaaaatta ttaaccttTT  ttataataat    660
aaatttatcc ctaatttata catttaagga caaagtattt ttTTtatata taaaaaatag    720
tctttagtga cgatcgtagt gttgagtcta gaaatcataa tgttgaatct agaaaaatct    780
catgcagtgt aaaataaacc tcaaaaagga cgttcagtcc atagagggg tgtatgtgac    840 accccaacct cagcaaaaga aaacctccct tcaacaagga catttgcggt gctaaacaat    900
ttcaagtctc atcacacata tatttattat ataatactaa taaagaatag aaaaggaaag    960
gtaaacatca ttaaatcgtc tttgtatatt tttagtgaca actgattgac gaaatctttt   1020
tcgtcacaca aaatttttag tgacgaaaca tgatttatag atgatgaaat tatttgtccc   1080
tcataatcta atttgttgta gtgatcatta ctcctttgtt tgttttattt gtcatgttag   1140
tccattaaaa aaaatatct ctcttcttat gtacgtgaat ggttggaacg gatctattat    1200
ataatactaa taaagaatag aaaaaggaaa gtgagtgagg ttcgagggag agaatctgtt   1260
taatatcaga gtcgatcatg tgtcaatttt atcgatatga ccctaacttc aactgagttt   1320
aaccaattcc gataaggcga gaaatatcat agtattgagt ctagaaaaat ctcatgtagt   1380
gtggggtaaa cctcagcaag gacgttgagt ccatagaggg gggtgtatgt gacaccccaa   1440
cctcagcaaa agaaaacctc ccctcaagaa ggacatttgc ggtgctaaac aatttcaagt   1500
ctcatcacac atatatat attatataat actaataaat aatagaaaaa ggaaaggtaa     1560
acatcactaa cgacagttgc ggtgcaaact gagtgaggta ataaacatca ctaacttta    1620 ttggttatgt caaactcaaa gtaaaatttc tcaacttgtt tacgtgccta tatataccat   1680
gcttgttata tgctcaaagc accaacaaaa tttaaaaaca ctttgaacat ttgcaaaatg   1740
gcaactacta aaactttttt aatttattt tttatgatat tagcaactac tagttcaaca    1800
tgtgctaagt tggaagaaat ggttactgtt ctaagtattg atggaggtgg aattaaggga   1860
atcattccag ctatcattct cgaatttctt gaaggacaac ttcaggtatt gtaaaaatat   1920
tttttaatgt atgtgcgtaa gtgtgacact actactatag tcattctggg tacct        1975
```

<210> SEQ ID NO 21
<211> LENGTH: 31
<212> TYPE: DNA
<213> ORGANISM: Artificial Sequence
<220> FEATURE:
<223> OTHER INFORMATION: A synthetic oligonucleotide.

<400> SEQUENCE: 21
ccaaggatcc aaatctaaac tttctcagag t                            31

<210> SEQ ID NO 22
<211> LENGTH: 29
<212> TYPE: DNA
<213> ORGANISM: Artificial Sequence
<220> FEATURE:
<223> OTHER INFORMATION: A synthetic oligonucleotide.

<400> SEQUENCE: 22
ccttacgcgt ggcaaagaca ttgattatt                               29

<210> SEQ ID NO 23
<211> LENGTH: 30
<212> TYPE: DNA
<213> ORGANISM: Artificial Sequence
<220> FEATURE:
<223> OTHER INFORMATION: A synthetic oligonucleotide.

<400> SEQUENCE: 23
gtgatgatgg accaaatagt tacaagaaac                                    30

<210> SEQ ID NO 24
<211> LENGTH: 25
<212> TYPE: DNA
<213> ORGANISM: Artificial Sequence
<220> FEATURE:
<223> OTHER INFORMATION: A synthetic oligonucleotide.

<400> SEQUENCE: 24
catcaccatt gagagagaga gcttt                                         25

<210> SEQ ID NO 25
<211> LENGTH: 22
<212> TYPE: DNA
<213> ORGANISM: Artificial Sequence
<220> FEATURE:
<223> OTHER INFORMATION: A synthetic oligonucleotide.

<400> SEQUENCE: 25
tgtgacaatg gtaccggtat gg                                            22

<210> SEQ ID NO 26
<211> LENGTH: 19
<212> TYPE: DNA
<213> ORGANISM: Artificial Sequence
<220> FEATURE:
<223> OTHER INFORMATION: A synthetic oligonucleotide.

<400> SEQUENCE: 26
gccctgggag catcatctc                                                19

<210> SEQ ID NO 27
<211> LENGTH: 24
<212> TYPE: DNA
<213> ORGANISM: Artificial Sequence
<220> FEATURE:
<223> OTHER INFORMATION: A synthetic oligonucleotide.

<400> SEQUENCE: 27
tgtctggcaa caacaaggat tagt                                          24

<210> SEQ ID NO 28
<211> LENGTH: 25
<212> TYPE: DNA
<213> ORGANISM: Artificial Sequence
<220> FEATURE:
<223> OTHER INFORMATION: A synthetic oligonucleotide.

<400> SEQUENCE: 28
gcggaggttg aaggatagat tagtc                                         25

<210> SEQ ID NO 29
<211> LENGTH: 18
<212> TYPE: DNA
<213> ORGANISM: Artificial Sequence
<220> FEATURE:
<223> OTHER INFORMATION: A synthetic oligonucleotide.

<400> SEQUENCE: 29
aaagccgtcg cgaagcta                                                 18

<210> SEQ ID NO 30
<211> LENGTH: 20
<212> TYPE: DNA

```
<213> ORGANISM: Artificial Sequence
<220> FEATURE:
<223> OTHER INFORMATION: A synthetic oligonucleotide.

<400> SEQUENCE: 30
ggagccaatt gtcggatttg                                           20

<210> SEQ ID NO 31
<211> LENGTH: 25
<212> TYPE: DNA
<213> ORGANISM: Artificial Sequence
<220> FEATURE:
<223> OTHER INFORMATION: A synthetic oligonucleotide.

<400> SEQUENCE: 31
atggcgtctg tatctgcaat tggag                                     25

<210> SEQ ID NO 32
<211> LENGTH: 25
<212> TYPE: DNA
<213> ORGANISM: Artificial Sequence
<220> FEATURE:
<223> OTHER INFORMATION: A synthetic oligonucleotide.

<400> SEQUENCE: 32
ggatttgagt gaaatcttgt cgtcg                                     25

<210> SEQ ID NO 33
<211> LENGTH: 18
<212> TYPE: DNA
<213> ORGANISM: Artificial Sequence
<220> FEATURE:
<223> OTHER INFORMATION: A synthetic oligonucleotide.

<400> SEQUENCE: 33
aacaggcggg tcggatct                                             18

<210> SEQ ID NO 34
<211> LENGTH: 18
<212> TYPE: DNA
<213> ORGANISM: Artificial Sequence
<220> FEATURE:
<223> OTHER INFORMATION: A synthetic oligonucleotide.

<400> SEQUENCE: 34
gcggctgcca tctttgag                                             18

<210> SEQ ID NO 35
<211> LENGTH: 19
<212> TYPE: DNA
<213> ORGANISM: Artificial Sequence
<220> FEATURE:
<223> OTHER INFORMATION: A synthetic oligonucleotide.

<400> SEQUENCE: 35
gaggccaagg tggatccat                                            19

<210> SEQ ID NO 36
<211> LENGTH: 20
<212> TYPE: DNA
<213> ORGANISM: Artificial Sequence
<220> FEATURE:
<223> OTHER INFORMATION: A synthetic oligonucleotide.

<400> SEQUENCE: 36
caaagccacc aagcatgttg                                           20
```

<210> SEQ ID NO 37
<211> LENGTH: 22
<212> TYPE: DNA
<213> ORGANISM: Artificial Sequence
<220> FEATURE:
<223> OTHER INFORMATION: A synthetic oligonucleotide.

<400> SEQUENCE: 37
ccaacggtgg atctgtgtct ac                                            22

<210> SEQ ID NO 38
<211> LENGTH: 21
<212> TYPE: DNA
<213> ORGANISM: Artificial Sequence
<220> FEATURE:
<223> OTHER INFORMATION: A synthetic oligonucleotide.

<400> SEQUENCE: 38
tcactgcaaa actcgctggt t                                             21

<210> SEQ ID NO 39
<211> LENGTH: 23
<212> TYPE: DNA
<213> ORGANISM: Artificial Sequence
<220> FEATURE:
<223> OTHER INFORMATION: A synthetic oligonucleotide.

<400> SEQUENCE: 39
cagtctgcag aggaagccat agt                                           23

<210> SEQ ID NO 40
<211> LENGTH: 22
<212> TYPE: DNA
<213> ORGANISM: Artificial Sequence
<220> FEATURE:
<223> OTHER INFORMATION: A synthetic oligonucleotide.

<400> SEQUENCE: 40
aggtctggga cgtatagcca aa                                            22

<210> SEQ ID NO 41
<211> LENGTH: 22
<212> TYPE: DNA
<213> ORGANISM: Artificial Sequence
<220> FEATURE:
<223> OTHER INFORMATION: A synthetic oligonucleotide.

<400> SEQUENCE: 41
tggattctgc tggcgttact ac                                            22

<210> SEQ ID NO 42
<211> LENGTH: 24
<212> TYPE: DNA
<213> ORGANISM: Artificial Sequence
<220> FEATURE:
<223> OTHER INFORMATION: A synthetic oligonucleotide.

<400> SEQUENCE: 42
agcctatcaa gatcgacgaa ctct                                          24

<210> SEQ ID NO 43
<211> LENGTH: 21
<212> TYPE: DNA
<213> ORGANISM: Artificial Sequence
<220> FEATURE:

```
<223> OTHER INFORMATION: A synthetic oligonucleotide.

<400> SEQUENCE: 43
aaacgagcca aaagggctaa g                                               21

<210> SEQ ID NO 44
<211> LENGTH: 20
<212> TYPE: DNA
<213> ORGANISM: Artificial Sequence
<220> FEATURE:
<223> OTHER INFORMATION: A synthetic oligonucleotide.

<400> SEQUENCE: 44
gggcttgtcg ggttatgaga                                                 20
```